(12) United States Patent
Kim et al.

(10) Patent No.: US 10,633,430 B2
(45) Date of Patent: *Apr. 28, 2020

(54) ENGINEERING OF IMMUNOGLOBULIN DOMAINS

(71) Applicant: National Research Council of Canada, Ottawa (CA)

(72) Inventors: Dae Young Kim, Ottawa (CA); Jamshid Tanha, Ottawa (CA)

(73) Assignee: National Research Council of Canada, Ottawa (CA)

( * ) Notice: Subject to any disclaimer, the term of this patent is extended or adjusted under 35 U.S.C. 154(b) by 393 days.

This patent is subject to a terminal disclaimer.

(21) Appl. No.: 15/178,758

(22) Filed: Jun. 10, 2016

(65) Prior Publication Data

US 2017/0044238 A1 Feb. 16, 2017

Related U.S. Application Data

(62) Division of application No. 13/981,967, filed as application No. PCT/CA2012/000126 on Jan. 27, 2012, now Pat. No. 9,371,371.

(Continued)

(51) Int. Cl.
*C40B 40/10* (2006.01)
*C07K 16/00* (2006.01)
(Continued)

(52) U.S. Cl.
CPC ............ *C07K 16/005* (2013.01); *C07K 16/18* (2013.01); *C07K 16/40* (2013.01);
(Continued)

(58) Field of Classification Search
None
See application file for complete search history.

(56) References Cited

U.S. PATENT DOCUMENTS 9,371,371 B2 6/2016 Kim et al.
2009/0220485 A1 9/2009 Tanha

FOREIGN PATENT DOCUMENTS

WO WO 2006/099747 A1 9/2006
WO WO 2009/079793 A1 7/2009

OTHER PUBLICATIONS

Chinese Office Communication dated Aug. 26, 2015 for Application No. 2012-800165874.

(Continued)

*Primary Examiner* — Christian C Boesen
(74) *Attorney, Agent, or Firm* — Wolf, Greenfield & Sacks, P.C.

(57) ABSTRACT

The present invention provides a single domain antibody (sdAb) scaffold comprising one or more than one non-canonical disulfide bond in the framework region (FR). The one or more than one non-canonical disulfide bond may be formed between cysteines introduced by mutations in FR2 and FR3. In the case where the sdAb scaffold is a $V_H$, the Cys may be introduced at any one of positions 47-49 and any one of positions 67-71, based on Kabat numbering; in one example, the Cys may be introduced at positions 49 and 69, based on Kabat numbering. In the case where the sdAb scaffold is a $V_L$, the Cys residues may be introduced at any one of positions 46-49 and any one of positions 62-66, based on Kabat numbering; in one example, the Cys residues may be introduced at positions 48 and 64, based on Kabat numbering.

10 Claims, 31 Drawing Sheets
Specification includes a Sequence Listing.

Related U.S. Application Data

(60) Provisional application No. 61/437,174, filed on Jan. 28, 2011.

(51) Int. Cl.
  *C07K 16/18* (2006.01)
  *C07K 16/40* (2006.01)

(52) U.S. Cl.
  CPC .... *C07K 2317/56* (2013.01); *C07K 2317/565* (2013.01); *C07K 2317/567* (2013.01); *C07K 2317/569* (2013.01); *C07K 2317/624* (2013.01); *C07K 2317/92* (2013.01); *C07K 2317/94* (2013.01); *C07K 2318/00* (2013.01); *C40B 40/10* (2013.01)

(56) References Cited

OTHER PUBLICATIONS

Russian Office Communication dated Oct. 29, 2015 for Application No. 2013139260/10 (059572).
Amzel et al., Three-dimensional structure of immunoglobulins. Annu Rev Biochem. 1979;48:961-97.
Arbabi-Ghahroudi et al., Aggregation-resistant VHs selected by in vitro evolution tend to have disulfide-bonded loops and acidic isoelectric points. Protein Eng Des Sel. Feb. 2009;22(2):59-66. doi: 10.1093/protein/gzn071. Epub Nov. 24, 2008.
Arbabi-Ghahroudi et al., Selection of non-aggregating VH binders from synthetic VH phage-display libraries. Methods Mol Biol. 2009;525:187-216, xiii. doi: 10.1007/978-1-59745-554-1_10.
Arbabi-Ghahroudi et al., Site-directed mutagenesis for improving biophysical properties of VH domains. Chapter 22 in In Vitro Mutagenesis Protocols, Third Edition. And Methods Mol Biol. 2010;634:309-30. doi: 10.1007/978-1-60761-652-8_22.
Betz, Disulfide bonds and the stability of globular proteins. Protein Sci. Oct. 1993;2(10):1551-8.
Bloom et al., Protein stability promotes evolvability. Proc Natl Acad Sci U S A. Apr. 11, 2006;103(15):5869-74. Epub Mar. 31, 2006.
Chan et al., Engineering a camelid antibody fragment that binds to the active site of human lysozyme and inhibits its conversion into amyloid fibrils. Biochemistry. Oct. 21, 2008;47(42):11041-54. doi: 10.1021/bi8005797. Epub Sep. 25, 2008.
Davies et al., Antibody VH domains as small recognition units. Biotechnology (N Y). May 1995;13(5):475-9.
Davies et al., 'Camelising' human antibody fragments: NMR studies on VH domains. FEBS Lett. Feb. 21, 1994;339(3):285-90.
Davies et al., Single antibody domains as small recognition units: design and in vitro antigen selection of camelized, human VH domains with improved protein stability. Protein Eng. Jun. 1996;9(6):531-7.
Hagihara et al., Stabilization of an immunoglobulin fold domain by an engineered disulfide bond at the buried hydrophobic region. J Biol Chem. Dec. 14, 2007;282(50):36489-95. Epub Oct. 11, 2007.
Holliger et al., Engineered antibody fragments and the rise of single domains. Nat Biotechnol. Sep. 2005;23(9):1126-36.
Hoogenboom, Selecting and screening recombinant antibody libraries. Nat Biotechnol. Sep. 2005;23(9):1105-16.
Horwich, Protein aggregation in disease: a role for folding intermediates forming specific multimeric interactions. J Clin Invest. Nov. 2002;110(9):1221-32.
Hurle et al., A role for destabilizing amino acid replacements in light-chain amyloidosis. Proc Natl Acad Sci U S A. Jun. 7, 1994;91(12):5446-50.
Hussack et al., A V(L) single-domain antibody library shows a high-propensity to yield non-aggregating binders. Protein Eng Des Sel. Jun. 2012;25(6):313-8. doi: 10.1093/protein/gzs014. Epub Apr. 6, 2012.
Hussack et al., Characterization of single-domain antibodies with an engineered disulfide bond. Methods Mol Biol. 2012;911:417-29. doi: 10.1007/978-1-61779-968-6_25.
Hussack et al., Engineered single-domain antibodies with high protease resistance and thermal stability. PLoS One. 2011;6(11):e28218. doi: 10.1371/journal.pone.0028218. Epub Nov. 30, 2011.
Hussack et al., Isolation and characterization of Clostridium difficile toxin-specific single-domain antibodies. Methods Mol Biol. 2012;911:211-39. doi: 10.1007/978-1-61779-968-6_14.
Jespers et al., Aggregation-resistant domain antibodies selected on phage by heat denaturation. Nat Biotechnol. Sep. 2004;22(9):1161-5. Epub Aug. 8, 2004.
Kazlauskas et al., Finding better protein engineering strategies. Nat Chem Biol. Aug. 2009;5(8):526-9. doi: 10.1038/nchembio0809-526.
Kim et al., Sodium dodecyl sulfate-polyacrylamide gel electrophoresis for screening nonaggregating human antibody heavy chain variable domains. Anal Biochem. Aug. 2010;403(1-2):117-9. doi: 10.1016/j.ab.2010.04.017. Epub Apr. 18, 2010.
Kim et al., Solubility and stability engineering of human VH domains. Methods Mol Biol. 2012;911:355-72. doi: 10.1007/978-1-61779-968-6_21.
Mitraki et al., Amino acid substitutions influencing intracellular protein folding pathways. FEBS Lett. Jul. 27, 1992;307(1):20-5.
Roitt et al., Immunology. 5$^{th}$ edition. Moscow. 2000;110-111.
Saerens et al., Disulfide bond introduction for general stabilization of immunoglobulin heavy-chain variable domains. J Mol Biol. Mar. 21, 2008;377(2):478-88. doi: 10.1016/j.jmb.2008.01.022. Epub Jan. 16, 2008.
Tanha et al., Improving solubility and refolding efficiency of human V(H)s by a novel mutational approach. Protein Eng Des Sel. Nov. 2006;19(11):503-9. Epub Sep. 13, 2006.
Tanha et al., Optimal design features of camelized human single-domain antibody libraries. J Biol Chem. Jul. 6, 2001;276(27):24774-80. Epub May 2, 2001.
To et al., Isolation of monomeric human V(H)s by a phage selection. J Biol Chem. Dec. 16, 2005;280(50):41395-403. Epub Oct. 12, 2005.
Ward et al., Binding activities of a repertoire of single immunoglobulin variable domains secreted from *Escherichia coli*. Nature. Oct. 12, 1989;341(6242):544-6.
Wetzel et al., Disulfide bonds and thermal stability in T4 lysozyme. Proc Natl Acad Sci U S A. Jan. 1988;85(2):401-5.
Williams et al., The immunoglobulin superfamily—domains for cell surface recognition. Annu Rev Immunol. 1988;6:381-405.
Wörn et al., Stability engineering of antibody single-chain Fv fragments. J Mol Biol. Feb. 2, 2001;305(5):989-1010.
Wu et al., Mass spectrometric determination of disulfide linkages in recombinant therapeutic proteins using online LC-MS with electron-transfer dissociation. Anal Chem. Jan. 1, 2009;81(1):112-22. doi: 10.1021/ac801560k.

```
                                          CDR1                        CDR2
                       FR1               (H31-35)      FR2           (H50-65)
                  ------------------------------------ ----- ------------------- -------------------
                       1         2         3           4           5         6
                  12345678901234567890123456789012345  12345 678901234567890     012a3456789012345
HVHAm302          QVQLVESGGGLIKPGGSLRLSCAASGDTVS       DESMT WVRQAPGKGLEWVS      AISSSGGSTYYADSVKG
HVHAm302S         QVQLVESGGGLIKPGGSLRLSCAASGDTVS       DESMT WVRQAPGKGLEWVC      AISSSGGSTYYADSVKG

HVHAm427          QVQLVESGGGLIKPGGSLRLSCAASGVTLS       PECMA WVRQAPGKGLEWVS      AISSSGGSTYYADSVKG
HVHAm427S         QVQLVESGGGLIKPGGSLRLSCAASGVTLS       PECMA WVRQAPGKGLEWVC      AISSSGGSTYYADSVKG

HVHAm431          QVQLVESGGGLIKPGGSLRLSCAASGYTVS       SECMG WVRQAPGKGLEWVS      AISSSGGSTYYADSVKG
HVHAm431S         QVQLVESGGGLIKPGGSLRLSCAASGYTVS       SECMG WVRQAPGKGLEWVC      AISSSGGSTYYADSVKG

HVHPC235          QVQLVESGGGLIKPGGSLRLSCAASGFSVI       SESMT WVRQAPGKGLEWVS      AISSSGGSTYYADSVKG
HVHPC235S         QVQLVESGGGLIKPGGSLRLSCAASGFSVI       SESMT WVRQAPGKGLEWVC      AISSSGGSTYYADSVKG

CDR3
                            FR3                      (H95-102)            FR4
                  ------------------------------ ------------------- -------------
                       7         8         9           10                11
                  6789012345678901234abc345678901234  567890abcdefgh12  34567890123
HVHAm302          RFTISRDNSKNTVYLQMNSLRAEDTAVYYCVT    DNRSCQTSLCTSTTRS  WGQGTMVTVSS
HVHAm302S         RFTCSRDNSKNTVYLQMNSLRAEDTAVYYCVT    DNRSCQTSLCTSTTRS  WGQGTMVTVSS HVHAm427          RFTISRDNSKNTVYLQMNSLRAEDTAVYYCVS    CEGEN---------AF  WGQGTMVTVSS
HVHAm427S         RFTCSRDNSKNTVYLQMNSLRAEDTAVYYCVS    CEGEN---------AF  WGQGTMVTVSS HVHAm431          RFTISRDNSKNTVYLQMNSLRAEDTAVYYCVR    DSKNCHDKDCTRPYCS  WGQGTMVTVSS
HVHAm431S         RFTCSRDNSKNTVYLQMNSLRAEDTAVYYCVR    DSKNCHDKDCTRPYCS  WGQGTMVTVSS HVHPC235          RFTISRDNSKNTVHLQMNSLRADDTAVYYCAA    KKIDGARY------DY  WGQGTMVTVSS
HVHPC235S         RFTCSRDNSKNTVHLQMNSLRADDTAVYYCAA    KKIDGARY------DY  WGQGTMVTVSS
```

FIG. 1A

```
                         CDR1                      CDR2
              FR1        (L24-34)        FR2       (L50-56)
           ----------------------  ----------  -----------------  --------
                    1         2           3            4              5
           1234567890123456789012 3  4567ab8901234  567890123456789  0123456
HVLP324    DIQMTQSPSSLSASVGDRVTITC  RASQ--SISTYLN  WYQQKPGKAPKLLIF  AASTLQS
HVLP324S   DIQMTQSPSSLSASVGDRVTITC  RASQ--SISTYLN  WYQQKPGKAPKLLCF  AASTLQS

HVLP342    DIQMTQSPSSLSASVGDRVTITC  RASQ--DIRTDLD  WFQQRPGRAPHRLIY  GASSLQG
HVLP342S   DIQMTQSPSSLSASVGDRVTITC  RASQ--DIRTDLD  WFQQRPGRAPHRLCY  GASSLQG

HVLP335    EIVMTQSPATLSLSPGERATLSC  RASQS-VSSSSLA  WYQQKPGQAPRLLIY  GTSNRAT
HVLP335S   EIVMTQSPATLSLSPGERATLSC  RASQS-VSSSSLA  WYQQKPGQAPRLLCY  GTSNRAT

HVLP364    ETTLTQSPATLSVSPGERATFSC  RASQ--SVSNNLA  WYQQKPGQAPRLLIY  GASSRTT
HVLP364S   ETTLTQSPATLSVSPGERATFSC  RASQ--SVSNNLA  WYQQKPGQAPRLLCY  GASSRTT

HVLP3103   ETTLTQSPGTLSLSPGERATLSC  RASQ--SVRNNLA  WQQRPGQAPRLLIY   GASTRAT
HVLP3103S  ETTLTQSPGTLSLSPGERATLSC  RASQ--SVRNNLA  WQQRPGQAPRLLCY   GASTRAT

HVLP325    EIVLTQSPTTLSLSPGERATLSC  RASQ--SVGRYLA  WYQQRPGQAPRLLVF  DTSNRAP
HVLP325S   EIVLTQSPTTLSLSPGERATLSC  RASQ--SVGRYLA  WYQQRPGQAPRLLCF  DTSNRAP

HVLP351    EIVMTQSPVTLSLSPGERATLSC  RASQ--SVGTSLA  WYQQKPGQAPRLLIY  DASNRAT
HVLP351S   EIVMTQSPVTLSLSPGERATLSC  RASQ--SVGTSLA  WYQQKPGQAPRLLCY  DASNRAT

HVLP389    QSVVTQPPS-VSAAPGQRVTISC  SGSSYNIGENSVS  WYQQLPGTAPKLLIY  GNDKRPS
HVLP389S   QSVVTQPPS-VSAAPGQRVTISC  SGSSYNIGENSVS  WYQQLPGTAPKLLCY  GNDKRPS

CDR3
                  FR3                   (L89-97)      FR4
           ------------------------------  ----------  -----------
                6         7         8         9           10
           78901234567890123456789012345678  9012345ab67  890123456a
HVLP324    GVPSRFSGSGSGTDFTLTISNLPEDFATYYC  QQSYSTP--RT  FGHGTKVTVL
HVLP324S   GVPSRFSCSGSGTDFTLTISNLPEDFATYYC  QQSYSTP--RT  FGHGTKVTVL

HVLP342    GVPSRFSGSGSGTEFTLTISGLQPEDFATYYC  LQHHTYP--RT  FGLGTKVTVL
HVLP342S   GVPSRFSCSGSGTEFTLTISGLQPEDFATYYC  LQHHTYP--RT  FGLGTKVTVL

HVLP335    GIPDRFSGSGSGTHFTLTINRLEPGDFAVYYC  QQYGSSP--RT  FGQGTKVEIK
HVLP335S   GIPDRFSCSGSGTHFTLTINRLEPGDFAVYYC  QQYGSSP--RT  FGQGTKVEIK

HVLP364    GIPDRFSASGSGTDFTLTISRLEPEDFAVYYC  QQYDTSP--RT  FGQGTKVEIK
HVLP364S   GIPDRFSCSGSGTDFTLTISRLEPEDFAVYYC  QQYDTSP--RT  FGQGTKVEIK

HVLP3103   GIPARFSGSGSGTDFTLTISSLQVEDVAVYYC  QQYYTTP--KT  FGQGTKVEIK
HVLP3103S  GIPARFSCSGSGTDFTLTISSLQVEDVAVYYC  QQYYTTP--KT  FGQGTKVEIK

HVLP325    GVPARFSGRGSGTLFTLTISSLEPEDSAVYFC  QQRSSG---LT  FGGGTKVTVL
HVLP325S   GVPARFSCRGSGTLFTLTISSLEPEDSAVYFC  QQRSSG---LT  FGGGTKVTVL

HVLP351    GISARFSGSGSGTDFTLTISSLEPEDFAVYYC  QQRYNWP--RT  FGGGTKVTVL
HVLP351S   GISARFSCSGSGTDFTLTISSLEPEDFAVYYC  QQRYNWP--RT  FGGGTKVTVL

HVLP389    GIPDRFSGSKSGTSATLGITGLQTGDEADYYC  GTWDSNLRASV  FGGGTKVTVL
HVLP389S   GIPDRFSCSKSGTSATLGITGLQTGDEADYYC  GTWDSNLRASV  FGGGTKVTVL
```

FIG. 1B

```
                      CDR1                        CDR2
         FR1         (24-34)         FR2         (50-56)
---------------------  ---------------  ------------------  --------
         1          2         3              4        •  5
12345678901234567890123 4567ab8901234 567890123456789 0123456
DIQMTQSPSSLSASVGDRVTITC RASQ--SISTYLN WYQQKPGKAPKLLCF AASTLQS
                            *  ****  *                    *  ***

CDR3
         FR3                           (89-97)       FR4
----------------------------------  ------------  -----------
    6    •    7         8               9           10
78901234567890123456789012345678 9012345ab67 890123456a
GVPSRFSCSGSGTDFTLTISNLQPEDFATYYC QQSYSTP--RT FGHGTKVTVL
                                 *  ****  * ***
```

```
                         R   A   S   Q   S   I   S   T   Y   L   N
HVLP324S CDR1           CGG GCA AGT CAG AGC ATT AGC ACC TAT TTA AAT
CDR1 Randomization      NNK             RGC     NNK NNK NNK     NNK A   A   S   T   L   Q   S
HVLP324S CDR2           GCT GCA TCC TGT CTC GCT AGT
CDR2 Randomization      NNK         NNK CKN NNK 95a  95b
                         Q   Q   S   Y   S   T   P        -    -   R   T
HVLP324S CDR3           CAA CAG AGT TAC AGT ACC CCT       -    -  CGG ACG
CDR3 Randomization   ┌─ NNK     NNK NNK NNK NNK                    NNK
                     │  NNK     NNK NNK NNK NNK          NNK       NNK
                     └─ NNK     NNK NNK NNK NNK          NNK  NNK  NNK
```

FIG. 11

```
                             CDR1                        CDR2
                 FR1         (24-34)      FR2            (50-56)
                 ----------- ------------ -------------- -------
                 1         2  3           4              5
                 12345678901234567890123 4567ab8901234 567890123456789 0123456
HVLP324S         DIQMTQSPSSLSASVGDRVTITC RASQ--SISTYLN WYQQKPGKAPKLLCF AASTLQS
HVLHLNN          DIQMTQSPSSLSASVGDRVTITC SASQ--SINNRLY WYQQKPGKAPKLLCF PASFLFS
HVLHLDS          DIQMTQSPSSLSASVGDRVTITC TVSQ--GIDSRLY WYQQKPGKAPKLLCF PASLLES
HVLHLRN          DIQMTQSPSSLSASVGDRVTITC KASQ--GIRNRLY WYQQKPGKAPKLLCF PASILDS
HVLHLNE          DIQMTQSPSSLSASVGDRVTITC DASQ--SINERLY WYQQKPGKAPKLLCF PASILTS
HVLHLAQ          DIQMTQSPSSLSASVGDRVTITC GASQ--SIAQRLY WYQQKPGKAPKLLCF PASLLHS
HVLHLEM          DIQMTQSPSSLSASVGDRVTITC QASQ--GIEMFLQ WYQQKPGKAPKLLCF AASTLQS
HVLHLQI          DIQMTQSPSSLSASVGDRVTITC RASQ--SIQIMLD WYQQKPGKAPKLLCF GASFLIS
HVLHLYS          DIQMTQSPSSLSASVGDRVTITC QASQ--SIYSKLY WYQQKPGKAPKLLCF PASLLWS
HVLHSA1          DIQMTQSPSSLSASVGDRVTITC RASQ--SISTYLN WYQQKPGKAPKLLCF GASRLNS

CDR3
                 FR3                          (89-97)       FR4
                 ---------------------------- ------------- ------------
                 6         7         8         9            10
                 7890123456789012345678901234 5678 9012345ab67 8901234567
HVLP324S         GVPSRFCGSGSGTDFTLTISNLQPEDFATYYC QQSYSTP--RT FGHGTKVTVL
HVLHLNN          GVPSRFCGSGSGTDFTLTISNLQPEDFATYYC QQSYSTP--RT FGHGTKVTVL
HVLHLDS          GVPSRFCGSGSGTDFTLTISNLQPEDFATYYC QQSYSTP--RT FGHGTKVTVL
HVLHLRN          GVPSRFCGSGSGTDFTLTISNLQPEDFATYYC AQQPGLPNSRT FGHGTKVTVL
HVLHLNE          GVPSRFCGSGSGTDFTLTISNLQPEDFATYYC RQPRSGP--ST FGHGTKVTVL
HVLHLAQ          GVPSRFCGSGSGTDFTLTISNLQPEDFATYYC AQRASPPR-PT FGHGTKVTVL
HVLHLEM          GVPSRFCGSGSGTDFTLTISNLQPEDFATYYC VQPGVAPPPGT FGHGTKVTVL
HVLHLQI          GVPSRFCGSGSGTDFTLTISNLQPEDFATYYC RQTWTPPA-PT FGHGTKVTVL
HVLHLYS          GVPSRFCGSGSGTDFTLTISNLQPEDFATYYC IQNAADPH-RT FGHGTKVRL-
HVLHSA1          GVPSRFCGSGSGTDFTLTISNLQPEDFATYYC RQLFPLPDRRT FGHGTKVTVL
```

FIG. 13

SEQUENCE LISTING

```
<160> NUMBER OF SEQ ID NOS: 108

<210> SEQ ID NO 1
<211> LENGTH: 125
<212> TYPE: PRT
<213> ORGANISM: Artificial Sequence
<220> FEATURE:
<223> OTHER INFORMATION: Human - HVHAm302

<400> SEQUENCE: 1

Gln Val Gln Leu Val Glu Ser Gly Gly Gly Leu Ile Lys Pro Gly Gly
1               5                   10                  15

Ser Leu Arg Leu Ser Cys Ala Ala Ser Gly Asp Thr Val Ser Asp Glu
            20                  25                  30

Ser Met Thr Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Thr Asp Asn Arg Ser Cys Gln Thr Ser Leu Cys Thr Ser Thr Thr
            100                 105                 110

Arg Ser Trp Gly Gln Gly Thr Met Val Thr Val Ser Ser
        115                 120                 125

<210> SEQ ID NO 2
<211> LENGTH: 125
<212> TYPE: PRT
<213> ORGANISM: Artificial Sequence
<220> FEATURE:
<223> OTHER INFORMATION: Human - HVHAm302S

<400> SEQUENCE: 2

Gln Val Gln Leu Val Glu Ser Gly Gly Gly Leu Ile Lys Pro Gly Gly
1               5                   10                  15

Ser Leu Arg Leu Ser Cys Ala Ala Ser Gly Asp Thr Val Ser Asp Glu
            20                  25                  30

Ser Met Thr Trp Val Arg Gln Ala Pro Gly Lys Gly Leu Glu Trp Val
        35                  40                  45

Cys Ala Ile Ser Ser Ser Gly Gly Ser Thr Tyr Tyr Ala Asp Ser Val
    50                  55                  60

Lys Gly Arg Phe Thr Cys Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Thr Asp Asn Arg Ser Cys Gln Thr Ser Leu Cys Thr Ser Thr Thr
            100                 105                 110
```

```
Arg Ser Trp Gly Gln Gly Thr Met Val Thr Val Ser Ser
        115                 120                 125

<210> SEQ ID NO 3
<211> LENGTH: 116
<212> TYPE: PRT
<213> ORGANISM: Artificial Sequence
<220> FEATURE:
<223> OTHER INFORMATION: Human - HVHAm427

<400> SEQUENCE: 3

Gln Val Gln Leu Val Glu Ser Gly Gly Gly Leu Ile Lys Pro Gly Gly
1               5                   10                  15

Ser Leu Arg Leu Ser Cys Ala Ala Ser Gly Val Thr Leu Ser Pro Glu
            20                  25                  30

Cys Met Ala Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Ser Cys Glu Gly Glu Asn Ala Phe Trp Gly Gln Gly Thr Met Val
                100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: Human - HVHAm427S

<400> SEQUENCE: 4

Gln Val Gln Leu Val Glu Ser Gly Gly Gly Leu Ile Lys Pro Gly Gly
1               5                   10                  15

Ser Leu Arg Leu Ser Cys Ala Ala Ser Gly Val Thr Leu Ser Pro Glu
            20                  25                  30

Cys Met Ala Trp Val Arg Gln Ala Pro Gly Lys Gly Leu Glu Trp Val
        35                  40                  45

Cys Ala Ile Ser Ser Ser Gly Gly Ser Thr Tyr Tyr Ala Asp Ser Val
    50                  55                  60

Lys Gly Arg Phe Thr Cys Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Ser Cys Glu Gly Glu Asn Ala Phe Trp Gly Gln Gly Thr Met Val
                100                 105                 110

Thr Val Ser Ser
        115

<210> SEQ ID NO 5
<211> LENGTH: 125
<212> TYPE: PRT
<213> ORGANISM: Artificial Sequence
<220> FEATURE:
<223> OTHER INFORMATION: Human - HVHAm431
```

<400> SEQUENCE: 5

```
Gln Val Gln Leu Val Glu Ser Gly Gly Gly Leu Ile Lys Pro Gly Gly
1               5                   10                  15

Ser Leu Arg Leu Ser Cys Ala Ala Ser Gly Tyr Thr Val Ser Ser Glu
            20                  25                  30

Cys Met Gly Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Arg Asp Ser Lys Asn Cys His Asp Lys Asp Cys Thr Arg Pro Tyr
            100                 105                 110

Cys Ser Trp Gly Gln Gly Thr Met Val Thr Val Ser Ser
        115                 120                 125
```

<210> SEQ ID NO 6
<211> LENGTH: 125
<212> TYPE: PRT
<213> ORGANISM: Artificial Sequence
<220> FEATURE:
<223> OTHER INFORMATION: Human - HVHAm431S

<400> SEQUENCE: 6

```
Gln Val Gln Leu Val Glu Ser Gly Gly Gly Leu Ile Lys Pro Gly Gly
1               5                   10                  15

Ser Leu Arg Leu Ser Cys Ala Ala Ser Gly Tyr Thr Val Ser Ser Glu
            20                  25                  30

Cys Met Gly Trp Val Arg Gln Ala Pro Gly Lys Gly Leu Glu Trp Val
        35                  40                  45

Cys Ala Ile Ser Ser Ser Gly Ser Thr Tyr Tyr Ala Asp Ser Val
    50                  55                  60

Lys Gly Arg Phe Thr Cys Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Arg Asp Ser Lys Asn Cys His Asp Lys Asp Cys Thr Arg Pro Tyr
            100                 105                 110

Cys Ser Trp Gly Gln Gly Thr Met Val Thr Val Ser Ser
        115                 120                 125
```

<210> SEQ ID NO 7
<211> LENGTH: 119
<212> TYPE: PRT
<213> ORGANISM: Artificial Sequence
<220> FEATURE:
<223> OTHER INFORMATION: Human - HVHPC235

<400> SEQUENCE: 7

```
Gln Val Gln Leu Val Glu Ser Gly Gly Gly Leu Ile Lys Pro Gly Gly
1               5                   10                  15

Ser Leu Arg Leu Ser Cys Ala Ala Ser Gly Phe Ser Val Ile Ser Glu
            20                  25                  30

Ser Met Thr Trp Val Arg Gln Ala Pro Gly Lys Gly Leu Glu Trp Val
        35                  40                  45
```

```
Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Val His
65                  70                  75                  80

Leu Gln Met Asn Ser Leu Arg Ala Asp Asp Thr Ala Val Tyr Tyr Cys
                85                  90                  95

Ala Ala Lys Lys Ile Asp Gly Ala Arg Tyr Asp Tyr Trp Gly Gln Gly
                100                 105                 110

Thr Met Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: Human - HVHPC235S

<400> SEQUENCE: 8

Gln Val Gln Leu Val Glu Ser Gly Gly Gly Leu Ile Lys Pro Gly Gly
1               5                   10                  15

Ser Leu Arg Leu Ser Cys Ala Ala Ser Gly Phe Ser Val Ile Ser Glu
            20                  25                  30

Ser Met Thr Trp Val Arg Gln Ala Pro Gly Lys Gly Leu Glu Trp Val
        35                  40                  45

Cys Ala Ile Ser Ser Ser Gly Gly Ser Thr Tyr Tyr Ala Asp Ser Val
    50                  55                  60

Lys Gly Arg Phe Thr Cys Ser Arg Asp Asn Ser Lys Asn Thr Val His
65                  70                  75                  80

Leu Gln Met Asn Ser Leu Arg Ala Glu Asp Thr Ala Val Tyr Tyr Cys
                85                  90                  95

Ala Ala Lys Lys Ile Asp Gly Ala Arg Tyr Asp Tyr Trp Gly Gln Gly
                100                 105                 110

Thr Met Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Human - HVLP324

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Phe Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly His Gly Thr Lys Val Thr Val Leu
                100                 105
```

<210> SEQ ID NO 10
<211> LENGTH: 107
<212> TYPE: PRT
<213> ORGANISM: Artificial Sequence
<220> FEATURE:
<223> OTHER INFORMATION: Human - HVLP324S

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Cys
        35                  40                  45

Phe Ala Ala Ser Thr Leu Gln Ser Gly Val Pro Ser Arg Phe Ser Cys
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly His Gly Thr Lys Val Thr Val Leu
            100                 105
```

<210> SEQ ID NO 11
<211> LENGTH: 106
<212> TYPE: PRT
<213> ORGANISM: Artificial Sequence
<220> FEATURE:
<223> OTHER INFORMATION: Human - HVLP325

<400> SEQUENCE: 11

```
Glu Ile Val Leu Thr Gln Ser Pro Thr Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Leu Ala Trp Tyr Gln Gln Arg Pro Gly Gln Ala Pro Arg Leu Leu Val
        35                  40                  45

Phe Asp Thr Ser Asn Arg Ala Pro Gly Val Pro Ala Arg Phe Ser Gly
    50                  55                  60

Arg Gly Ser Gly Thr Leu Phe Thr Leu Thr Ile Ser Ser Leu Glu Pro
65                  70                  75                  80

Glu Asp Ser Ala Val Tyr Phe Cys Gln Gln Arg Ser Ser Gly Leu Thr
                85                  90                  95

Phe Gly Gly Gly Thr Lys Val Thr Val Leu
            100                 105
```

<210> SEQ ID NO 12
<211> LENGTH: 106
<212> TYPE: PRT
<213> ORGANISM: Artificial Sequence
<220> FEATURE:
<223> OTHER INFORMATION: Human - HVLP325S

<400> SEQUENCE: 12

```
Glu Ile Val Leu Thr Gln Ser Pro Thr Thr Leu Ser Leu Ser Pro Gly
1               5                   10                  15

Glu Arg Ala Thr Leu Ser Cys Arg Ala Ser Gln Ser Val Gly Arg Tyr
            20                  25                  30
```

-continued

Leu Ala Trp Tyr Gln Gln Arg Pro Gly Gln Ala Pro Arg Leu Leu Cys
        35                  40                  45

Phe Asp Thr Ser Asn Arg Ala Pro Gly Val Pro Ala Arg Phe Ser Cys
 50                  55                  60

Arg Gly Ser Gly Thr Leu Phe Thr Leu Thr Ile Ser Ser Leu Glu Pro
 65                  70                  75                  80

Glu Asp Ser Ala Val Tyr Phe Cys Gln Gln Arg Ser Ser Gly Leu Thr
                 85                  90                  95

Phe Gly Gly Gly Thr Lys Val Thr Val Leu
            100                 105

<210> SEQ ID NO 13
<211> LENGTH: 108
<212> TYPE: PRT
<213> ORGANISM: Artificial Sequence
<220> FEATURE:
<223> OTHER INFORMATION: Human - HVLP335

<400> SEQUENCE: 13

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Asn Arg Ala Thr Gly Ile Pro Asp Arg Phe Ser
 50                  55                  60

Gly Ser Gly Ser Gly Thr His Phe Thr Leu Thr Ile Asn Arg Leu Glu
 65                  70                  75                  80

Pro Gly Asp Phe Ala Val Tyr Tyr Cys Gln Gln Tyr Gly Ser Ser Pro
                 85                  90                  95

Arg Thr Phe Gly Gln Gly Thr Lys Val Glu Ile Lys
            100                 105

<210> SEQ ID NO 14
<211> LENGTH: 108
<212> TYPE: PRT
<213> ORGANISM: Artificial Sequence
<220> FEATURE:
<223> OTHER INFORMATION: Human - HVLP335S

<400> SEQUENCE: 14

Glu Ile Val Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Cys Tyr Gly Thr Ser Asn Arg Ala Thr Gly Ile Pro Asp Arg Phe Ser
 50                  55                  60

Cys Ser Gly Ser Gly Thr His Phe Thr Leu Thr Ile Asn Arg Leu Glu
 65                  70                  75                  80

Pro Gly Asp Phe Ala Val Tyr Tyr Cys Gln Gln Tyr Gly Ser Ser Pro
                 85                  90                  95

Arg Thr Phe Gly Gln Gly Thr Lys Val Glu Ile Lys
            100                 105

-continued

<210> SEQ ID NO 15
<211> LENGTH: 107
<212> TYPE: PRT
<213> ORGANISM: Artificial Sequence
<220> FEATURE:
<223> OTHER INFORMATION: Human - HVLP342

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Thr Asp
            20                  25                  30

Leu Asp Trp Phe Gln Gln Arg Pro Gly Arg Ala Pro His Arg Leu Ile
        35                  40                  45

Tyr Gly Ala Ser Ser Leu Gln Gly Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His His Thr Tyr Pro Arg
                85                  90                  95

Thr Phe Gly Leu Gly Thr Lys Val Thr Val Leu
            100                 105

<210> SEQ ID NO 16
<211> LENGTH: 107
<212> TYPE: PRT
<213> ORGANISM: Artificial Sequence
<220> FEATURE:
<223> OTHER INFORMATION: Human - HVLP342S

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Thr Asp
            20                  25                  30

Leu Asp Trp Phe Gln Gln Arg Pro Gly Arg Ala Pro His Arg Leu Cys
        35                  40                  45

Tyr Gly Ala Ser Ser Leu Gln Gly Gly Val Pro Ser Arg Phe Ser Cys
    50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Leu Gln His His Thr Tyr Pro Arg
                85                  90                  95

Thr Phe Gly Leu Gly Thr Lys Val Thr Val Leu
            100                 105

<210> SEQ ID NO 17
<211> LENGTH: 107
<212> TYPE: PRT
<213> ORGANISM: Artificial Sequence
<220> FEATURE:
<223> OTHER INFORMATION: Human - HVLP351

<400> SEQUENCE: 17

Glu Ile Val Met Thr Gln Ser Pro Val Thr Leu Ser Leu Ser Pro Gly
1               5                   10                  15

Glu Arg Ala Thr Leu Ser Cys Arg Ala Ser Gln Ser Val Gly Thr Ser
            20                  25                  30

Leu Ala Trp Tyr Gln Gln Lys Pro Gly Gln Ala Pro Arg Leu Leu Ile
        35                  40                  45

-continued

```
Tyr Asp Ala Ser Asn Arg Ala Thr Gly Ile Ser Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Tyr Asn Trp Pro Arg
                 85                  90                  95

Thr Phe Gly Gly Gly Thr Lys Val Thr Val Leu
            100                 105

<210> SEQ ID NO 18
<211> LENGTH: 107
<212> TYPE: PRT
<213> ORGANISM: Artificial Sequence
<220> FEATURE:
<223> OTHER INFORMATION: Human - HVLP351S

<400> SEQUENCE: 18

Glu Ile Val Met Thr Gln Ser Pro Val Thr Leu Ser Leu Ser Pro Gly
 1               5                  10                  15

Glu Arg Ala Thr Leu Ser Cys Arg Ala Ser Gln Ser Val Gly Thr Ser
                 20                  25                  30

Leu Ala Trp Tyr Gln Gln Lys Pro Gly Gln Ala Pro Arg Leu Leu Cys
             35                  40                  45

Tyr Asp Ala Ser Asn Arg Ala Thr Gly Ile Ser Ala Arg Phe Ser Cys
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Tyr Asn Trp Pro Arg
                 85                  90                  95

Thr Phe Gly Gly Gly Thr Lys Val Thr Val Leu
            100                 105

<210> SEQ ID NO 19
<211> LENGTH: 107
<212> TYPE: PRT
<213> ORGANISM: Artificial Sequence
<220> FEATURE:
<223> OTHER INFORMATION: Human - HVLP364

<400> SEQUENCE: 19

Glu Thr Thr Leu Thr Gln Ser Pro Ala Thr Leu Ser Val Ser Pro Gly
 1               5                  10                  15

Glu Arg Ala Thr Phe Ser Cys Arg Ala Ser Gln Ser Val Ser Asn Asn
                 20                  25                  30

Leu Ala Trp Tyr Gln Gln Lys Pro Gly Gln Ala Pro Arg Leu Leu Ile
             35                  40                  45

Tyr Gly Ala Ser Ser Arg Thr Thr Gly Ile Pro Asp Arg Phe Ser Ala
         50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Asp Thr Ser Pro Arg
                 85                  90                  95

Thr Phe Gly Gln Gly Thr Lys Val Glu Ile Lys
            100                 105

<210> SEQ ID NO 20
<211> LENGTH: 107
<212> TYPE: PRT
```

<213> ORGANISM: Artificial Sequence
<220> FEATURE:
<223> OTHER INFORMATION: Human - HVLP364S

<400> SEQUENCE: 20

Glu Thr Thr Leu Thr Gln Ser Pro Ala Thr Leu Ser Val Ser Pro Gly
1               5                   10                  15

Glu Arg Ala Thr Phe Ser Cys Arg Ala Ser Gln Ser Val Ser Asn Asn
            20                  25                  30

Leu Ala Trp Tyr Gln Gln Lys Pro Gly Gln Ala Pro Arg Leu Leu Cys
        35                  40                  45

Tyr Gly Ala Ser Ser Arg Thr Thr Gly Ile Pro Asp Arg Phe Ser Cys
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Thr Ser Pro Arg
                85                  90                  95

Thr Phe Gly Gln Gly Thr Lys Val Glu Ile Lys
            100                 105

<210> SEQ ID NO 21
<211> LENGTH: 110
<212> TYPE: PRT
<213> ORGANISM: Artificial Sequence
<220> FEATURE:
<223> OTHER INFORMATION: Human - HVLP389

<400> SEQUENCE: 21

Gln Ser Val Val Thr Gln Pro Pro Ser Val Ser Ala Ala Pro Gly Gln
1               5                   10                  15

Arg Val Thr Ile Ser Cys Ser Gly Ser Ser Tyr Asn Ile Gly Glu Asn
            20                  25                  30

Ser Val Ser Trp Tyr Gln Gln Leu Pro Gly Thr Ala Pro Lys Leu Leu
        35                  40                  45

Ile Tyr Gly Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Asn Leu
                85                  90                  95

Arg Ala Ser Val Phe Gly Gly Gly Thr Lys Val Thr Val Leu
            100                 105                 110

<210> SEQ ID NO 22
<211> LENGTH: 110
<212> TYPE: PRT
<213> ORGANISM: Artificial Sequence
<220> FEATURE:
<223> OTHER INFORMATION: Human - HVLP389S

<400> SEQUENCE: 22

Gln Ser Val Val Thr Gln Pro Pro Ser Val Ser Ala Ala Pro Gly Gln
1               5                   10                  15

Arg Val Thr Ile Ser Cys Ser Gly Ser Ser Tyr Asn Ile Gly Glu Asn
            20                  25                  30

Ser Val Ser Trp Tyr Gln Gln Leu Pro Gly Thr Ala Pro Lys Leu Leu
        35                  40                  45

Cys Tyr Gly Asn Asp Lys Arg Pro Ser Gly Ile Pro Asp Arg Phe Ser
    50                  55                  60

-continued

Cys Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Asn Leu
             85                  90                  95

Arg Ala Ser Val Phe Gly Gly Gly Thr Lys Val Thr Val Leu
            100                 105                 110

<210> SEQ ID NO 23
<211> LENGTH: 107
<212> TYPE: PRT
<213> ORGANISM: Artificial Sequence
<220> FEATURE:
<223> OTHER INFORMATION: Human - HVLP3103

<400> SEQUENCE: 23

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Asn Asn
            20                  25                  30

Leu Ala Trp Tyr Gln Gln Arg Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Asp Phe Thr Leu Thr Ile Ser Ser Leu Gln Val
 65                  70                  75                  80

Glu Asp Val Ala Val Tyr Tyr Cys Gln Gln Tyr Tyr Thr Thr Pro Lys
             85                  90                  95

Thr Phe Gly Gln Gly Thr Lys Val Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Human - HVLP3103S

<400> SEQUENCE: 24

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Arg Asn Asn
            20                  25                  30

Leu Ala Trp Tyr Gln Gln Arg Pro Gly Gln Ala Pro Arg Leu Leu Cys
        35                  40                  45

Tyr Gly Ala Ser Thr Arg Ala Thr Gly Ile Pro Ala Arg Phe Ser Cys
 50                  55                  60

Ser Gly Ser Gly Thr Asp Phe Thr Leu Thr Ile Ser Ser Leu Gln Val
 65                  70                  75                  80

Glu Asp Val Ala Val Tyr Tyr Cys Gln Gln Tyr Tyr Thr Thr Pro Lys
             85                  90                  95

Thr Phe Gly Gln Gly Thr Lys Val Glu Ile Lys
            100                 105

<210> SEQ ID NO 25
<211> LENGTH: 12
<212> TYPE: PRT
<213> ORGANISM: Artificial Sequence
<220> FEATURE:
<223> OTHER INFORMATION: tryptic peptide

<400> SEQUENCE: 25

Ser Cys Gln Thr Ser Leu Cys Thr Ser Thr Thr Arg
1               5                   10

<210> SEQ ID NO 26
<211> LENGTH: 19
<212> TYPE: PRT
<213> ORGANISM: Artificial Sequence
<220> FEATURE:
<223> OTHER INFORMATION: tryptic peptide

<400> SEQUENCE: 26

Leu Ser Cys Ala Ala Ser Gly Asp Thr Val Ser Asp Glu Ser Met Thr
1               5                   10                  15

Trp Val Arg

<210> SEQ ID NO 27
<211> LENGTH: 14
<212> TYPE: PRT
<213> ORGANISM: Artificial Sequence
<220> FEATURE:
<223> OTHER INFORMATION: tryptic peptide

<400> SEQUENCE: 27

Ala Glu Asp Thr Ala Val Tyr Tyr Cys Val Thr Asp Asn Arg
1               5                   10

<210> SEQ ID NO 28
<211> LENGTH: 12
<212> TYPE: PRT
<213> ORGANISM: Artificial Sequence
<220> FEATURE:
<223> OTHER INFORMATION: tryptic peptide

<400> SEQUENCE: 28

Ser Cys Gln Thr Ser Leu Cys Thr Ser Thr Thr Arg
1               5                   10

<210> SEQ ID NO 29
<211> LENGTH: 22
<212> TYPE: PRT
<213> ORGANISM: Artificial Sequence
<220> FEATURE:
<223> OTHER INFORMATION: tryptic peptide

<400> SEQUENCE: 29

Gly Leu Glu Trp Val Cys Ala Ile Ser Ser Gly Gly Ser Thr Tyr
1               5                   10                  15

Tyr Ala Asp Ser Val Lys
            20

<210> SEQ ID NO 30
<211> LENGTH: 5
<212> TYPE: PRT
<213> ORGANISM: Artificial Sequence
<220> FEATURE:
<223> OTHER INFORMATION: tryptic peptide

<400> SEQUENCE: 30

Phe Thr Cys Ser Arg
1               5

<210> SEQ ID NO 31
<211> LENGTH: 19

```
<212> TYPE: PRT
<213> ORGANISM: Artificial Sequence
<220> FEATURE:
<223> OTHER INFORMATION: tryptic peptide

<400> SEQUENCE: 31

Leu Ser Cys Ala Ala Ser Gly Asp Thr Val Ser Asp Glu Ser Met Thr
1               5                   10                  15

Trp Val Arg

<210> SEQ ID NO 32
<211> LENGTH: 14
<212> TYPE: PRT
<213> ORGANISM: Artificial Sequence
<220> FEATURE:
<223> OTHER INFORMATION: tryptic peptide

<400> SEQUENCE: 32

Ala Glu Asp Thr Ala Val Tyr Tyr Cys Val Thr Asp Asn Arg
1               5                   10

<210> SEQ ID NO 33
<211> LENGTH: 22
<212> TYPE: PRT
<213> ORGANISM: Artificial Sequence
<220> FEATURE:
<223> OTHER INFORMATION: tryptic peptide

<400> SEQUENCE: 33

Gly Leu Glu Trp Val Cys Ala Ile Ser Ser Ser Gly Gly Ser Thr Tyr
1               5                   10                  15

Tyr Ala Asp Ser Val Lys
            20

<210> SEQ ID NO 34
<211> LENGTH: 5
<212> TYPE: PRT
<213> ORGANISM: Artificial Sequence
<220> FEATURE:
<223> OTHER INFORMATION: tryptic peptide

<400> SEQUENCE: 34

Phe Thr Cys Ser Arg
1               5

<210> SEQ ID NO 35
<211> LENGTH: 19
<212> TYPE: PRT
<213> ORGANISM: Artificial Sequence
<220> FEATURE:
<223> OTHER INFORMATION: tryptic peptide

<400> SEQUENCE: 35

Leu Ser Cys Ala Ala Ser Gly Phe Ser Val Ile Ser Glu Ser Met Thr
1               5                   10                  15

Trp Val Arg

<210> SEQ ID NO 36
<211> LENGTH: 12
<212> TYPE: PRT
<213> ORGANISM: Artificial Sequence
<220> FEATURE:
<223> OTHER INFORMATION: tryptic peptide

<400> SEQUENCE: 36
```

```
Ala Glu Asp Thr Ala Val Tyr Tyr Cys Ala Ala Lys
1               5                   10
```

<210> SEQ ID NO 37
<211> LENGTH: 22
<212> TYPE: DNA
<213> ORGANISM: Artificial Sequence
<220> FEATURE:
<223> OTHER INFORMATION: Human - M13RPa

<400> SEQUENCE: 37
tcacacagga aacagctatg ac                                         22

<210> SEQ ID NO 38
<211> LENGTH: 40
<212> TYPE: DNA
<213> ORGANISM: Artificial Sequence
<220> FEATURE:
<223> OTHER INFORMATION: Human - KT131

<400> SEQUENCE: 38
accactacta ctaatagcgc agacccactc cagcccttc                        40

<210> SEQ ID NO 39
<211> LENGTH: 24
<212> TYPE: DNA
<213> ORGANISM: Artificial Sequence
<220> FEATURE:
<223> OTHER INFORMATION: Human - M13FP

<400> SEQUENCE: 39
cgccagggtt ttcccagtca cgac                                       24

<210> SEQ ID NO 40
<211> LENGTH: 51
<212> TYPE: DNA
<213> ORGANISM: Artificial Sequence
<220> FEATURE:
<223> OTHER INFORMATION: Human - KT129

<400> SEQUENCE: 40
gcagactccg tgaagggccg attcacctgc tccagagaca attccaagaa c          51

<210> SEQ ID NO 41
<211> LENGTH: 56
<212> TYPE: DNA
<213> ORGANISM: Artificial Sequence
<220> FEATURE:
<223> OTHER INFORMATION: Human - KT130

<400> SEQUENCE: 41
tgcgctatta gtagtagtgg tggtagcaca tactacgcag actccgtgaa gggccg     56

<210> SEQ ID NO 42
<211> LENGTH: 6
<212> TYPE: PRT
<213> ORGANISM: Artificial Sequence
<220> FEATURE:
<223> OTHER INFORMATION: tryptic peptide

<400> SEQUENCE: 42

```
Val Thr Ile Thr Cys Arg
1               5
```

<210> SEQ ID NO 43
<211> LENGTH: 15

<212> TYPE: PRT
<213> ORGANISM: Artificial Sequence
<220> FEATURE:
<223> OTHER INFORMATION: tryptic peptide

<400> SEQUENCE: 43

Leu Leu Cys Phe Ala Ser Thr Leu Gln Ser Gly Val Pro Ser Arg
1               5                   10                  15

<210> SEQ ID NO 44
<211> LENGTH: 34
<212> TYPE: PRT
<213> ORGANISM: Artificial Sequence
<220> FEATURE:
<223> OTHER INFORMATION: tryptic peptide

<400> SEQUENCE: 44

Phe Ser Cys Ser Gly Ser Gly Thr Asp Phe Thr Leu Thr Ile Ser Asn
1               5                   10                  15

Gln Pro Glu Asp Phe Ala Thr Tyr Tyr Cys Gln Gln Ser Tyr Ser Thr
            20                  25                  30

Pro Arg

<210> SEQ ID NO 45
<211> LENGTH: 6
<212> TYPE: PRT
<213> ORGANISM: Artificial Sequence
<220> FEATURE:
<223> OTHER INFORMATION: tryptic peptide

<400> SEQUENCE: 45

Ala Thr Leu Ser Cys Arg
1               5

<210> SEQ ID NO 46
<211> LENGTH: 26
<212> TYPE: PRT
<213> ORGANISM: Artificial Sequence
<220> FEATURE:
<223> OTHER INFORMATION: tryptic peptide

<400> SEQUENCE: 46

Gly Ser Gly Thr Leu Phe Thr Leu Thr Ile Ser Ser Leu Glu Pro Glu
1               5                   10                  15

Asp Ser Ala Val Tyr Phe Cys Gln Gln Arg
            20                  25

<210> SEQ ID NO 47
<211> LENGTH: 9
<212> TYPE: PRT
<213> ORGANISM: Artificial Sequence
<220> FEATURE:
<223> OTHER INFORMATION: tryptic peptide

<400> SEQUENCE: 47

Leu Leu Cys Phe Asp Thr Ser Asn Arg
1               5

<210> SEQ ID NO 48
<211> LENGTH: 4
<212> TYPE: PRT
<213> ORGANISM: Artificial Sequence
<220> FEATURE:
<223> OTHER INFORMATION: tryptic peptide

```
<400> SEQUENCE: 48

Phe Ser Cys Arg
1

<210> SEQ ID NO 49
<211> LENGTH: 9
<212> TYPE: PRT
<213> ORGANISM: Artificial Sequence
<220> FEATURE:
<223> OTHER INFORMATION: tryptic peptide

<400> SEQUENCE: 49

Leu Leu Cys Tyr Gly Thr Ser Asn Arg
1               5

<210> SEQ ID NO 50
<211> LENGTH: 16
<212> TYPE: PRT
<213> ORGANISM: Artificial Sequence
<220> FEATURE:
<223> OTHER INFORMATION: tryptic peptide

<400> SEQUENCE: 50

Phe Ser Cys Ser Gly Ser Gly Thr His Phe Thr Leu Thr Ile Val Arg
1               5                   10                  15

<210> SEQ ID NO 51
<211> LENGTH: 6
<212> TYPE: PRT
<213> ORGANISM: Artificial Sequence
<220> FEATURE:
<223> OTHER INFORMATION: tryptic peptide

<400> SEQUENCE: 51

Ala Thr Leu Ser Cys Arg
1               5

<210> SEQ ID NO 52
<211> LENGTH: 19
<212> TYPE: PRT
<213> ORGANISM: Artificial Sequence
<220> FEATURE:
<223> OTHER INFORMATION: tryptic peptide

<400> SEQUENCE: 52

Leu Glu Pro Gly Asp Phe Ala Val Tyr Tyr Cys Gln Gln Tyr Gly Ser
1               5                   10                  15

Ser Pro Arg

<210> SEQ ID NO 53
<211> LENGTH: 6
<212> TYPE: PRT
<213> ORGANISM: Artificial Sequence
<220> FEATURE:
<223> OTHER INFORMATION: tryptic peptide

<400> SEQUENCE: 53

Val Thr Ile Thr Cys Arg
1               5

<210> SEQ ID NO 54
<211> LENGTH: 15
<212> TYPE: PRT
<213> ORGANISM: Artificial Sequence
<220> FEATURE:
<223> OTHER INFORMATION: tryptic peptide
```

<400> SEQUENCE: 54

Leu Cys Tyr Gly Ala Ser Ser Leu Gln Gly Gly Val Pro Ser Arg
1               5                   10                  15

<210> SEQ ID NO 55
<211> LENGTH: 35
<212> TYPE: PRT
<213> ORGANISM: Artificial Sequence
<220> FEATURE:
<223> OTHER INFORMATION: tryptic peptide

<400> SEQUENCE: 55

Phe Ser Cys Ser Gly Ser Gly Thr Glu Phe Thr Leu Thr Ile Ser Gly
1               5                   10                  15

Leu Gln Pro Glu Asp Phe Ala Thr Tyr Tyr Cys Leu Gln His His Thr
            20                  25                  30

Tyr Pro Arg
        35

<210> SEQ ID NO 56
<211> LENGTH: 6
<212> TYPE: PRT
<213> ORGANISM: Artificial Sequence
<220> FEATURE:
<223> OTHER INFORMATION: tryptic peptide

<400> SEQUENCE: 56

Ala Thr Leu Ser Cys Arg
1               5

<210> SEQ ID NO 57
<211> LENGTH: 9
<212> TYPE: PRT
<213> ORGANISM: Artificial Sequence
<220> FEATURE:
<223> OTHER INFORMATION: tryptic peptide

<400> SEQUENCE: 57

Leu Leu Cys Tyr Asp Ala Ser Asn Arg
1               5

<210> SEQ ID NO 58
<211> LENGTH: 30
<212> TYPE: PRT
<213> ORGANISM: Artificial Sequence
<220> FEATURE:
<223> OTHER INFORMATION: tryptic peptide

<400> SEQUENCE: 58

Phe Ser Cys Ser Gly Ser Gly Thr Asp Phe Thr Leu Thr Ile Ser Ser
1               5                   10                  15

Leu Glu Pro Glu Asp Phe Ala Val Tyr Tyr Cys Gln Gln Arg
            20                  25                  30

<210> SEQ ID NO 59
<211> LENGTH: 11
<212> TYPE: PRT
<213> ORGANISM: Artificial Sequence
<220> FEATURE:
<223> OTHER INFORMATION: tryptic peptide

<400> SEQUENCE: 59

Leu Leu Cys Tyr Gly Ala Ser Ser Arg Thr Arg
1               5                   10

<210> SEQ ID NO 60
<211> LENGTH: 16
<212> TYPE: PRT
<213> ORGANISM: Artificial Sequence
<220> FEATURE:
<223> OTHER INFORMATION: tryptic peptide

<400> SEQUENCE: 60

Phe Ser Cys Ser Gly Ser Gly Thr Asp Phe Thr Leu Thr Ile Ser Arg
1               5                   10                  15

<210> SEQ ID NO 61
<211> LENGTH: 6
<212> TYPE: PRT
<213> ORGANISM: Artificial Sequence
<220> FEATURE:
<223> OTHER INFORMATION: tryptic peptide

<400> SEQUENCE: 61

Ala Thr Phe Ser Cys Arg
1               5

<210> SEQ ID NO 62
<211> LENGTH: 19
<212> TYPE: PRT
<213> ORGANISM: Artificial Sequence
<220> FEATURE:
<223> OTHER INFORMATION: tryptic peptide

<400> SEQUENCE: 62

Leu Glu Pro Glu Asp Phe Ala Val Tyr Tyr Cys Gln Gln Tyr Asp Thr
1               5                   10                  15

Ser Pro Arg

<210> SEQ ID NO 63
<211> LENGTH: 8
<212> TYPE: PRT
<213> ORGANISM: Artificial Sequence
<220> FEATURE:
<223> OTHER INFORMATION: tryptic peptide

<400> SEQUENCE: 63

Leu Leu Cys Tyr Gly Asn Asp Lys
1               5

<210> SEQ ID NO 64
<211> LENGTH: 5
<212> TYPE: PRT
<213> ORGANISM: Artificial Sequence
<220> FEATURE:
<223> OTHER INFORMATION: tryptic peptide

<400> SEQUENCE: 64

Phe Ser Cys Ser Lys
1               5

<210> SEQ ID NO 65
<211> LENGTH: 29
<212> TYPE: PRT
<213> ORGANISM: Artificial Sequence
<220> FEATURE:
<223> OTHER INFORMATION: tryptic peptide

```
<400> SEQUENCE: 65

Val Thr Ile Ser Cys Ser Gly Ser Ser Tyr Asn Ile Gly Glu Asn Ser
1               5                   10                  15

Val Ser Trp Tyr Gln Gln Leu Pro Gly Thr Ala Pro Lys
            20                  25

<210> SEQ ID NO 66
<211> LENGTH: 30
<212> TYPE: PRT
<213> ORGANISM: Artificial Sequence
<220> FEATURE:
<223> OTHER INFORMATION: tryptic peptide

<400> SEQUENCE: 66

Ser Gly Thr Ser Ala Thr Leu Gly Ile Thr Gly Leu Gln Thr Gly Asp
1               5                   10                  15

Glu Ala Asp Tyr Tyr Cys Gly Thr Trp Asp Ser Asn Leu Arg
            20                  25                  30

<210> SEQ ID NO 67
<211> LENGTH: 6
<212> TYPE: PRT
<213> ORGANISM: Artificial Sequence
<220> FEATURE:
<223> OTHER INFORMATION: tryptic peptide

<400> SEQUENCE: 67

Ala Thr Leu Ser Cys Arg
1               5

<210> SEQ ID NO 68
<211> LENGTH: 9
<212> TYPE: PRT
<213> ORGANISM: Artificial Sequence
<220> FEATURE:
<223> OTHER INFORMATION: tryptic peptide

<400> SEQUENCE: 68

Leu Leu Cys Tyr Gly Ala Ser Thr Arg
1               5

<210> SEQ ID NO 69
<211> LENGTH: 35
<212> TYPE: PRT
<213> ORGANISM: Artificial Sequence
<220> FEATURE:
<223> OTHER INFORMATION: tryptic peptide

<400> SEQUENCE: 69

Phe Ser Cys Ser Gly Ser Gly Thr Asp Phe Thr Leu Thr Ile Ser Ser
1               5                   10                  15

Leu Gln Val Glu Asp Val Ala Val Tyr Tyr Cys Gln Gln Tyr Tyr Thr
            20                  25                  30

Thr Pro Lys
        35

<210> SEQ ID NO 70
<211> LENGTH: 124
<212> TYPE: PRT
<213> ORGANISM: Artificial Sequence
<220> FEATURE:
<223> OTHER INFORMATION: Human - HVHP44S

<400> SEQUENCE: 70
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Cys Ala Ile Ser Gly Ser Gly Gly Ser Thr Tyr Tyr Ala Asp Ser Val
    50                  55                  60

Lys Gly Arg Phe Thr Cys Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Pro Arg Ser Val Ser Gly Leu Arg Gly Val Val Asp
            100                 105                 110

Ser Trp Gly Arg Gly Thr Leu Val Thr Val Ser Ser
            115                 120

<210> SEQ ID NO 71
<211> LENGTH: 113
<212> TYPE: PRT
<213> ORGANISM: Artificial Sequence
<220> FEATURE:
<223> OTHER INFORMATION: Human - HVHB82S

<400> SEQUENCE: 71

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Cys Ala Ile Ser Gly Ser Gly Gly Ser Thr Tyr Tyr Ala Asp Ser Val
    50                  55                  60

Lys Gly Arg Phe Thr Cys Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Thr Asp Met Glu Val Trp Gly Lys Gly Thr Thr Val Thr Val Ser
            100                 105                 110

Ser

<210> SEQ ID NO 72
<211> LENGTH: 123
<212> TYPE: PRT
<213> ORGANISM: Artificial Sequence
<220> FEATURE:
<223> OTHER INFORMATION: Human - HVHP421S

<400> SEQUENCE: 72

Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Cys Ala Ile Ser Gly Ser Gly Gly Ser Thr Tyr Tyr Ala Asp Ser Val
    50                  55                  60

-continued

```
Lys Gly Arg Phe Thr Cys Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Lys Gly Gly Ser Ser Gly Tyr Asp His Pro Asp Tyr
            100                 105                 110

Trp Gly Gln Gly Thr Leu Val Thr Val Ser Ser
            115                 120
```

<210> SEQ ID NO 73
<211> LENGTH: 122
<212> TYPE: PRT
<213> ORGANISM: Artificial Sequence
<220> FEATURE:
<223> OTHER INFORMATION: Human - HVHP419S

<400> SEQUENCE: 73

```
Gln Leu Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Cys Ala Ile Ser Gly Ser Gly Gly Ser Thr Tyr Tyr Ala Asp Ser Val
         50                  55                  60

Lys Gly Arg Phe Thr Cys Ser Arg Asp Asn Ser Lys Asn Ser Leu Tyr
 65                  70                  75                  80

Leu Gln Met Asn Ser Leu Gly Ala Glu Asp Thr Ala Val Tyr Tyr Cys
                 85                  90                  95

Ala Arg Ser Trp Ser Gly Ser Ser Tyr Gly Gly Asp Leu Asp Ser Trp
            100                 105                 110

Gly Gln Gly Thr Leu Val Thr Val Ser Ser
            115                 120
```

<210> SEQ ID NO 74
<211> LENGTH: 125
<212> TYPE: PRT
<213> ORGANISM: Artificial Sequence
<220> FEATURE:
<223> OTHER INFORMATION: Human - HVHP430S

<400> SEQUENCE: 74

```
Gln Val Gln Leu Val Glu Ser Gly Gly Gly Leu Ile Lys Pro Gly Gly
  1               5                  10                  15

Ser Leu Arg Leu Ser Cys Ala Ala Ser Gly Phe Thr Phe Ser Asn Tyr
                 20                  25                  30

Ala Met Ser Trp Val Arg Gln Ala Pro Gly Lys Gly Leu Glu Trp Val
             35                  40                  45

Cys Ala Ile Ser Ser Ser Gly Gly Ser Thr Tyr Tyr Ala Asp Ser Val
         50                  55                  60

Lys Gly Arg Phe Thr Cys Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Val Arg Glu Glu Tyr Arg Cys Ser Gly Thr Ser Cys Pro Gly Ala Phe
            100                 105                 110

Asp Ile Trp Gly Gln Gly Thr Met Val Thr Val Ser Ser
            115                 120                 125
```

<210> SEQ ID NO 75
<211> LENGTH: 119
<212> TYPE: PRT
<213> ORGANISM: Artificial Sequence
<220> FEATURE:
<223> OTHER INFORMATION: Human - HVHP429S

<400> SEQUENCE: 75

```
Glu Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Ile Asn Tyr
            20                  25                  30

Ala Met Ser Trp Val Arg Gln Ala Pro Asp Lys Gly Leu Asp Trp Val
        35                  40                  45

Cys Thr Ile Ser Asn Asn Gly Gly Ala Thr Tyr Tyr Ala Asp Ser Val
    50                  55                  60

Lys Gly Arg Phe Thr Cys Ser Arg Asp Asn Ser Asn Asn Thr Leu Tyr
65                  70                  75                  80

Leu Gln Met Asn Ser Leu Arg Pro Asp Asp Thr Ala Val Tyr Tyr Cys
                85                  90                  95

Ala Lys Gly Pro Ile Asn Thr Gly Arg Tyr Gly Asp Trp Gly Gln Gly
            100                 105                 110

Thr Leu Val Thr Val Ser Ser
        115
```

<210> SEQ ID NO 76
<211> LENGTH: 123
<212> TYPE: PRT
<213> ORGANISM: Artificial Sequence
<220> FEATURE:
<223> OTHER INFORMATION: Human - HVHM41S

<400> SEQUENCE: 76

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Ala Phe Ser Ser Tyr
            20                  25                  30

Ala Met Ser Trp Val Arg Gln Ala Pro Gly Lys Gly Leu Glu Trp Val
        35                  40                  45

Cys Ala Ile Ser Gly Gly Gly Asp His Thr Tyr Tyr Ala Asp Ser Val
    50                  55                  60

Lys Gly Arg Phe Thr Cys Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Met Val Arg Gly Val Ser Ser Ala Pro Phe Asp Tyr
            100                 105                 110

Trp Gly Gln Gly Thr Leu Val Thr Val Ser Ser
        115                 120
```

<210> SEQ ID NO 77
<211> LENGTH: 121
<212> TYPE: PRT
<213> ORGANISM: Artificial Sequence
<220> FEATURE:
<223> OTHER INFORMATION: Human - HVHM81S

<400> SEQUENCE: 77

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Cys Gly Ile Ser Gly Ser Gly Ala Ser Thr Tyr Tyr Ala Asp Ser Val
    50                  55                  60

Lys Gly Arg Phe Thr Cys Ser Arg Asp Asn Ser Lys Asn Thr Leu Tyr
65                  70                  75                  80

Leu Gln Met Asn Ser Leu Arg Ala Gly Asp Thr Ala Leu Tyr Tyr Cys
                85                  90                  95

Ala Arg Gln Ser Ile Thr Gly Pro Thr Gly Ala Phe Asp Val Trp Gly
            100                 105                 110

Gln Gly Thr Met Val Thr Val Ser Ser
            115                 120

<210> SEQ ID NO 78
<211> LENGTH: 123
<212> TYPE: PRT
<213> ORGANISM: Artificial Sequence
<220> FEATURE:
<223> OTHER INFORMATION: Human - HVHP428S

<400> SEQUENCE: 78

Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Phe Arg Gln Ala Pro Gly Lys Gly Leu Glu Trp Val
        35                  40                  45

Cys Phe Ile Arg Ser Lys Ala Tyr Gly Gly Thr Thr Glu Tyr Ala Ala
    50                  55                  60

Ser Val Lys Gly Arg Phe Thr Cys Ser Arg Asp Asp Ser Lys Ser Ile
65                  70                  75                  80

Ala Tyr Leu Gln Met Asn Ser Leu Arg Ala Glu Asp Thr Ala Met Tyr
                85                  90                  95

Tyr Cys Ala Arg Arg Ala Lys Asp Gly Tyr Asn Ser Pro Glu Asp Tyr
            100                 105                 110

Trp Gly Gln Gly Thr Leu Val Thr Val Ser Ser
            115                 120

<210> SEQ ID NO 79
<211> LENGTH: 119
<212> TYPE: PRT
<213> ORGANISM: Artificial Sequence
<220> FEATURE:
<223> OTHER INFORMATION: Human - HVHP420S

<400> SEQUENCE: 79

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Thr Trp Val Arg Gln Ala Pro Gly Lys Gly Leu Glu Trp Val
        35                  40                  45

Cys Arg Ile Lys Thr Lys Thr Asp Gly Gly Thr Thr Asp Tyr Ala Ala
    50                  55                  60

```
Pro Val Lys Gly Arg Phe Thr Cys Ser Arg Asp Asp Ser Lys Asn Thr
 65                  70                  75                  80

Leu Tyr Leu Gln Met Asn Ser Leu Lys Thr Glu Asp Thr Ala Val Tyr
             85                  90                  95

Tyr Cys Thr Thr Asp Arg Asp His Ser Ser Gly Ser Trp Gly Gln Gly
             100                 105                 110

Thr Leu Val Thr Val Ser Ser
        115

<210> SEQ ID NO 80
<211> LENGTH: 119
<212> TYPE: PRT
<213> ORGANISM: Artificial Sequence
<220> FEATURE:
<223> OTHER INFORMATION: Human - HVHP414S

<400> SEQUENCE: 80

Asp Val Gln Leu Val Gln Ser Gly Gly Gly Leu Val Lys Pro Gly Gly
1               5                   10                  15

Ser Leu Arg Leu Ser Cys Thr Ala Ser Gly Phe Pro Phe Ser Asn Ala
            20                  25                  30

Trp Met Ser Trp Val Arg Gln Ala Pro Gly Lys Gly Leu Glu Trp Val
        35                  40                  45

Cys Arg Ile Thr Ser Lys Thr Asp Gly Thr Thr Asp Tyr Val Ala
    50                  55                  60

Pro Val Lys Gly Arg Phe Thr Cys Ser Arg Asp Asp Ser Lys Asn Thr
 65                  70                  75                  80

Leu Tyr Leu Gln Met Asn Ser Leu Lys Thr Glu Asp Thr Ala Val Tyr
             85                  90                  95

Tyr Cys Thr Thr Asp Gln Ala Asn Ala Phe Asp Ile Trp Gly Gln Gly
             100                 105                 110

Thr Met Val Thr Val Ser Ser
        115

<210> SEQ ID NO 81
<211> LENGTH: 118
<212> TYPE: PRT
<213> ORGANISM: Artificial Sequence
<220> FEATURE:
<223> OTHER INFORMATION: Human - HVHP423S

<400> SEQUENCE: 81

Gln Met Gln Leu Val Gln Ser Gly Gly Gly Val Val Gln Pro Gly Gly
1               5                   10                  15

Ser Leu Arg Leu Ser Cys Ala Ala Ser Gly Phe Thr Val Ser Ser Ser
            20                  25                  30

Arg Met Ser Trp Phe Arg Gln Ala Pro Gly Met Gly Leu Glu Trp Val
        35                  40                  45

Cys Val Ile Tyr Ser Gly Gly Ser Thr Tyr Tyr Ala Asp Ser Val Arg
    50                  55                  60

Gly Arg Phe Ser Cys Ser Arg Asp Asn Ser Lys Asn Thr Leu Tyr Leu
 65                  70                  75                  80

Gln Met Asn Ser Leu Arg Ala Glu Asp Thr Ala Leu Tyr Tyr Cys Ala
             85                  90                  95

Arg Glu Arg Glu Gly Ala Val Thr Arg Glu Asp Trp Gly Gln Gly Thr
             100                 105                 110
```

Leu Val Thr Val Ser Ser
        115

<210> SEQ ID NO 82
<211> LENGTH: 119
<212> TYPE: PRT
<213> ORGANISM: Artificial Sequence
<220> FEATURE:
<223> OTHER INFORMATION: Human - HVHP413S

<400> SEQUENCE: 82

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Cys Phe Ile Tyr Ser Gly Gly Ser Thr Tyr Tyr Ala Asp Ser Val Lys
    50                  55                  60

Gly Arg Phe Thr Cys Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ser Arg Val Gly Gly Gly Ala Phe Asp Ile Trp Gly Gln Gly
            100                 105                 110

Thr Met Val Thr Val Ser Ser
        115

<210> SEQ ID NO 83
<211> LENGTH: 120
<212> TYPE: PRT
<213> ORGANISM: Artificial Sequence
<220> FEATURE:
<223> OTHER INFORMATION: Human - HVHP426S

<400> SEQUENCE: 83

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ile Val Asp Gly Tyr
            20                  25                  30

Ala Met His Trp Val Arg Gln Ala Pro Gly Gln Gly Leu Glu Trp Val
        35                  40                  45

Cys Val Thr Asn Asn Gly Gly Ser Thr Ser Tyr Ala Asp Ser Val Lys
    50                  55                  60

Gly Arg Phe Thr Cys Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Ser Ile Thr Gly Pro Thr Gly Ala Phe Asp Ile Trp Gly Gln
            100                 105                 110

Gly Thr Met Val Thr Val Ser Ser
        115                 120

<210> SEQ ID NO 84
<211> LENGTH: 25
<212> TYPE: PRT
<213> ORGANISM: Artificial Sequence
<220> FEATURE:
<223> OTHER INFORMATION: tryptic peptide -continued

```
<400> SEQUENCE: 84

Gln Ala Pro Gly Gln Gly Val Glu Trp Val Cys Val Thr Asn Asn Gly
1               5                   10                  15

Gly Ser Thr Ser Ala Asp Ser Val Lys
            20                  25

<210> SEQ ID NO 85
<211> LENGTH: 5
<212> TYPE: PRT
<213> ORGANISM: Artificial Sequence
<220> FEATURE:
<223> OTHER INFORMATION: tryptic peptide

<400> SEQUENCE: 85

Phe Thr Cys Ser Arg
1               5

<210> SEQ ID NO 86
<211> LENGTH: 8
<212> TYPE: PRT
<213> ORGANISM: Artificial Sequence
<220> FEATURE:
<223> OTHER INFORMATION: linker

<400> SEQUENCE: 86

Gly Ser Gly Ser Lys Ala Ala Ala
1               5

<210> SEQ ID NO 87
<211> LENGTH: 69
<212> TYPE: DNA
<213> ORGANISM: Artificial Sequence
<220> FEATURE:
<223> OTHER INFORMATION: Human - VL24-CDR1
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: k
<222> LOCATION: (21)..(21)
<223> OTHER INFORMATION: k is t or g
<220> FEATURE:
<221> NAME/KEY: r
<222> LOCATION: (31)..(31)
<223> OTHER INFORMATION: r is a or g
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: k
<222> LOCATION: (39)..(39)
<223> OTHER INFORMATION: k is t or g
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: k
<222> LOCATION: (42)..(42)
<223> OTHER INFORMATION: k is t or g
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: k
<222> LOCATION: (45)..(45)
<223> OTHER INFORMATION: k is t or g
<220> FEATURE:
<221> NAME/KEY: misc_feature
```

<222> LOCATION: (49)..(50)
<223> OTHER INFORMATION: n is a, c, g, or t
<220> FEATURE:
<221> NAME/KEY: k
<222> LOCATION: (51)..(51)
<223> OTHER INFORMATION: k is t or g

<400> SEQUENCE: 87
agagtcacca tcacttgcnn kgcaagtcag rgcattnnkn nknnkttann ktggtatcag    60
cagaaacca                                                           69

<210> SEQ ID NO 88
<211> LENGTH: 54
<212> TYPE: DNA
<213> ORGANISM: Artificial Sequence
<220> FEATURE:
<223> OTHER INFORMATION: Human - VL24S-CDR2
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: k
<222> LOCATION: (21)..(21)
<223> OTHER INFORMATION: k is t or g
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: k
<222> LOCATION: (30)..(30)
<223> OTHER INFORMATION: k is t or g
<220> FEATURE:
<221> NAME/KEY: k
<222> LOCATION: (32)..(32)
<223> OTHER INFORMATION: k is t or g
<220> FEATURE:
<221> NAME/KEY: misc_feature
<222> LOCATION: (33)..(35)
<223> OTHER INFORMATION: n is a, c, g, or t
<220> FEATURE:
<221> NAME/KEY: k
<222> LOCATION: (36)..(36)
<223> OTHER INFORMATION: k is t or g

<400> SEQUENCE: 88
cctaaactcc tgtgctttnn kgcatccnnk cknnnkagtg gggtcccatc aagg          54

<210> SEQ ID NO 89
<211> LENGTH: 60
<212> TYPE: DNA
<213> ORGANISM: Artificial Sequence
<220> FEATURE:
<223> OTHER INFORMATION: Human - VL24-CDR3
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: k
<222> LOCATION: (21)..(21)
<223> OTHER INFORMATION: k is t or g
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: k
<222> LOCATION: (27)..(27)
<223> OTHER INFORMATION: k is t or g
<220> FEATURE:
<221> NAME/KEY: misc_feature
<222> LOCATION: (28)..(29)

```
<223> OTHER INFORMATION: n is a, c, g, or t
<220> FEATURE:
<221> NAME/KEY: k
<222> LOCATION: (30)..(30)
<223> OTHER INFORMATION: k is t or g
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: k
<222> LOCATION: (33)..(33)
<223> OTHER INFORMATION: k is t or g
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: k
<222> LOCATION: (36)..(36)
<223> OTHER INFORMATION: k is t or g
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: k
<222> LOCATION: (42)..(42)
<223> OTHER INFORMATION: k is t or g

<400> SEQUENCE: 89
tttgcaactt actactgtnn kcagnnknnk nnknnkcctn nkacgttcgg ccacgggacc    60

<210> SEQ ID NO 90
<211> LENGTH: 63
<212> TYPE: DNA
<213> ORGANISM: Artificial Sequence
<220> FEATURE:
<223> OTHER INFORMATION: Human - VL24-CDR3a
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: k
<222> LOCATION: (30)..(30)
<223> OTHER INFORMATION: k is t or g
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: k
<222> LOCATION: (36)..(36)
<223> OTHER INFORMATION: k is t or g
<220> FEATURE:
<221> NAME/KEY: k
<222> LOCATION: (39)..(39)
<223> OTHER INFORMATION: k is t or g
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: k
```

```
<222> LOCATION: (42)..(42)
<223> OTHER INFORMATION: k is t or g
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: k
<222> LOCATION: (44)..(44)
<223> OTHER INFORMATION: k is t or g
<220> FEATURE:
<221> NAME/KEY: k
<222> LOCATION: (51)..(51)
<223> OTHER INFORMATION: k is t or g
<220> FEATURE:
<221> NAME/KEY: k
<222> LOCATION: (54)..(54)
<223> OTHER INFORMATION: k is t or g

<400> SEQUENCE: 90
tttgcaactt actactgtnn kcagnnknnk nnknnkcctn nknnkacgtt cggccacggg      60
acc                                                                    63

<210> SEQ ID NO 91
<211> LENGTH: 66
<212> TYPE: DNA
<213> ORGANISM: Artificial Sequence
<220> FEATURE:
<223> OTHER INFORMATION: Human - VL24-CDR3b
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: k
<222> LOCATION: (30)..(30)
<223> OTHER INFORMATION: k is t or g
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: k
<222> LOCATION: (36)..(36)
<223> OTHER INFORMATION: k is t or g
<220> FEATURE:
<221> NAME/KEY: k
<222> LOCATION: (39)..(39)
<223> OTHER INFORMATION: k is t or g
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: k
<222> LOCATION: (42)..(42)
<223> OTHER INFORMATION: k is t or g
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: k
<222> LOCATION: (45)..(45)
```

```
<223> OTHER INFORMATION: k is t or g
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: k
<222> LOCATION: (51)..(51)
<223> OTHER INFORMATION: k is t or g
<220> FEATURE:
<221> NAME/KEY: k
<222> LOCATION: (54)..(54)
<223> OTHER INFORMATION: k is t or g
<220> FEATURE:
<221> NAME/KEY: k
<222> LOCATION: (57)..(57)
<223> OTHER INFORMATION: k is t or g

<400> SEQUENCE: 91
tttgcaactt actactgtnn kcagnnknnk nnknnkcctn nknnknnkac gttcggccac     60
gggacc                                                               66

<210> SEQ ID NO 92
<211> LENGTH: 24
<212> TYPE: DNA
<213> ORGANISM: Artificial Sequence
<220> FEATURE:
<223> OTHER INFORMATION: Human - -96GIII

<400> SEQUENCE: 92
ccctcatagt tagcgtaacg atct                                           24

<210> SEQ ID NO 93
<211> LENGTH: 27
<212> TYPE: DNA
<213> ORGANISM: Artificial Sequence
<220> FEATURE:
<223> OTHER INFORMATION: Human - fdTGIII

<400> SEQUENCE: 93
gtgaaaaaat tattattcgc aattcct                                        27

<210> SEQ ID NO 94
<211> LENGTH: 26
<212> TYPE: DNA
<213> ORGANISM: Artificial Sequence
<220> FEATURE:
<223> OTHER INFORMATION: Human - HVL24-BamHI

<400> SEQUENCE: 94
ttgttcggat cctaggacgg tcacct                                         26

<210> SEQ ID NO 95
<211> LENGTH: 26
<212> TYPE: DNA
<213> ORGANISM: Artificial Sequence
<220> FEATURE:
<223> OTHER INFORMATION: Human - HVL24-BbsI

<400> SEQUENCE: 95
tatgaagaca ccaggccgac atccag                                         26

<210> SEQ ID NO 96
<211> LENGTH: 54
<212> TYPE: DNA
<213> ORGANISM: Artificial Sequence
<220> FEATURE:
<223> OTHER INFORMATION: Human - KT124
```

-continued

<400> SEQUENCE: 96
tgtgctacca ccactactac taatagcgca gacccactcc agccccttcc ctgg    54

<210> SEQ ID NO 97
<211> LENGTH: 54
<212> TYPE: DNA
<213> ORGANISM: Artificial Sequence
<220> FEATURE:
<223> OTHER INFORMATION: Human - KT125

<400> SEQUENCE: 97
cacggtgttc ttggaattgt ctctggagca ggtgaatcgg cccttcacgg agtc    54

<210> SEQ ID NO 98
<211> LENGTH: 17
<212> TYPE: DNA
<213> ORGANISM: Artificial Sequence
<220> FEATURE:
<223> OTHER INFORMATION: Human - M13RPb

<400> SEQUENCE: 98
caggaaacag ctatgac    17

<210> SEQ ID NO 99
<211> LENGTH: 107
<212> TYPE: PRT
<213> ORGANISM: Artificial Sequence
<220> FEATURE:
<223> OTHER INFORMATION: Human - HVLHLNN

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Ser Ile Asn Asn Arg
            20                  25                  30

Leu Tyr Trp Tyr Gln Gln Lys Pro Gly Lys Ala Pro Lys Leu Leu Cys
        35                  40                  45

Phe Pro Ala Ser Phe Leu Phe Ser Gly Val Pro Ser Arg Phe Ser Cys
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly His Gly Thr Lys Val Thr Val Leu
            100                 105

<210> SEQ ID NO 100
<211> LENGTH: 107
<212> TYPE: PRT
<213> ORGANISM: Artificial Sequence
<220> FEATURE:
<223> OTHER INFORMATION: Human - HVLHLDS

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Thr Val Ser Gln Gly Ile Asp Ser Arg
            20                  25                  30

Leu Tyr Trp Tyr Gln Gln Lys Pro Gly Lys Ala Pro Lys Leu Leu Cys
        35                  40                  45

```
Phe Pro Ala Ser Leu Leu Glu Ser Gly Val Pro Ser Arg Phe Ser Cys
        50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Gln Gln Ser Tyr Ser Thr Pro Arg
                 85                  90                  95

Thr Phe Gly His Gly Thr Lys Val Thr Val Leu
                100                 105

<210> SEQ ID NO 101
<211> LENGTH: 109
<212> TYPE: PRT
<213> ORGANISM: Artificial Sequence
<220> FEATURE:
<223> OTHER INFORMATION: Human - HVLHLRN

<400> SEQUENCE: 101

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Gly Ile Arg Asn Arg
                 20                  25                  30

Leu Tyr Trp Tyr Gln Gln Lys Pro Gly Lys Ala Pro Lys Leu Leu Cys
             35                  40                  45

Phe Pro Ala Ser Ile Leu Asp Ser Gly Val Pro Ser Arg Phe Ser Cys
        50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Ala Gln Gln Pro Gly Leu Pro Asn
                 85                  90                  95

Ser Arg Thr Phe Gly His Gly Thr Lys Val Thr Val Leu
                100                 105

<210> SEQ ID NO 102
<211> LENGTH: 107
<212> TYPE: PRT
<213> ORGANISM: Artificial Sequence
<220> FEATURE:
<223> OTHER INFORMATION: Human - HVLHLNE

<400> SEQUENCE: 102

Asp Ile Gln Met Thr Gln Ser Pro Ser Ser Leu Ser Ala Ser Val Gly
  1               5                  10                  15

Asp Arg Val Thr Ile Thr Cys Asp Ala Ser Gln Ser Ile Asn Glu Arg
                 20                  25                  30

Leu Tyr Trp Tyr Gln Gln Lys Pro Gly Lys Ala Pro Lys Leu Leu Cys
             35                  40                  45

Phe Pro Ala Ser Ile Leu Thr Ser Gly Val Pro Ser Arg Phe Ser Cys
        50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Arg Gln Pro Arg Ser Gly Pro Ser
                 85                  90                  95

Thr Phe Gly His Gly Thr Lys Val Thr Val Leu
                100                 105

<210> SEQ ID NO 103
<211> LENGTH: 108
<212> TYPE: PRT
<213> ORGANISM: Artificial Sequence
```

```
<220> FEATURE:
<223> OTHER INFORMATION: Human - HVLHLAQ

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Ser Ile Ala Gln Arg
            20                  25                  30

Leu Tyr Trp Tyr Gln Gln Lys Pro Gly Lys Ala Pro Lys Leu Leu Cys
        35                  40                  45

Phe Pro Ala Ser Leu Leu His Ser Gly Val Pro Ser Arg Phe Ser Cys
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Ala Gln Arg Ala Ser Pro Pro Arg
                85                  90                  95

Pro Thr Phe Gly His Gly Thr Lys Val Thr Val Leu
            100                 105

<210> SEQ ID NO 104
<211> LENGTH: 109
<212> TYPE: PRT
<213> ORGANISM: Artificial Sequence
<220> FEATURE:
<223> OTHER INFORMATION: Human - HVLHLEM

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Glu Met Phe
            20                  25                  30

Leu Gln Trp Tyr Gln Gln Lys Pro Gly Lys Ala Pro Lys Leu Leu Cys
        35                  40                  45

Phe Ala Ala Ser Thr Leu Gln Ser Gly Val Pro Ser Arg Phe Ser Cys
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Val Gln Pro Gly Val Ala Pro Pro
                85                  90                  95

Pro Gly Thr Phe Gly His Gly Thr Lys Val Thr Val Leu
            100                 105

<210> SEQ ID NO 105
<211> LENGTH: 108
<212> TYPE: PRT
<213> ORGANISM: Artificial Sequence
<220> FEATURE:
<223> OTHER INFORMATION: Human - HVLHLQI

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gln Ile Met
            20                  25                  30

Leu Asp Trp Tyr Gln Gln Lys Pro Gly Lys Ala Pro Lys Leu Leu Cys
        35                  40                  45

Phe Gly Ala Ser Phe Leu Ile Ser Gly Val Pro Ser Arg Phe Ser Cys
    50                  55                  60
```

```
Ser Gly Ser Gly Thr Asp Phe Thr Leu Thr Ile Ser Asn Leu Gln Pro
 65                  70                  75                  80

Glu Asp Phe Ala Thr Tyr Tyr Cys Arg Gln Thr Trp Thr Pro Pro Ala
                 85                  90                  95

Pro Thr Phe Gly His Gly Thr Lys Val Thr Val Leu
            100                 105

<210> SEQ ID NO 106
<211> LENGTH: 107
<212> TYPE: PRT
<213> ORGANISM: Artificial Sequence
<220> FEATURE:
<223> OTHER INFORMATION: Human - HVLHLYS

<400> SEQUENCE: 106

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Tyr Ser Lys
                20                  25                  30

Leu Tyr Trp Tyr Gln Gln Lys Pro Gly Lys Ala Pro Lys Leu Leu Cys
             35                  40                  45

Phe Pro Ala Ser Leu Leu Trp Ser Gly Val Pro Ser Arg Phe Ser Cys
 50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Leu Gln Asn Ala Ala Asp Pro His
                 85                  90                  95

Arg Thr Phe Gly His Gly Thr Lys Val Arg Leu
            100                 105

<210> SEQ ID NO 107
<211> LENGTH: 109
<212> TYPE: PRT
<213> ORGANISM: Artificial Sequence
<220> FEATURE:
<223> OTHER INFORMATION: Human - HVLHSA1

<400> SEQUENCE: 107

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Tyr
                20                  25                  30

Leu Asn Trp Tyr Gln Gln Lys Pro Gly Lys Ala Pro Lys Leu Leu Cys
             35                  40                  45

Phe Gly Ala Ser Arg Leu Asn Ser Gly Val Pro Ser Arg Phe Ser Cys
 50                  55                  60

Ser Gly Ser Gly Thr Asp Phe Thr Leu Thr Ile Ser Asn Leu Gln Pro
 65                  70                  75                  80

Glu Asp Phe Ala Thr Tyr Tyr Cys Arg Gln Leu Phe Pro Leu Pro Asp
                 85                  90                  95

Arg Arg Thr Phe Gly His Gly Thr Lys Val Thr Val Leu
            100                 105

<210> SEQ ID NO 108
<211> LENGTH: 107
<212> TYPE: PRT
<213> ORGANISM: Artificial Sequence
<220> FEATURE:
<223> OTHER INFORMATION: Human - HVLHLFL
```

```
<400> SEQUENCE: 108

Asp Ile Gln Met Thr Gln Ser Pro Ser Ser Leu Ser Ala Ser Val Gly
1               5                  10                  15

Asp Arg Val Thr Ile Thr Cys Leu Ala Ser Gln Ser Ile Phe Leu Tyr
            20                  25                  30

Leu Asp Trp Tyr Gln Gln Lys Pro Gly Lys Ala Pro Lys Leu Leu Cys
            35                  40                  45

Phe Phe Ala Ser Thr Leu Glu Ser Gly Val Pro Ser Arg Phe Ser Cys
        50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly His Gly Thr Lys Val Thr Val Leu
                100                 105
```

ENGINEERING OF IMMUNOGLOBULIN DOMAINS

RELATED APPLICATIONS

This application is a continuation of U.S. application Ser. No. 13/981,967, filed on Jul. 26, 2013, which is a national stage filing under 35 U.S.C. § 371 of international application PCT/CA2012/000126, filed Jan. 27, 2012, and claims the benefit under 35 U.S.C. § 119(e) of U.S. Provisional Application Ser. No. 61/437,174, filed on Jan. 28, 2011, the disclosure of each of which is incorporated by reference herein in its entirety.

FIELD OF THE INVENTION

The present invention relates to engineering of immunoglobulin domains. More specifically, the present invention is directed to engineering of immunoglobulin domains to improve biophysical properties of the immunoglobulin.

BACKGROUND OF THE INVENTION

Protein stability plays an important role in protein therapeutics, since unstable proteins lead to variable therapeutic availability and unpredictable physiological effects in vivo (Horwich, 2002; Wetzel, 1988; Mitraki and King, 1992; Worn and Pluckthun, 2001; Hurle et al., 1994). In the field of antibody therapeutics, human conventional antibodies and antibody fragments are either too large and/or have poor biophysical properties such as low stability, irreversible unfolding and low expression; therefore, they have limited clinical applications. "Naturally-occurring" single-domain antibodies (sdAbs), e.g., camelid $V_H$Hs, shark $V_{NAR}$s, do not have the aforementioned problems, though they are immunogenic due to their non-human nature.

Fully human sdAbs, e.g., $V_H$ or $V_L$, would be ideal molecules for human therapy because of their expected lower (or lack of) immunogenicity; however, they are prone to aggregation due to their low stability and solubility (Ward et al., 1989; Davies and Reichmann, 1994; Davies and Riechmann, 1995; Tanha et al., 2001; Kazlauskas and Bornscheuer, 2009; Holliger and Hudson, 2005; Hoogenboom, 2005). This limits their applications in human therapy. Given the significance of stable antibodies as therapeutic molecules, it is not surprising that efforts have been made to select more stable/soluble single domain antibodies (Davies and Riechmann, 1996a; Jespers et al., 2004; To et al., 2005; Tanha et al., 2006; Arbabi-Ghahroudi et al., 2009a; Arbabi-Ghahroudi et al., 2009b; Arbabi-Ghahroudi et al., 2010).

One typical method of improving stability of sdAbs is to use one sdAb as a scaffold to generate a display library comprising hundreds of millions of sdAb varieties, each with a unique specificity; binders (sdAbs) are then selected against target antigens by panning techniques. In one approach to this method, the parent scaffold is first engineered to be non-aggregating then the library is constructed based on the non-aggregating scaffold; since it is assumed that the progeny sdAbs in the library by-and-large "inherit" the non-aggregation property of the parent scaffold, a conventional panning based only on the affinity criterion is performed to select for non-aggregating sdAbs. In a second approach, the parent scaffold may or may not be non-aggregating, and libraries thereof are panned based on both affinity and non-aggregation criteria. Regardless of the approach, aggregating and non-aggregating sdAbs are frequently co-selected; in many instances, the aggregating sdAbs dominate the selection process, or the selected binders have low solubility, stability and expression levels. Furthermore, a number of $V_H$ antibodies are lost during affinity selection, where great ranges of amino acid substitutions occur to destabilize the $V_H$s leading to aggregation (Kazlauskas and Bornscheuer, 2009; Bloom et al., 2006). These factors make the selection of non-aggregation sdAbs tedious and labour intensive and, at times, daunting.

Thus, there remains a need in the art for antibodies that are non-aggregating, soluble, and stable.

SUMMARY OF THE INVENTION

The present invention relates to engineering of immunoglobulin domains. More specifically, the present invention is directed to engineering of immunoglobulin domains to improve biophysical properties of the immunoglobulin.

The present invention provides a composition comprising an immunoglobulin scaffold, said immunoglobulin scaffold comprising one or more than one non-canonical disulfide bond in the framework region (FR), as well as methods for making and using the compositions. In one embodiment, the immunoglobulin scaffold is a single domain antibody (sdAb). The immunoglobulin scaffold may be $V_H$; the $V_H$ may be of the $V_H$3 family. Alternatively, the immunoglobulin scaffold may be a $V_L$; the $V_L$ may be of the kappa or lambda family. In one embodiment the immunoglobulin scaffold is human. In one embodiment the immunoglobulin scaffold is humaneered. In one embodiment the immunoglobulin scaffold is camelid. In one embodiment, the camelid species is selected from the group consisting of llama, alpaca and camel.

In the immunoglobulin scaffold as described above, the one or more than one non-canonical disulfide bond may be formed between cysteines introduced by mutations in FR2 and FR3. In the case where the immunoglobulin scaffold is a $V_H$, the invention provides a method of making the scaffold wherein the Cys may be introduced at any one of positions 47-49 and any one of positions 67-71, based on Kabat numbering. In one embodiment, the Cys may be introduced at positions 49 and 69, based on Kabat numbering. In the case where the immunoglobulin scaffold is a $V_L$, the invention provides a method of making the scaffold wherein the Cys residues may be introduced at any one of positions 46-49 and any one of positions 62-66, based on Kabat numbering. In one embodiment, the Cys residues may be introduced at positions 48 and 64, based on Kabat numbering.

The immunoglobulin scaffold described herein may comprise a polypeptide sequence comprising at least two non-canonical Cys residues introduced into the framework regions FR2 and FR3 of an antibody variable region. In one embodiment, the polypeptide comprises a Cys residue at a position selected from residues 47 to 49 of a $V_H$ FR2 regions and a Cys residue at a position selected from residues 69 to 71 of a $V_H$ FR3 regions of a $V_H$ sdAb domain. In one embodiment, the polypeptide comprises a Cys residue at a position selected from residues 46 to 49 of a $V_L$ FR2 regions and a Cys residue at a position selected from residues 62 to 66 of a $V_L$ FR3 regions of a $V_L$ sdAb domain.

In one embodiment, the polypeptide comprises at least a Cys residue at position 49 and at least a Cys residue at position 69 of a $V_H$ domain. In one embodiment, the inventive $V_H$ domain comprises a sdAb fragment. In one embodiment, the invention provides an expression library comprising the inventive $V_H$ sdAb fragment, wherein the inventive sdAb fragments comprise a multiplicity of CDR sequences. In one embodiment, the position of the CDR regions of an inventive V_H sdAb fragment selected from the group of SEQ ID NOS: 2, 4, 6 and 8 are at the positions provided in FIG. 1A and those selected from the group of SEQ ID NOS: 70 to 83 are at the position provided for the corresponding wild type sequences in FIG. 2 of the PCT publication WO2006/099747.

In one embodiment, the polypeptide comprises at least a Cys residue at position 48 and at least a Cys residue at position 64 of a V_L domain. In one embodiment, the inventive V_L domain comprises a sdAb fragment. In one embodiment, the invention provides an expression library comprising the inventive V_L sdAb fragment, wherein the inventive sdAb fragments comprise a multiplicity of CDR sequences. In one embodiment, the position of the CDR regions of an inventive V_L sdAb fragment selected from the group of SEQ ID NOS: 10, 12, 14, 16, 18, 20, 22 and 24 are at the positions provided in FIG. 1B.

In one embodiment, the CDR residues of the inventive polypeptides may be any suitable sequence and may have a variable number of residues other than the number provided in FIGS. 1A and 1B.

In one embodiment, the inventive immunoglobulin polypeptide comprises the scaffold region of one or more of the sequences selected from the group consisting of (SEQ ID NO: 2)
QVQLVESGGGLIKPGGSLRLSCAASGDTVSDESMTWVRQAPGKGLEWV

CAISSSGGSTYYADSVKGRFTCSRDNSKNTVYLQMNSLRAEDTAVY

YCVTDNRSCQTSLCTSTTRSWGQGTMVTVSS;

(SEQ ID NO: 4)
QVQLVESGGGLIKPGGSLRLSCAASGVTLSPECMAWVRQAPGKGLEWV

CAISSSGGSTYYADSVKGRFTCSRDNSKNIVYLQMNSLRAEDTAVY

YCVSCEGENAFWGQGTMVIVSS;

(SEQ ID NO: 6)
QVQLVESGGGLIKPGGSLRLSCAASGYTVSSECMGWVRQAPGKGLEWV

CAISSSGGSTYYADSVKGRFTCSRDNSKNTVYLQMNSLRAEDTAVY

YCVRDSKNCHDKDCTRPYCSWGQGTMVTVSS;

(SEQ ID NO: 8)
QVQLVESGGGLIKPGGSLRLSCAASGFSVISESMTWVRQAPGKGLEWV

CAISSSGGSTYYADSVKGRFTCSRDNSKNTVHLQMNSLRAEDTAVY

YCAAKKIDGARYDYWGQGTMVTVSS;

(SEQ ID NO: 10)
DIQMTQSPSSLSASVGDRVTITCRASQSISTYLNWYQQKPGKAPKLL

CFAASTLQSGVPSRFCSGSGTDFTLTISNLQPEDFATYYCQQSYS

TPRTFGHGTKVTVL;

(SEQ ID NO: 12)
EIVLIQSPTTLSLSPGERATLSCRASQSVGRYLAWYQQRPGQAPRLL

CFDTSNRAPGVPARFCRGSGTLFTLTISSLEPEDSAVYFCQQRSS

GLTFGGGTKVTVL;

(SEQ ID NO: 14)
EIVMTQSPATLSLSPGERATLSCRASQSVSSSLAWYQQKPGQAPRL

ICYGTSNRATGIPDRFCSGSGTHFILTINRLEPGDFAVYYCQQYG

SSPRTFGQGTKVEIK;

(SEQ ID NO: 16)
DIQMTQSPSSLSASVGDRVTITCRASQDIRTDLDWFQQRPGRAPHRL

CYGASSLQGGVPSRFCSGSGTEFTLTISGLQPEDFATYYCLQHHT

YPRTFGLGTKVTVL;

(SEQ ID NO: 18)
EIVMTQSPVTLSLSPGERATLSCRASQSVGTSLAWYQQKPGQAPRLL

CYDASNRATGISARFCSGSGTDFTLTISSLEPEDFAVYYCQQRYN

WPRTFGGGTKVTVL;

(SEQ ID NO: 20)
ETTLTQSPATLSVSPGERATFSCRASQSVSNNLAWYQQKPGQAPRLL

CYGASSRTTGIPDRFCSGSGTDFTLTISRLEPEDFAVYYCQQYDT

SPRTFGQGTKVEIK;

(SEQ ID NO: 22)
QSVVTQPPSVSAAPGQRVTISCSGSSYNIGENSVSWYQQLPGTAPKLL

CYGNDKRPSGIPDRFCSKSGTSATLGITGLQTGDEADYYCGTWDS

NLRASVFGGGTKVTVL;

(SEQ ID NO: 24)
ETTLTQSPGTLSLSPGERATLSCRASQSVRNNLAWYQQRPGQAPRLL

CYGASTRATGIPARFCSGSGTDFTLTISSLQVEDVAVYYCQQYYT

TPKTFGQGTKVEIK, (SEQ ID NO: 70)
EVQLVESGGGLVQPGGSLRLSCAASGFTFSSYAMSWVRQAPGKGLEW

VCAISGSGGSTYYADSVKGRFTCSRDNSKNTLYLQMNSLRAEDTAV

YYCAKDEPRSVSGLRGVVDSWGRGTLVTVS

S (SEQ ID NO: 71)
QVQLQESGGGLVQPGGSLRLSCAASGFTFSSYAMSWVRQAPGKGLEW

VCAISGSGGSTYYADSVKGRFTCSRDNSKNTLYLQMNSLRAEDTAV

YYCGTDMEVWGKGTTVTVSS (SEQ ID NO: 72)
QLQLQESGGGVVQPGRSLRLSCAASGFTFSSYAMSWVRQAPGKGLEW

VCAISGSGGSTYYADSVKGRFTCSRDNSKNTLYLQMNSLRAEDTAV

YYCAKDGKGGSSGYDHPDYWGQGTLVTVSS (SEQ ID NO: 73)
QLQLQESGGGLVQPGGSLRLSCAASGFTFSSYAMSWVRQAPGKGLEW

VCAISGSGGSTYYADSVKGRFTCSRDNSKNSLYLQMNSLGAEDTAV

YYCARSWSGSSYGGDLDSWGQGTLVTVSS (SEQ ID NO: 74)
QVQLVESGGGLIKPGGSLRLSCAASGFTFSNYAMSWVRQAPGKGLEW

VCAISSSGGSTYYADSVKGRFTCSRDNSKNTVYLQMNSLRAEDTAV

YYCVREEYRCSGTSCPGAFDIWGQGTMVTVSS

-continued (SEQ ID NO: 75)
EVQLVESGGTLVQPGGSLRLSCAASGFTFINYAMSWVRQAPDKGLDW

VCTISNNGGATYYADSVKGRFTCSRDNSNNTLYLQMNSLRPDDTAV

YYCAKGPINTGRYGDWGQGTLVTVSS (SEQ ID NO: 76)
QVQLVQSGGGLVQPGRSLRLSCAASGFAFSSYAMSWVRQAPGKGLEW

VCAISGGGDHTYYADSVKGRFTCSRDNSKNTLYLQMNSLRAEDTAV

YYCAKEGMVRGVSSAPFDYWGQGTLVTVSS (SEQ ID NO: 77)
EVQLVQSGGGLVQPGRSLRLSCAASGFTFDDYAMHWVRQAPGKGLEW

VCGISGSGASTYYADSVKGRFTCSRDNSKNTLYLQMNSLRAGDTAL

YYCARQSITGPTGAFDVWGQGTMVTVSS (SEQ ID NO: 78)
QLQLQESGGGLVQPGGSLRLSCAASGFTFSSYAMSWFRQAPGKGLEW

VCFIRSKAYGGTTEYAASVKGRFTCSRDDSKSIAYLQMNSLRAEDT

AMYYCARRAKDGYNSPEDYWGQGTLVTVSS (SEQ ID NO: 79)
QVQLVESGGGLVKPGGSLRLSCAASGFTFSNAWMTWVRQAPGKGLEW

VCRIKTKTDGGTTDYAAPVKGRFTCSRDDSKNTLYLQMNSLKTEDT

AVYYCTTDRDHSSGSWGQGTLVTVSS (SEQ ID NO: 80)
DVQLVQSGGGLVKPGGSLRLSCTASGFPFSNAWMSWVRQAPGKGLEW

VCRITSKTDGGITDYVAPVKGRFTCSRDDSKNTLYLQMNSLKTEDT

AVYYCTTDQANAFDIWGQGTMVTVSS (SEQ ID NO: 81)
QMQLVQSGGGVVQPGGSLRLSCAASGFTVSSSRMSWFRQAPGMGLEW

VCVIYSGGSTYYADSVRGRFSCSRDNSKNTLYLQMNSLRAEDTALY

YCAREREGAVTREDWGQGTLVTVSS (SEQ ID NO: 82)
QVQLVQSGGGLVKPGGSLRLSCAASGFTFSDYYMSWVRQAPGKGLEW

VCFIYSGGSTYYADSVKGRFTCSRDNSKNTLYLQMNSLRAEDTAVY

YCARESRVGGGAFDIWGQGTMVTVSS (SEQ ID NO: 83)
QVQLVQSGGGVVQPGRSLRLSCAASGFIVDGYAMHWVRQAPGQGLEW

VCVINNGGSTSYADSVKGRFTCSRDNSKNTVYLQMNSLRAEDTAVY

YCARQSITGPTGAFDIWGQGTMVTVSS or sequences substantially identical thereto, or fragments thereof, with the proviso that the substantially identical sequence, or fragment thereof, retains both the canonical and non-canonical disulfide bonds, and wherein the sequence in the regions of the CDRs may be any suitable sequence and may have a suitable but variable number of residues in each of CDR1, CDR2 and CDR3. In the case of SEQ ID Nos: 2, 4, 6, 8, 10, 12, 14, 16, 18, 20, 22 and 24, the residues that comprise the CDRs are as provided in FIGS. 1A and 1B. In the case of SEQ ID Nos: 70 through 83, the residues that comprise the CDRs are as provided in the corresponding wild type clones as provided in FIG. 2 of PCT publication WO2006/099747.

The present invention also encompasses a recombinant library encoding a diversity of variable domains, the variable domains comprising a multiplicity of CDRs comprising a variety of suitable sequences and lengths interspersed by the framework regions of a scaffold comprising the inventive non-canonical Cys-Cys residues as described herein. In one embodiment, the recombinant library comprises mammalian sequences. In one embodiment, the recombinant library comprises human sequences. In one embodiment, the recombinant library comprises camelid sequences. In one embodiment, the recombinant library comprises a diversity of sequences that, once selected, is optionally matured and/or humaneered.

The present invention also provides a method of improving stability of single domain antibodies, comprising introducing one or more than one non-canonical disulfide bond in the framework regions.

The present invention provides methods for engineering $V_H$ and $V_L$ domains with enhanced stability. The formation of additional disulfide linkage(s) in $V_H$ and $V_L$ domains by introducing Cys pair(s) at specific locations is shown herein to transform $V_H$s and $V_L$s into highly non-aggregating, soluble, stable and expressible domains. Specifically, these advantageous properties are obtained when residues within the FR2 and FR3 regions are replaced such that a Cys pair at amino acid positions 49 and 69 for $V_H$, and 48 and 64 for $V_L$ (Kabat numbering) was introduced. Formation of disulfide linkages in between the introduced non-canonical residues in the Cys mutants was confirmed by mass spectrometry. All Cys mutants modified in this manner, i.e., containing the listed non-canonical disulfide bridge, showed no adverse expression in *E. coli*, no adverse conformational changes as shown by surface plasmon resonance ("SPR") binding measurements and showed either decreased or a lack of aggregation. Additionally, all mutants had drastically higher stability, having melting temperatures at least 11° C. higher than those of their wild-type counterparts. The present data demonstrate that stabilization of $V_H$ and $V_L$ domain frameworks by introduction of such a disulfide linkage into either a $V_H$ or $V_L$ scaffold, or both, can improve their protease resistance. $V_H$ and/or $V_L$ libraries based on the engineered scaffolds of the present invention can be prepared to identify stable and nonaggregating $V_H$s and $V_L$s that bind specific target molecules. Various display libraries known in the art may be used to express the $V_H$ and/or $V_L$ constructs of the invention. In one embodiment, the library is a single domain antibody ("sdAb") library.

The present invention provides a novel approach that may (i) convert aggregating sdAb to non-aggregating sdAb; (ii) increase the efficiency of obtaining non-aggregating sdAb from sdAb libraries; (iii) additionally increase the stability, e.g., melting temperature, refolding efficiency, resistance to proteases, and expression level, of sdAb. The provision of $V_H$ and $V_L$ scaffolds with these characteristics may allow the recovery of broader ranges of antibodies from antibody libraries; the retention of a high degree of non-aggregation and stability may lead to isolating novel antibodies that could otherwise be lost during the antibody selection process. Additionally, the improved biophysical characteristics may allow the $V_H$ and $V_L$ to be broadly applicable in therapeutics and industrial field.

BRIEF DESCRIPTION OF THE DRAWINGS

These and other features of the invention will now be described by way of example, with reference to the appended drawings, wherein:

FIGS. 1A and 1B show the primary structures of $V_H$, $V_L$, and corresponding Cys mutants. FIG. 1A shows the numbering and CDR designation of $V_H$ using Kabat numbering system (Kabat et al., 1991). The residues (Ser 49 and Ile 69) presently replaced by cysteines are marked by grey shading. Sequences from top to bottom: HVHAm302 is SEQ ID NO: 1; HVHAm302S is SEQ ID NO: 2; HVHAm427 is SEQ ID NO: 3; HVHAm427S is SEQ ID NO: 4; HVHAm431 is SEQ ID NO: 5; HVHAm431S is SEQ ID NO: 6; HVHPC235 is SEQ ID NO: 7; and HVHPC235S is SEQ ID NO: 8. FIG. 1B shows the numbering and CDR designation of $V_L$ using Kabat numbering. The residues (Ile/Val 48 and Gly/Ala 64) presently replaced by cysteines are marked by grey shading. Sequences from top to bottom: HVLP324 is SEQ ID NO: 9; HVLP324S is SEQ ID NO: 10; HVLP342 is SEQ ID NO: 15; HVLP342S is SEQ ID NO: 16; HVLP335 is SEQ ID NO: 13; HVLP335S is SEQ ID NO: 14; HVLP364 is SEQ ID NO: 19; HVLP364S is SEQ ID NO: 20; HVLP3103 is SEQ ID NO: 23; HVLP3103S is SEQ ID NO: 24; HVLP325 is SEQ ID NO: 11; HVLP325S is SEQ ID NO: 12; HVLP351 is SEQ ID NO: 17; HVLP351S is SEQ ID NO: 18; HVLP389 is SEQ ID NO: 21; and HVLP389S is SEQ ID NO: 22. "FR" indicates framework regions, CDR, complementarity-determining regions, of $V_H$s and $V_L$s.

In FIG. 6C, the thermal unfolding curves of HVLP389 and HVLP325, which had the lowest and highest $T_m$s, respectively, are compared side by side to their Cys mutant versions, HVLP389S and HVLP325S.

In FIG. 7A, the concentration of each $V_H$ in μM was the following: 0.2, 0.5, 1.0, 1.5, 2.0, 2.5 and 3.35 (HVHAm302); 0.2, 0.2, 0.5, 1.0, 1.5, 2.0, 3.0 and 3.88 (HVHAm427); 0.5, 0.5, 1.0, 1.5, 2.0, 2.5 and 3.81 (HVHAm431); 0.01, 0.01, 0.02, 0.05, 0.25, 0.25, 0.5, 1.0 and 2.5 (HVHAmC235); 0.4, 0.8, 1.6, 3.2, 5.4 and 8.22 (HVHAm302S); 0.2, 0.5, 1.0, 1.5, 2.0, 2.0 and 3.08 (HVHAm427S); 0.5, 1.0, 1.0, 2.0, 4.0, 6.5, 10.0 and 13.3 (HVHAm431S); 0.025, 0.025, 0.05, 0.1, 0.2, 0.4, 0.4, 0.8, 0.8, 0.8, 1.5, 1.5, 3.0, 6.0 and 9.9 (HVHAmC235S). The calculated $K_D$s are recorded in Table 4. RU, Resonance Unit. FIG. 7B is a kinetic rate diagram with isoaffinity diagonals plot for the wild-type and mutant $V_H$s. The kinetic rates ($k_{on}$ and $k_{off}$) determined by SPR analyses are plotted on a two-dimensional plane in logarithmic scale so that $V_H$s located on the same diagonal line have identical $K_D$ values.

In FIG. 8A, the concentration of each $V_L$ was the following: 0.2, 0.5, 0.75, 1, 2, 3, 5 and 10 µM (HVLP389, HVLP351 and HVLP364); 1, 2, 3, 5, 7.5 and 10 nM (HVLP342); 0.2, 0.5, 1, 2, 3, 5 and 10 µM (HVLP335); 0.2, 0.5, 1, 1.5, 2 and 5 µM (HVLP325), 0.2, 0.5, 0.75, 1, 1.5, 2, 3 and 5 µM (HVLP3103) and 1, 2, 4, 6, 8 and 10 nM (HVLP324). The sensorgrams for HVLP324 and HVLP342 bindings to the low affinity site of protein L are not included, though the calculated $K_D$s are recorded in Table 4. In FIG. 8B, the concentration of the Cys mutant $V_L$s was: 0.05, 0.1, 0.2, 0.2, 0.5, 0.75, 1, 1.5, 2, 3, 4, and 7 µM (HVLP389S); 0.1, 0.2, 0.2, 0.4, 0.6, 1, 2, 4, 6, and 8 µM (HVLP335S); 0.05, 0.1, 0.2, 0.2, 0.4, 0.6, 1, 2, 4, and 6 µM (HVLP351S); 0.1, 0.2, 0.2, 0.5, 0.75, 1, 2, 4, 7, and 10 µM (HVLP3103S); 4, 8, 8, 16, 32, 64, 120, 240 nM (HVLP324S); 0.1, 0.2, 0.4, 0.8, 1.5, 3, 6, 12 µM (HVLP325S); 2, 4, 8, 16, 16, 32, 64, 120, 240 nM (HVLP342S). The calculated $K_D$s are recorded in Table 4.

FIG. 9A compares the protease resistance profiles of wild-type $V_L$s (open circles) to those of Cys mutant $V_L$s (closed circles) in different ratio of protease to protein. In FIG. 9B, a plot of % protease resistance versus $T_m$ for wild-type (open circles) versus Cys mutant (closed circles) $V_L$s is shown.

FIG. 11 shows construction of a synthetic HVLP324S library. Amino acid sequence of HVLP324S (SEQ ID NO: 10), a human $V_L$ scaffold used for library construction, was numbered according to Kabat system (Kabat et al., 1991). Amino acid positions in the CDRs (1, 2, and 3) to be randomized were underlined. Non-canonical Cys residues were marked by dots. HVLP324S codons in the CDRs selected for in vitro mutagenesis are shown along with their corresponding randomization codons. Amino acid position 28 (on CDR1) was restricted to Ser or Gly codons (shown as RGC) and position 54 (on CDR2) was restricted to Arg or Leu codons (shown as CKN). For CDR3 mutagenesis, 3 oligonucleotides with various lengths ($V_L$24-CDR3/3a/3b; see Table 6, Example 8) were used, creating CDR3 lengths of 9, 10, or 11 amino acids. In compliance with IUPAC nomenclature, the following letters were used to designate degenerate nucleic acids at various positions within the oligonucleotides, wherein N: A, T, G, or C nucleotides; R: A or G nucleotides; K: T or G nucleotides. Sequences from top to bottom: HVLP324S is SEQ ID NO: 10; amino acid sequence of HVLP324S CDR1 is amino acids 24-34 of SEQ ID NO: 10; nucleotide sequence of HVLP324S CDR1 is SEQ ID NO: 109; nucleotide sequence of HVLP324S CDR1 randomization is nucleotides 18-51 of SEQ ID NO: 87; amino acid sequence of HVLP324S CDR2 is amino acids 50-56 of SEQ ID NO: 10; nucleotide sequence of HVLP324S CDR2 is SEQ ID NO: 110; nucleotide sequence of HVLP324S CDR2 randomization is nucleotides 18-39 of SEQ ID NO: 88; amino acid sequence of HVLP324S CDR3 is amino acids 89-97 of SEQ ID NO: 10; nucleotide sequence of HVLP324S CDR3 is SEQ ID NO: 111; nucleotide sequence of the top HVLP324S CDR3 randomization is nucleotides 18-45 of SEQ ID NO: 89; nucleotide sequence of the middle HVLP324S CDR3 randomization is nucleotides 18-48 of SEQ ID NO: 90; nucleotide sequence of the bottom HVLP324S CDR3 randomization is nucleotides 18-51 of SEQ ID NO: 91.

FIG. 13 shows amino acid sequences of anti-human lysozyme and anti-human serum albumin $V_L$s. Amino acid sequences of HVLP324S (SEQ ID NO: 10) are aligned with 8 anti-human lysozyme $V_L$s and 1 anti-human serum albumin $V_L$ selected for detailed biophysical analysis. The CDRs and FRs were designated by Kabat numbering (Kabat et al., 1991). Sequences from top to bottom: HVLP324S is SEQ ID NO: 10; HVLHLNN is SEQ ID NO: 99; HVLHLDS is SEQ ID NO: 100; HVLHLRN is SEQ ID NO: 101; HVLHLNE is SEQ ID NO: 102; HVLHLAQ is SEQ ID NO: 103; HVLHLEM is SEQ ID NO: 104; HVLHLQI is SEQ ID NO: 105; HVLHLYS is SEQ ID NO: 106; and HVLHSA1 is SEQ ID NO: 107.

FIG. 14A shows SUPERDEX™ 75 size exclusion chromatography (SEC) of anti-human lysozyme and anti-human serum albumin $V_L$s. For each chromatogram, background absorbance was subtracted and all peaks were normalized with respect to the monomeric peak (arrowheads) which was set at 100%. Peaks to the left of the monomeric peak are regarded as aggregating peak. % aggregate and % monomers values were calculated by the area integration of chromatograms as described. FIG. 14B shows thermal unfolding transition curves of anti-human lysozyme and anti-human serum albumin $V_L$s. The plot of fraction folded versus temperature was obtained as described previously. Temperatures corresponding to the midpoint of unfolding transition curves ($F_{0.5}$) were taken as the melting temperatures ($T_m$s). The $T_m$ range is shown by a doubleheaded arrow. FIG. 14C shows correlation curve of $T_m$ versus % monomer. The data was plotted analyzed with Graphpad Prizm (version 4.02).

FIG. 16A shows elution profiles of anti-human lysozyme $V_L$s following purification by immobilized-metal affinity chromatography (IMAC). Eluted peaks corresponding to the purified $V_L$s are marked by a rectangular box. mAU, milli-absorbance unit. FIG. 16B shows SDS-PAGE profiles of IMAC-purified $V_L$s under reducing (+DTT) condition. The purified $V_L$s were dialyzed in phosphate-buffered saline (PBS) before analysis by SDS-PAGE. Asterisk denotes the $V_L$ which have lost their His tag. Protein standards (lane M) are labelled with their respective molecular weights in kDa.

DETAILED DESCRIPTION OF THE INVENTION

Figure 2A:
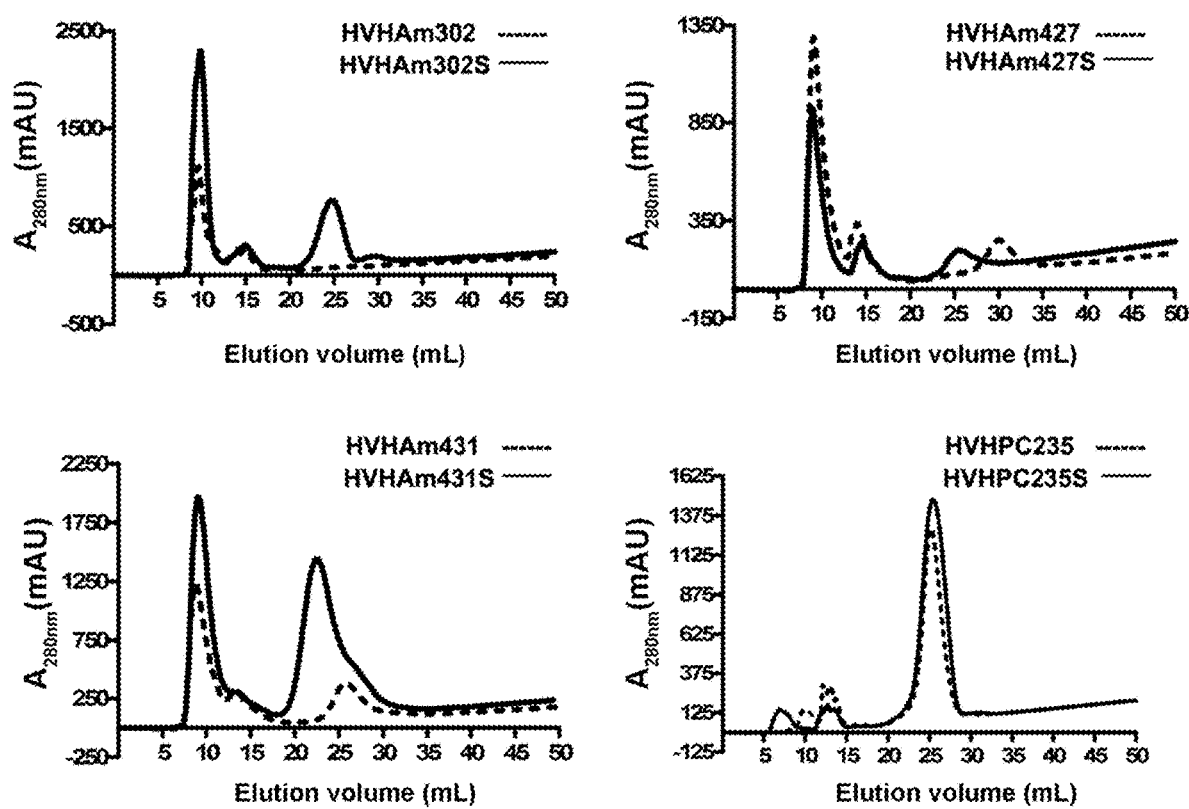
FIG. 2A shows elution profiles of $V_H$s from IMAC (immobilized-metal affinity chromatography) purification. Wild-type and mutant $V_H$s are indicated by dotted and closed line, respectively. The peaks that elute at or after 20 mL contains purified $V_H$s.

The present invention relates to engineering of immunoglobulin domains. More specifically, the present invention is directed to engineering of immunoglobulin domains to improve biophysical properties of the immunoglobulin. Compositions of matter and methods of making and using such compositions are provided.

The present invention provides a composition comprising a polypeptide comprising a $V_H$ or $V_L$ scaffold comprising one or more than one non-canonical disulfide bond in the framework region (FR), wherein the non-canonical disulfide bond provides improved stability and non-aggregation of the polypeptide. In one embodiment the polypeptide is a $V_H$ or $V_L$ scaffold. In one embodiment, the polypeptide comprises the sdAb fragment of a $V_H$ or $V_L$ domain. The sdAb may be derived from a $V_H$ region, a $V_H H$ region or a $V_L$ region as described herein.

The immunoglobulin scaffold may comprise the variable region of a heavy chain ("$V_H$"). In one embodiment the $V_H$ is derived from the $V_H 1$, the $V_H 2$ or the $V_H 3$ family. In one embodiment the $V_H$ may be of the $V_H 3$ family. Alternatively, the immunoglobulin scaffold may be a variable region of a light chain ("$V_L$"). In one embodiment the $V_L$ may be of the kappa or lambda family. In one embodiment the immunoglobulin scaffold is a non-human animal. In one embodiment, the non-human animal includes all vertebrates, especially vertebrates selected from avians, amphibians, reptiles, mammals, camelids, chicken, rat, mouse, rabbit, goat, sheep, cow, cat, dog, horse, or nonhuman primates. In one embodiment the immunoglobulin scaffold is human. In one embodiment the immunoglobulin scaffold is camelid. In one embodiment, the camelid species is selected from the group consisting of llama, alpaca and camel. In one embodiment, the camelid scaffold is derived from any one or more of a $V_H$ region, a $V_L$ or a $V_H H$ region.

In one embodiment the immunoglobulin scaffold is "humaneered" (also alternatively termed "humanized"), i.e., a sdAb that originated from a species other than human that has had immunogenic or potentially immunogenic amino acid residues replaced with amino acids that are less immunogenic or not immunogenic in the context of a sdAb administered to a human subject. Any method known in the art for creating humaneered antibodies are contemplated in the invention, including but not limited to humaneering technology of Kalobios. Note that when a scaffold is humaneered, an immunogenic amino acid residue may be replaced by any other less immunogenic amino acid residue regardless of whether or not this constitutes a conserved amino acid change. It is understood that humaneered scaffolds of the invention retain the non-canonical Cys residues described herein, as well as any native (canonical) disulfide bonds.

As used herein, the term "$V_H$" or "$V_L$", also referred to herein as "$V_H$ or $V_L$ domains" refer to the variable region of an antibody heavy chain or an antibody light chain, respectively. In one embodiment, the $V_H$ or $V_L$ domain is in the format of a "single domain antibody" (sdAb). As used herein, "sdAb" refers to a single immunoglobulin domain that retains the immunoglobulin fold; i.e., it is a variable domain in which up to three complementarity determining regions (CDR) along with up to four framework regions (FR) form the antigen-binding site. The CDR of the $V_H$ or $V_L$ variable domain are referred to herein as CDR1, CDR2, and CDR3. The FRs of the $V_H$ or $V_L$ variable domain are referred to herein as FR1, FR2, FR3 and FR4. Various schemes exist for identification of the complementarity-determining regions, the two most common being those of Kabat and of Chothia and Lesk. Kabat et al (1991) define the "complementarity-determining regions" (CDR) based on sequence variability at the antigen-binding regions of the $V_H$ and/or $V_L$ domains. Chothia and Lesk (1987) define the "hypervariable loops" (H or L) based on the location of the structural loop regions in the $V_H$ and $V_L$ domains. As these individual schemes define CDR and hypervariable loop regions that are adjacent or overlapping, those of skill in the antibody art often utilize the terms "CDR" and "hypervariable loop" interchangeably, and they may be so used herein. The majority of the sequence variability in variable domains ($V_H$ or $V_L$) occurs in the CDR/loops; the regions outside the CDR/loops are referred to as the framework regions (FR). The FR provide structural integrity to the variable domain and ensure retention of the immunoglobulin fold. The FR and CDR/loops are defined herein according to the Kabat numbering system (Kabat et al, 1991). In one embodiment, the numbering of the positions with the FR1, CDR1, FR2, CDR2, FR3, CDR3 and FR4 regions of the polypeptides described herein are as provided in FIG. 1A for a $V_H$ domain and as provided in FIG. 1B for a $V_L$ domain.

Human $V_H$ or $V_L$ domains may be obtained from human Ig heavy or light chain sequences (Holliger, and Hudson, 2005; Holt, et al., 2003; Jespers et al, 2004; To et al, 2005). Similar techniques are known in the art for obtaining $V_H$ or $V_L$ domains from non-human species. Furthermore, the inventive $V_H$ and $V_L$ domains of the present invention include recombinantly produced $V_H$ or $V_L$, as well as those $V_H$ or $V_L$ generated through further modification of such $V_H$ or $V_L$ by affinity maturation, stabilization, solubilization (e.g., camelization), or other methods of antibody engineering. Also encompassed by the present invention are homologues, derivatives, or variants that retain or improve the stability and non-aggregation characteristics of the $V_H$ or $V_L$.

The invention provides novel $V_H$ or $V_L$ domains that comprise a scaffold comprising non-canonical Cys resides. As used herein a "scaffold" or alternatively an "immunoglobulin scaffold" comprises the framework regions (FR1, FR2, FR3, and FR4) of the $V_H$ or $V_L$, wherein the framework provides the polypeptide backbone for the various CDRs (CDR1, CDR2, CDR3). As used herein, the term "scaffold" ignores the CDR regions for purposes of describing the framework portion of composition of the invention.

The immunoglobulin scaffold described herein may comprise a polypeptide sequence comprising at least two non-canonical Cys residues introduced into the framework regions FR2 and FR3 of an antibody variable region. In one embodiment, the polypeptide comprises a Cys residue at a position selected from residues 47 to 49 of a $V_H$ FR2 regions and a Cys residue at a position selected from residues 69 to 71 of a $V_H$ FR3 regions of a $V_H$ sdAb domain. In one embodiment, the polypeptide comprises a Cys residue at a position selected from residues 46 to 49 of a $V_L$ FR2 regions and a Cys residue at a position selected from residues 62 to 66 of a $V_L$ FR3 regions of a $V_L$ sdAb domain. As used herein, "introduced" or "introducing" means incorporating a change into the polypeptide composition or the nucleotide sequence encoding the polypeptide composition using any suitable method known to one skilled in the art, and especially including recombinant technology. In one embodiment, Cys residues are introduced into the $V_H$ and/or $V_L$ construct by replacing an existing codon in a gene, a coding sequence and/or an mRNA with a codon that is specific for a cysteine residue.

In one embodiment, the inventive composition comprises an immunoglobulin scaffold selected from a $V_H$ or a $V_L$ scaffold, wherein the $V_H$ scaffold comprises at least one non-canonical disulfide bond in the FR, wherein the non-canonical disulfide bond is formed between Cys residues introduced at positions 49 and 69, based on Kabat numbering; and the $V_L$ scaffold comprises at least one non-canonical disulfide bond in the FR, wherein the non-canonical disulfide bond is formed between Cys residues introduced at positions 48 and 64, based on Kabat numbering.

As used herein, an "inventive" $V_H$ construct or sdAb fragment comprises at least one non-canonical disulfide bridge comprising at least a Cys residue at position 49 and at least a Cys residue at position 69.

As used herein, an "inventive" $V_L$ construct or sdAb fragment comprises at least one non-canonical disulfide bridge comprising at least a Cys residue at position 48 and at least a Cys residue at position 64.

In one embodiment, the polypeptide comprises at least a Cys residue at position 49 and at least a Cys residue at position 69 of a $V_H$ domain. In one embodiment, the inventive $V_H$ domain comprises a sdAb fragment. In one embodiment, the invention provides an expression library comprising the inventive $V_H$ immunoglobulin scaffold, wherein the immunoglobulin scaffold further comprise a multiplicity of CDR sequences. In one embodiment, the invention provides a recombinant library comprising the inventive $V_H$ immunoglobulin scaffold and a multiplicity of suitable CDR sequences so as to provide libraries with diversities of at least $10^5$, at least $10^6$, at least $10^7$, at least $10^8$, at least $10^9$ or more than $10^9$ clones per library. In one embodiment, the position of the CDR regions of the inventive $V_H$ sdAb fragment selected from the group of SEQ ID NOS: 2, 4, 6 and 8 are at the positions provided in FIG. 1A and those of SEQ ID NOS:70 to 83 are at the position provided for the corresponding wild type sequences in FIG. 2 of the PCT publication WO2006/099747.

In one embodiment, the polypeptide comprises at least a Cys residue at position 48 and at least a Cys residue at position 64 of a $V_L$ domain. In one embodiment, the inventive $V_L$ domain comprises a sdAb fragment. In one embodiment, the invention provides an expression library comprising the inventive $V_L$ sdAb fragment, wherein the inventive sdAb fragments comprise a multiplicity of CDR sequences. In one embodiment, the invention provides a recombinant library comprising the inventive $V_L$ immunoglobulin scaffold and a multiplicity of suitable CDR sequences so as to provide libraries with diversities of at least $10^5$, at least $10^6$, at least $10^7$, at least $10^8$, at least $10^9$ or more than $10^9$ clones per library. In one embodiment, the position of the CDR regions of the inventive $V_L$ sdAb fragment selected from the group of SEQ ID NOS: 10, 12, 14, 16, 18, 20, 22 and 24 are at the positions provided in FIG. 1B.

In one embodiment, the CDR residues of the inventive polypeptides may be any suitable sequence and may have a variable number of residues other than the number provided in FIGS. 1A and 1B. Each of CDR1, CDR2 and CDR3 may vary in sequence and in length according to guidelines known to those skilled in the antibody arts. Without wishing to be limited to any one specific reference, exemplary guidelines are provided in the Kabat and the Chothia and Lesk publications cited herein. In a nonlimiting example, the design and construction of a phage library based on the HVLP324S scaffold is provided in FIG. 11 and in Example 8 and the library is characterized in Example 9.

The $V_H$ or $V_L$ compositions of the present invention provide scaffolds in the construction of additional libraries or antibodies. In one embodiment the framework regions (FR1, FR2, FR3, and FR4) of the $V_H$ or $V_L$ may be used to carry various CDRs, i.e., wherein the FR are as provided and wherein the sequence and number of residues of the CDR region are as provided or vary at one or more, or at all, of the CDR-specific residues. In this manner, synthetic $V_H$ or $V_L$ libraries may be constructed on single scaffolds by inserting suitable oligonucleotides comprising randomized sequences to provide randomized CDR/loops. Such libraries may be display libraries such as phage display, ribosome display, or yeast display. This approach is routine in the art and has been described in many publications (for example, but not limited to Arbabi-Ghahroudi et al., 2009a and references therein). The libraries may optionally be used for further antibody engineering or for in vitro affinity maturation (Davies and Riechmann, 1996b; Yau et al., 2005). Alternatively, an existing library based on a naturally-occurring sdAb can be used to engineer disulfide linkage(s) into every member of the library by splice overlap extension-polymerase chain reaction (SOE-PCR) (Arbabi-Ghahroudi, et al., 2010 and references therein; Ho et al., 1989) or other methods (Kunkel et al., 1987; Sidhu et al., 2000).

In yet another alternative, the $V_H$ or $V_L$ may be used as a scaffold to incorporate specific CDR sequences; for example, and without wishing to be limiting in any manner, a humanized antibody may be constructed from any non-human antibody by using recombinant technology to further comprise the non-canonical disulfide bridge according to the methods provided herein. This construct may then be further modified to bind a specific target by inserting the appropriate CDR coding segments (responsible for the desired binding properties, and which may vary in sequence and in length according to guidelines cited herein and known to those skilled in the antibody arts) into the humanized antibody scaffold according to the present invention. As would be known to a person of skill in the art, these techniques are achieved through standard cloning and recombinant DNA methods using an appropriate vectors and expression in cells (mammalian or otherwise). Such methods and techniques are well-known to those of skill in the art, and are not described here.

The $V_H$ or $V_L$ scaffolds of the present invention comprise one or more than one non-canonical disulfide bond in the framework regions. A disulfide bond is a covalent force that stabilizes proteins through coupling of two thiol groups between cysteine residues (Betz, 1993). By "non-canonical", it is meant that the disulfide bond is not found in naturally-occurring human $V_H$ and $V_L$, but rather is introduced using molecular engineering techniques. The naturally-occurring (or "canonical") disulfide bond connecting two β-sheets within a variable domain is highly conserved in $V_H$ and $V_L$ superfamilies (Amzel and Poljak, 1979; Williams and Barclay, 1988). The conserved disulfide bonds form between Cys22 and Cys92 in $V_H$s and Cys23 and Cys88 in $V_L$s, wherein the residues are numbered according to Kabat (see FIG. 1). In the present invention, one or more than one additional non-canonical disulfide bond is engineered into the $V_H$ or $V_L$ domain. Preferably, the engineered disulfide bond forms between a Cys from a first beta sheet and a Cys from a nearby second beta sheet in the immunoglobulin fold. For example, this can be accomplished by introducing an appropriate number of Cys pair(s) at locations in the framework regions that will form a disulfide bond in the expressed and fully folded protein. The Cys residues may be introduced into framework regions that are adjacent in the three-dimensional structure of the variable domain. For example, and without wishing to be limiting in any manner, Cys residues could be introduced into the FR2 beta sheet region and the FR3 beta sheet region. The Cys residues are introduced into the adjacent framework regions at locations that are within range for coupling of the thiol groups. For example, and without wishing to be limiting in any manner, Cys residues may be introduced at one of positions 47-49 (3 positions) and one of positions 67-71 (5 positions) for $V_H$, or at one of positions 46-49 (4 positions) and one of positions 62-66 (5 positions) for $V_L$ (based on Kabat numbering), providing that the respective Cys pairs are within sufficient proximity so as to form a disulfide bond. In a further, non-limiting example, the Cys residues may be introduced at positions 49 and 69 for $V_H$, and/or 48 and 64 for $V_L$ (based on Kabat numbering).

The Cys may be introduced into the framework regions of $V_H$ or $V_L$ domains using any suitable method known in the art. Without wishing to be limiting, the Cys may be introduced by point-mutation or insertion through recombinant DNA methods; for example and without wishing to be limiting in any manner, the Cys may be introduced using splicing by overlap extension (SOE)-PCR (Arbabi-Ghahroudi, et al., 2010 and references therein; Ho et al., 1989).

The one or more than one non-canonical disulfide bond in the $V_H$ and/or $V_L$ scaffolds lends improved stability to and non-aggregation of the antibody. Non-aggregation refers to the molecule existing in a monomeric state; for example, and without wishing to be limiting in any manner, monomers give essentially one peak with size exclusion chromatography (SEC). Aggregating molecules form dimers, trimers, and higher order aggregates. Stability of an antibody includes biophysical characteristics such as thermostability, thermal and chemical refolding efficiency, and protease resistance. Other factors to be considered when evaluating the $V_H$ or $V_L$ scaffolds of the present invention include expression levels and solubility. As is known in the art, solubility refers to the number of molecules per volume (e.g., in molarity or mg/mL) that may be dissolved in a liquid prior to precipitation; in the case of sdAbs, and in the context of the present invention, the number of monomeric molecules is of particular importance.

The addition of a non-canonical disulfide bond may improve one or more than one of the aforementioned biophysical characteristics. For example, and without wishing to be bound by theory, the introduction of a non-canonical disulfide bond into a $V_H$ or $V_L$ domain may improve stability (for example, higher melting temperature and protease resistance, by stabilizing the framework); and/or improve non-aggregation (by reducing inter-molecular interactions and formation of aggregates).

The $V_H$ or $V_L$ scaffold into which non-canonical disulfide bonds are introduced may be of any suitable germline origin. For example, and without wishing to be limiting in any manner, the $V_L$ may be of the lambda or kappa family, for example kappa 1 or kappa 3, or its composition may be derived from various combinations of V and J segment germline sequences. In another example, and without wishing to be limiting in any manner, the $V_H$ may be of the $V_H1$, the $V_H2$, the $V_H3$, the $V_H4$, the $V_H5$, the $V_H6$ or the $V_H7$ family, or its composition may be derived from various combinations of V, D and J segment germline sequences (To et al., 2005; V BASE database of the MRC Centre for Protein Engineering). In one embodiment, the $V_H$ may be of the $V_H3$ family.

In one embodiment, the $V_H$ or $V_L$ scaffolds of the present invention may include, but are not limited to scaffolds comprising the framework regions of sequences selected from the group consisting of (HVHAm302S; SEQ ID NO: 2)
QVQLVESGGGLIKPGGSLRLSCAASGDTVSDESMTWVRQAPGKGLEWVC

AISSSGGSTYYADSVKGRFTCSRDNSKNTVYLQMNSLRAEDTAVYYCVT

DNRSCQTSLCTSTTRSWGQGTMVTVSS;

(HVHAm427S; SEQ ID NO: 4)
QVQLVESGGGLIKPGGSLRLSCAASGVTLSPECMAWVRQAPGKGLEWVC

AISSSGGSTYYADSVKGRFTCSRDNSKNTVYLQMNSLRAEDTAVYYCVS

CEGENAFWGQGTMVTVSS;

(HVHAm431S; SEQ ID NO: 6)
QVQLVESGGGLIKPGGSLRLSCAASGYTVSSECMGWVRQAPGKGLEWVC

AISSSSGSTYYADSVKGRFTCSRDNSKNIVYLQMNSLRAEDTAVYYCVR

DSKNCHDKDCTRPYCSWGQGTMVTVSS;

(HVHPC235S; SEQ ID NO: 8)
QVQLVESGGGLIKPGGSLRLSCAASGFSVISESMTWVRQAPGKGLEWVC

AISSSGGSTYYADSVKGRFTCSRDNSKNTVHLQMNSLRAEDTAVYYCAA

KKIDGARYDYWGQGTMVTVSS (HVLP324S; SEQ ID NO: 10)
DIQMTQSPSSLSASVGDRVTITCRASQSISTYLNWYQQKPGKAPKLLC

FAASTLQSGVPSRFSCSGSGTDFTLTISNLQPEDFATYYCQQSYSTPR

TFGHGTKVTVL;

(HVLP325S; SEQ ID NO: 12)
EIVLTQSPTTLSLSPGERATLSCRASQSVGRYLAWYQQRPGQAPRLLC

FDTSNRAPGVPARFSCRGSGTLFTLTISSLEPEDSAVYFCQQRSSGLT

FGGGTKVTVL;

(HVLP335S; SEQ ID NO: 14)
EIVMTQSPATLSLSPGERATLSCRASQSVSSSSLAWYQQKPGQAPRLLC

YGTSNRATGIPDRFSCSGSGTHFTLTINRLEPGDFAVYYCQQYGSSPRT

FGQGTKVEIK;

(HVLP342S; SEQ ID NO: 16)
DIQMTQSPSSLSASVGDRVTITCRASQDIRTDLDWFQQRPGRAPHRLIYGASSLQGGVPSRFSGSGSGTEFTLTISGLQPEDFATYYCLQHHTYPRTFGLGTKVTVL;

(HVLP351S; SEQ ID NO: 18)
EIVMTQSPVTLSLSPGERATLSCRASQSVGTSLAWYQQKPGQAPRLLIYDASNRATGISARFSGSGSGTDFTLTISSLEPEDFAVYYCQQRYNWPRTFGGGTKVTVL;

(HVLP364S; SEQ ID NO: 20)
ETTLTQSPATLSVSPGERATFSCRASQSVSNNLAWYQQKPGQAPRLLIYGASSRTTGIPDRFSGSGSGTDFTLTISRLEPEDFAVYYCQQYDTSPRTFGQGTKVEIK;

(HVLP389S; SEQ ID NO: 22)
QSVVTQPPSVSAAPGQRVTISCSGSSYNIGENSVSWYQQLPGTAPKLLIYGNDKRPSGIPDRFSCSKSGTSATLGITGLQTGDEADYYCGTWDSNLRASVFGGGTKVTVL;

(HVLP3103S; SEQ ID NO: 24)
ETTLTQSPGTLSLSPGERATLSCRASQSVRNNLAWYQQRPGQAPRLLIYGASTRATGIPARFSGSGSGTDFTLTISSLQVEDVAVYYCQQYYTTPKTFGQGTKVEIK, (SEQ ID NO: 70)
EVQLVESGGGLVQPGGSLRLSCAASGFTFSSYAMSWVRQAPGKGLEWVCAISGSGGSTYYADSVKGRFTCSRDNSKNTLYLQMNSLRAEDTAVYYCAKDEPRSVSGLRGVVDSWGRGTLVTVSS (SEQ ID NO: 71)
QVQLQESGGGLVQPGGSLRLSCAASGFTFSSYAMSWVRQAPGKGLEWVCAISGSGGSTYYADSVKGRFTCSRDNSKNTLYLQMNSLRAEDTAVYYCGTDMEVWGKGTTVTVSS (SEQ ID NO: 72)
QLQLQESGGGVVQPGRSLRLSCAASGFTFSSYAMSWVRQAPGKGLEWVCAISGSGGSTYYADSVKGRFTCSRDNSKNTLYLQMNSLRAEDTAVYYCAKDGKGGSSGYDHPDYWGQGTLVTVSS (SEQ ID NO: 73)
QLQLQESGGGLVQPGGSLRLSCAASGFTFSSYAMSWVRQAPGKGLEWVCAISGSGGSTYYADSVKGRFTCSRDNSKNSLYLQMNSLGAEDTAVYYCARSWSGSSYGGDLDSWGQGTLVTVSS (SEQ ID NO: 74)
QVQLVESGGGLIKPGGSLRLSCAASGFTFSNYAMSWVRQAPGKGLEWVCAISSSGGSTYYADSVKGRFTCSRDNSKNTVYLQMNSLRAEDTAVYYCVREEYRCSGTSCPGAFDIWGQGTMVTVSS (SEQ ID NO: 75)
EVQLVESGGTLVQPGGSLRLSCAASGFTFINYAMSWVRQAPDKGLDWVCTISNNGGATYYADSVKGRFTCSRDNSNNTLYLQMNSLRPDDTAVYYCAKGPINTGRYGDWGQGTLVTVSS (SEQ ID NO: 76)
QVQLVQSGGGLVQPGRSLRLSCAASGFAFSSYAMSWVRQAPGKGLEWVCAISGGGDHTYYADSVKGRFTCSRDNSKNTLYLQMNSLRAEDTAVYYCAKEGMVRGVSSAPFDYWGQGTLVTVSS (SEQ ID NO: 77)
EVQLVQSGGGLVQPGRSLRLSCAASGFTFDDYAMHWVRQAPGKGLEWVCGISGSGASTYYADSVKGRFTCSRDNSKNTLYLQMNSLRAGDTALYYCARQSITGPTGAFDVWGQGTMVTVSS (SEQ ID NO: 78)
QLQLQESGGGLVQPGGSLRLSCAASGFTFSSYAMSWFRQAPGKGLEWVCFIRSKAYGGTTEYAASVKGRFTCSRDDSKSIAYLQMNSLRAEDTAMYYCARRAKDGYNSPEDYWGQGTLVTVSS (SEQ ID NO: 79)
QVQLVESGGGLVKPGGSLRLSCAASGFTFSNAWMTWVRQAPGKGLEWVCRIKTKTDGGTTDYAAPVKGRFTCSRDDSKNTLYLQMNSLKTEDTAVYYCTTDRDHSSGSWGQGTLVTVSS (SEQ ID NO: 80)
DVQLVQSGGGLVKPGGSLRLSCTASGFPFSNAWMSWVRQAPGKGLEWVCRITSKTDGGITDYVAPVKGRFTCSRDDSKNTLYLQMNSLKTEDTAVYYCTTDQANAFDIWGQGTMVTVSS (SEQ ID NO: 81)
QMQLVQSGGGVVQPGGSLRLSCAASGFTVSSSRMSWFRQAPGMGLEWVCVIYSGGSTYYADSVRGRFSCSRDNSKNTLYLQMNSLRAEDTALYYCAREREGAVTREDWGQGTLVTVSS (SEQ ID NO: 82)
QVQLVQSGGGLVKPGGSLRLSCAASGFTFSDYYMSWVRQAPGKGLEWVCFIYSGGSTYYADSVKGRFTCSRDNSKNTLYLQMNSLRAEDTAVYYCARESRVGGGAFDIWGQGTMVTVSS
and (SEQ ID NO: 83)
QVQLVQSGGGVVQPGRSLRLSCAASGFIVDGYAMHWVRQAPGQGLEWVCVTNNGGSTSYADSVKGRFTCSRDNSKNTVYLQMNSLRAEDTAVYYCARQSITGPTGAFDIWGQGTMVTVSS or sequences substantially identical thereto, or fragments thereof, with the proviso that the substantially identical sequence, or fragments thereof, retains both the canonical and non-canonical disulfide bonds and wherein the sequence in the regions of the CDRs may be any suitable sequence and may have a suitable but variable number of residues in each of CDR1, CDR2 and CDR3. In the case of SEQ ID Nos: 2, 4, 6, 8, 10, 12, 14, 16, 18, 20, 22 and 24, the residues that comprise the CDRs are as provided in FIGS. 1A and 1B. In the case of SEQ ID Nos: 70 through 83, the residues that comprise the CDRs are as provided in the corresponding wild type clones as provided in FIG. 2 of PCT publication WO2006/099747, wherein said FIG. 2 is incorporated herein by reference. The substantially identical sequences should also retain or improve the stability and non-aggregation characteristics of the $V_H$ or $V_L$. As noted throughout the text, the inventive scaffolds are not limited to the residues listed in the CDR regions, which are as delimited in FIGS. 1A and 1B for the clones listed herein.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics, BLAST-P, Blast-N, or FASTA-N, or any other appropriate software that is known in the art. In one embodiment, calculation of percent identity is limited to comparison of the framework regions and disregards the residues within the CDRs. In one embodiment, calculation of percent identity compares all residues in a polypeptide, including both those of the framework regions and the CDRs.

As noted throughout the text, the inventive scaffolds are not limited to the residues listed in the CDR regions, which are as delimited in FIGS. 1A and 1B for the clones listed herein as SEQ ID Nos: 2, 4, 6, 8, 10, 12, 14, 16, 18, 20, 22 and 24; and are delimited in FIG. 2 of PCT publication WO2006/099747 for the wild type sequences corresponding to the clones listed herein as SEQ ID Nos: 70 through 83.

The substantially identical sequences of the present invention may be at least 90% identical; in another example, the substantially identical sequences may be at least 90, 91, 92, 93, 94, 95, 96, 97, 98, 99, or 100% (or any percentage therebetween) identical at the amino acid level to sequences described herein. In a further embodiment, a substantially identical sequence may contain one, two, three or four amino acid differences in the framework region when aligned with an inventive composition provided herein. Importantly, the substantially identical sequences retain the stability and biophysical properties of the reference sequence. In a non-limiting embodiment, the difference in sequence identity may be due to conservative amino acid mutation(s). In one embodiment, the substantially identical sequences consist of the residues comprising FR1, FR2, FR3 and FR4 and does not consider the residues comprising any one or more of CDR1, CDR2 and CDR3.

The $V_H$ or $V_L$ scaffolds may be included as part of larger antibody protein or fragments such as one or more of a sdAb, scFv, Fab, F(ab)$_2$ and/or mature immunoglobulin, including but not limited to an IgG, IgE, and/or IgM, for the purpose of increasing their biophysical properties such as non-aggregation, stability, expression level, and solubility. As used herein, a "mature immunoglobulin" comprises a light chain, said light chain comprising a variable and a constant region, and a heavy chain, said heavy chain comprising a variable and a constant region. In one embodiment, the mature immunoglobulin is selected from the group consisting of an IgG1, IgG2, IgG3, IgG4, IgE, and/or IgM. In one embodiment the introduced sequence of this larger antibody construct is human or is humaneered. The above approach can also be applied to $V_H$ and $V_L$ derivatives such as fusion constructs made by fusions of $V_H$s and $V_L$s to other polypeptides such as toxins, $V_H$s and/or $V_L$s with the same or different specificity, Fc domains, etc. for the purpose of increasing their biophysical properties such as solubility, non-aggregation, expression level and stability.

The $V_H$ or $V_L$ scaffolds of the present invention may also be fused to additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection tag (for example, but not limited to c-Myc), a purification tag (for example, but not limited to a His$_5$ or His$_6$), an Fc fragment, or a combination thereof. In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags.

The $V_H$ or $V_L$ scaffolds of the present invention may also be in a multivalent display. Multimerization may be achieved by any suitable method known in the art. For example, and without wishing to be limiting in any manner, multimerization may be achieved using self-assembly molecules as described in Zhang et al (2004a; 2004b) and WO2003/046560. The described method produces pentabodies by expressing a fusion protein comprising the $V_H$ or $V_L$ scaffold of the present invention and the pentamerization domain of the B-subunit of an $AB_5$ toxin family (Merritt and Hol, 1995); the pentamerization domain assembles into a pentamer, through which a multivalent display of the antibody or fragment thereof is formed. Additionally, the pentamerization domain may be linked to the $V_H$ or $V_L$ scaffold using a linker; such a linker should be of sufficient length and appropriate composition to provide flexible attachment of the two molecules, but should not hamper the biophysical properties of the $V_H$ or $V_L$ scaffold.

Other forms of multivalent display are also encompassed by the present invention. For example, and without wishing to be limiting, the $V_H$ or $V_L$ scaffold may be presented as at least a dimer, a trimer, tetramer, pentamer, hexamer, heptamer, octamer, or any other suitable oligomer. This may be achieved by methods known in the art, for example direct linking connection (Nielson et al, 2000), c-jun/Fos interaction (de Kruif and Logtenberg, 1996), "Knob into holes" interaction (Ridgway et al, 1996) or sequential cloning of repeating units of the coding region of the inventive clone and suitable short polypeptide linkers known in the art.

Another method known in the art for multimerization is to dimerize the $V_H$ or $V_L$ composition using an Fc domain. When applied in vivo, monomeric sdAb are cleared quickly from the circulation (Bell et al., 2010). To solve this problem and to give $V_H$ or $V_L$ the ability to induce immune response after antigen binding, $V_H$ or $V_L$ scaffolds may be fused to an antibody constant region fragment ("Fc") to generate chimeric heavy chain antibodies (Bell et al., 2010). In this approach, the Fc gene in inserted into a vector along with the $V_H$ or $V_L$ gene to generate a sdAb-Fc fusion protein (Bell et al, 2010; Iqbal et al, 2010); the fusion protein is recombinantly expressed then purified. Such antibodies are easy to engineer and to produce (Zhang et al., 2009), can greatly extend the serum half life of $V_H$ or $V_L$, and may be excellent tumor imaging reagents (Bell et al., 2010). In one embodiment, the Fc portion is human.

The present invention also encompasses nucleic acid sequences encoding the molecules as described herein. In one embodiment, the nucleic acid comprises a sequence encoding an immunoglobulin scaffold selected from a $V_H$ or a $V_L$ scaffold, wherein the $V_H$ scaffold comprises at least one non-canonical disulfide bond in the FR formed between Cys residues introduced at positions 49 and 69, based on Kabat numbering; and the $V_L$ scaffold comprises at least one non-canonical disulfide bond in the FR formed between Cys residues introduced at positions 48 and 64, based on Kabat numbering. In one embodiment, the nucleic acid encodes any one or more of the sequences selected from SEQ ID NOS: 2, 4, 6, 8, 10, 12, 14, 16, 18, 20, 22, 24 and 70-83. In one embodiment, the nucleic acid sequence comprises any codon of the degenerate code that encodes the appropriate amino acid residue. In one embodiment, coding region of the nucleic acid sequence is codon optimized. In one embodiment, the nucleic acid is in an expression vector. In one embodiment, the expression vector is in a host cell or organism capable of expressing said nucleic acid.

As is well known to those of skill in the art, it is possible to improve the expression of a nucleic acid sequence in a host cell or organism by replacing the nucleic acids coding for a particular amino acid (i.e. a codon) with another codon which is better expressed in the host organism. One reason that this effect arises is due to the fact that different organisms show preferences for different codons. In particular, bacterial organisms and yeast organisms prefer different codons from plants and animals. The process of altering the sequence of a nucleic acid to achieve better expression based on codon preference is called codon optimization. Statistical methods have been generated to analyze codon usage bias in various organisms and many computer algorithms have been developed to implement these statistical analyses in the design of codon optimized gene sequences (Lithwick and Margalit, 2003). In one embodiment, the nucleic acid sequence may be codon-optimized for expression in mammalian cells. In one embodiment, the nucleic acid sequence may be codon-optimized for expression in various microorganisms. In one embodiment, the nucleic acid sequence is codon-optimized for expression in *E. coli*. In one embodiment, the nucleic acid sequence is codon-optimized for expression in yeast. In one embodiment, the nucleic acid sequence is codon-optimized for expression in yeast and for surface display of antibodies, i.e., shuttle between antibody phage display and antibody yeast display. The present invention also encompasses vectors comprising the nucleic acids as just described. Furthermore, the invention encompasses cells comprising the nucleic acid and/or vector as described.

The present invention further encompasses the $V_H$ or $V_L$ scaffold immobilized onto a surface using various methodologies; for example, and without wishing to be limiting, the $V_H$ or $V_L$ scaffold may be linked or coupled to the surface via His-tag coupling, biotin binding, covalent binding, adsorption, and the like. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, a film, or any other useful surface.

The present invention further provides an inventive $V_H$ or $V_L$ linked to a cargo molecule; the antibody or fragment thereof may deliver the cargo molecule to a desired site. The cargo molecule may be any type of molecule that may be use to diagnose, treat or detect a biomarker. In one embodiment, the cargo marker is a molecule that may reduce and/or inhibit the growth of targeted cells. In one embodiment, the targetted cells are cells associated with a proliferative disease. In one embodiment, the proliferative disease is a cancer, including various types of tumours, wherein the targeted cells express a marker recognized by the $V_H$ or $V_L$ domain portion of the invention. Thus, in one embodiment the cargo molecule is a therapeutic or diagnostic agent. In one embodiment the cargo molecule is linked to a therapeutic or diagnostic agent.

For example, and without wishing to be limiting in any manner, the therapeutic agent may be a radioisotope, which may be used for radioimmunotherapy; a toxin, such as an immunotoxin; a cytokine, such as an immunocytokine; a cytotoxin; an apoptosis inducer; an enzyme; or any other suitable therapeutic molecule known in the art. In the alternative, a diagnostic agent may include, but is by no means limited to a radioisotope, a paramagnetic label, a fluorophore, an affinity label (for example biotin, avidin, etc), fused to a detectable protein-based molecule, or any other suitable agent that may be detected by imaging methods. In a specific, non-limiting example, the antibody or fragment thereof may be linked to a fluorescent agent such as FITC or may genetically be fused to the Enhanced Green Fluorescent Protein (EGFP).

The antibody or fragment thereof may be linked to the cargo molecule using any method known in the art (recombinant technology, chemical conjugation, etc.).

The present invention also provides a method of improving stability of single domain antibodies, comprising introducing one or more than one non-canonical disulfide bond in the framework region. In one embodiment, the method comprises introducing at least two non-canonical Cys residues into the framework regions of the immunoglobulin of interest. In one embodiment, the two Cys residues replace residues in the FR2 and FR3 of an antibody variable region. In one embodiment, the method comprises introducing a Cys residue at a position selected from residues 47 to 49 of a $V_H$ FR2 regions and a Cys residue at a position selected from residues 69 to 71 of a $V_H$ FR3 regions of a $V_H$ sdAb domain. In one embodiment, the method comprises introducing a Cys residue at a position selected from residues 46 to 49 of a $V_L$ FR2 regions and a Cys residue at a position selected from residues 62 to 66 of a $V_L$ FR3 regions of a $V_L$ sdAb domain.

In one embodiment, the method comprises introducing at least one non-canonical Cys residue at position 49 and at least one non-canonical Cys residue at position 69 of a $V_H$ domain. In one embodiment, the method comprises introducing at least one non-canonical Cys residue at position 48 and at least one non-canonical Cys residue at position 64 of a $V_L$ domain.

In one embodiment, the method comprises the creation of an expression library comprising the inventive $V_H$ sdAb fragment comprising a disulfide bridge between non-canonical Cys residues at positions 49 and 69, wherein the inventive sdAb fragments comprise a multiplicity of CDR sequences. In one embodiment, the method comprises the creation of an expression library comprising the inventive $V_L$ sdAb fragment comprising a disulfide bridge between non-canonical Cys residues at positions 48 and 64, wherein the inventive sdAb fragments comprise a multiplicity of CDR sequences. Any suitable method known in the art for antibody library creation replacement of CDR sequences may be used. In one embodiment, the position of the CDR regions are as defined by Kabat. In one embodiment, the position of the CDR regions are as defined by Chothia and Lesk. In one embodiment, the expression library is codon optimized for expression in mammalian cells. In one embodiment, the expression library is codon optimized for expression in yeast. In one embodiment, the expression library is codon optimized for expression in E. coli.

In one embodiment, the mutations can be introduced by SOE-PCR approach (Arbabi-Ghahroudi et al., 2010 and reference therein; Ho et al., 1989) or by other method (Kunkel et al., 1987; Sidhu et al., 2000, Hussack et al., In press (c)). Alternatively, the genes for the mutants can be obtained commercially, either on their own or within the target cloning and expression vector (Kim et al., In press).

The present invention will be further illustrated in the following examples. However, it is to be understood that these examples are for illustrative purposes only and should not be used to limit the scope of the present invention in any manner.

Example 1: Cloning, Expression and Purification of Mutant $V_H$s and $V_L$s

Aggregating and non-aggregating $V_H$ and $V_L$ domains as well as their counterpart double cysteine mutants were cloned, expressed and purified. $V_H$ and $V_L$ utilized, as well as their corresponding Cys mutants, are listed in Table 1 and shown in FIGS. 1A and 1B.

TABLE 1

$V_H$ and $V_L$ and mutants constructed.

| $V_H$* | $V_H$ Cys mutant |
|---|---|
| HVHAm302 (SEQ ID NO: 1) | HVHAm302S (SEQ ID NO: 2) |
| HVHAm427 (SEQ ID NO: 3) | HVHAm427S (SEQ ID NO: 4) |
| HVHAm431 (SEQ ID NO: 5) | HVHAm431S (SEQ ID NO: 6) |
| HVHPC235 (SEQ ID NO: 7) | HVHPC235S (SEQ ID NO: 8) |
| HVHP44 | HVHP44S (SEQ ID NO: 70) |
| HVHB82 | HVHB82S (SEQ ID NO: 71) |
| HVHP421 | HVHP421S (SEQ ID NO: 72) |
| HVHP419 | HVHP419S (SEQ ID NO: 73) |
| HVHP430 | HVHP430S (SEQ ID NO: 74) |
| HVHP429 | HVHP429S (SEQ ID NO: 75) |
| HVHM41 | HVHM41S (SEQ ID NO: 76) |
| HVHM81 | HVHM81S (SEQ ID NO: 77) |
| HVHP428 | HVHP428S (SEQ ID NO: 78) |
| HVHP420 | HVHP420S (SEQ ID NO: 79) |
| HVHP414 | HVHP414S (SEQ ID NO: 80) |
| HVHP423 | HVHP423S (SEQ ID NO: 81) |
| HVHP413 | HVHP413S (SEQ ID NO: 82) |
| HVHP426 | HVHP426S (SEQ ID NO: 83) |

| $V_L$* | $V_L$ Cys mutant |
|---|---|
| HVLP324 (SEQ ID NO: 9) | HVLP324S (SEQ ID NO: 10) |
| HVLP325 (SEQ ID NO: 11) | HVLP325S (SEQ ID NO: 12) |
| HVLP335 (SEQ ID NO: 13) | HVLP335S (SEQ ID NO: 14) |
| HVLP342 (SEQ ID NO: 15) | HVLP342S (SEQ ID NO: 16) |
| HVLP351 (SEQ ID NO: 17) | HVLP351S (SEQ ID NO: 18) |
| HVLP364 (SEQ ID NO: 19) | HVLP364S (SEQ ID NO: 20) |
| HVLP389 (SEQ ID NO: 21) | HVLP389S (SEQ ID NO: 22) |
| HVLP3103 (SEQ ID NO: 23) | HVLP3103S (SEQ ID NO: 24) |

*Referred to herein as "wild-type". If no SEQ ID NO is provided, then the wild type sequence is provided in PCT publication WO2006/099747, especially as shown in FIG. 2 of the publication.

Wild-type $V_H$s, HVHAm302, HVHAm427, HVHAm431, and HVHPC235, were prepared as described in Arbabi-Ghahroudi et al. (2009b). 14 additional wild type $V_H$s, HVHP44, HVHB82, HVHP421, HVHP419, HVHP430, HVHP429, HVHM41, HVHM81, HVHP428, HVHP420, HVHP414, HVHP423, HVHP413, and HVHP426 and wild type $V_L$s were prepared as described in WO 2006/099747 by Tanha. Plasmids containing genes for these wild-type domains (excluding the 14 aforementioned $V_H$s; see below) were used as templates to construct corresponding mutant versions by SOE-PCR.

Inventive constructs, also referred to herein as "Cys mutants," of $V_H$s and $V_L$s (HVHAm302, HVHAm427, HVHAm431, and HVHPC235) were created with splicing by overlap extension (SOE)-PCR (Ho et al., 1989; Kim et al., Submitted Arbabi-Ghahroudi et al, 2010) to introduce a pair of Cys at the positions of 49 and 69 ($V_H$s) or positions 48 and 64 ($V_L$s) as defined by Kabat numbering (Kabat et al., 1991) and as provided in FIG. 1A for a $V_H$ domain and FIG. 1B for a $V_L$ domain. Briefly, to generate $V_H$ mutants. Cys-mutated sub-fragments of the clones were prepared, then assembled to form full-length Cys mutants by SOE-PCR. For example, in the case of HVHAm302S, sub-fragments 302S-1 and 302S-2 were generated separately by standard PCR using the plasmid containing the wild-type HVHAm302 gene as the DNA template and the following pairs of primers:

M13RPa (SEQ ID NO: 37)
(5'-TCACACAGGAAACAGCTATGAC-3')

KT131

(SEQ ID NO: 38)
(5'-ACCACTACTACTAATAG CGCAGACCCACTCCAGCCCCTTC-3')

(for 302S-1 sub-fragment)
and

M13FP (SEQ ID NO: 39)
(5'-CGCCAGGGTTTTCCCAGTC ACGAC-3')

KT129

(SEQ ID NO: 40)
(5'-GCAGACTCCGTGAAGGGCCGATTCACCTGCTCCAGAGACAAT

TCCAAGAAC-3')

(for 302S-2 sub-fragment),

Secondly, using 302S-2 as a template, fragment 302S-2-2 is made by PCR using the following pair of PCR primers: M13FP and

KT130

(SEQ ID NO: 41)
(5'-TGCGCTATTAGTAGTAGTGGTGGTAGCACATACTACGCAGACTCC

GTGAAGGGCCG-3').

This step added the overlapping region to 302S-2. Subsequently, sub-fragments 302S-1 and 302S-2-2 were assembled to create full-length $V_H$ fragment with Cys mutations by SOE-PCR using primer pair M13RP a or b/M13FP. Other $V_H$ mutants were generated from their corresponding wild-type $V_H$ plasmid using the same procedures and primers; $V_L$ mutants were generated using the same SOE-PCR procedure as that for the $V_H$ mutants, except different, $V_L$ gene-specific PCR primers and corresponding wild-type $V_L$ plasmid templates were used. The Cys mutant versions of the 14 non-aggregating $V_H$s, HVHP44, HVHB82, HVHP421, HVHP419, HVHP430, HVHP429, HVHM41, HVHM81, HVHP428, HVHP420, HVHP414, HVHP423, HVHP413, and HVHP426 were synthesized by DNA2.0 (Menlo Park, Calif., USA). They are referred to as HVHP44S, HVHB82S, HVHP421S, HVHP419S, HVHP430S, HVHP429S, HVHM41S, HVHM81S, HVHP428S, HVHP420S, HVHP414S, HVHP423S, HVHP413S, and HVHP426S, respectively. For these 14 constructs, the framework and CDR regions are otherwise the same as those of the corresponding wild-type sequences, which are as provided in PCT publication WO2006/099747, especially as shown in FIG. 2 of the publication.

The full-length Cys mutants were then cloned into an expression vector, expressed, purified, and their concentrations determined as described elsewhere (Sambrook et al., 1989; To, et al., 2005; Arbabi-Ghahroudi et al 2009a; 2009b; 2010).

The additional disulfide linkage had no adverse effect on the expression yield of Cys mutant $V_H$s and $V_L$s; wild-type and mutant sdAbs had comparable yield in milligram quantities. In fact, in some expression trials, HVHAm302S and HVHAm431S had significantly higher expression yields than their wild-type counterparts (see IMAC elution profiles in FIG. 2A).

Figure 2B:
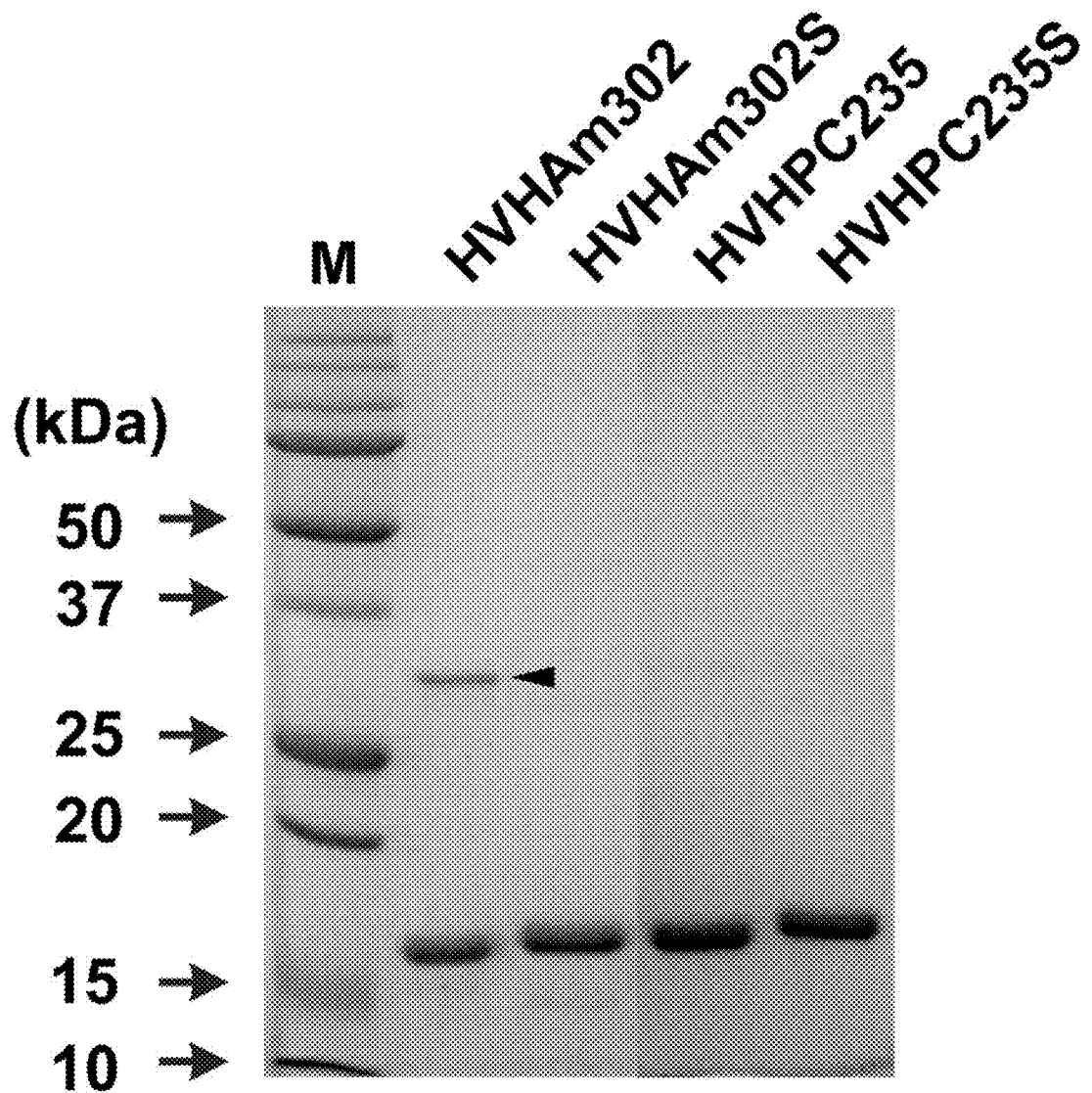
FIG. 2B shows non-reducing SDS-PAGE with wild-type and mutant $V_H$s purified by IMAC (HVHAm302/HVHAm302S and HVHPC235/HVHPC235S pairs are shown as examples). Arrows mark dimeric species of HVHAm302. "M" on the SDS-PAGE gel indicates the lane loaded with protein standards.

On non-reducing SDS-PAGE gels, the mutant $V_H$s and $V_L$s migrated more slowly than their wild-type counterparts (FIG. 2B, examples shown for HVHAm302/HVHAm302S and HVHPC235/HVHPC235S $V_H$ pairs). Migration differences disappeared under reducing conditions. Such SDS-PAGE mobility pattern has been seen in the case of $V_H$Hs as well and was suggested as a hint of Cys49/Cys69 disulfide linkages having been formed in Cys mutants (Hussack et al., 2011). Since the wild-type/mutant pairs have essentially the same molecular weights, the gel migration differences between wild-type and mutant $V_H$s is due to their conformational differences as a consequence of extra, engineered disulfide linkages in mutants (Kim and Tanha, 2010). Moreover, the wild-type $V_H$ HVHAm302 form aggregates (see dimeric bands in FIG. 2B), which was further confirmed by a Western blotting using anti-His antibody (FIG. 2B and data not shown). The dimeric bands disappear for the corresponding mutant $V_H$, HVHAm302S (FIG. 2B). This shows that the engineered disulfide linkage improves $V_H$ non-aggregation and is consistent with the size exclusion chromatography findings (see below and FIG. 4A).

Example 2: Disulfide Linkage Mapping of Cys Mutants

Because the disulfide linkage introduced into the $V_H$ and $V_L$ Cys mutants is not natural to the antibody, the presence of disulfide linkage at the mutated position was verified prior to further characterization of the $V_H$ and $V_L$ mutants.

Based on the knowledge of the two Cys residues (Cys22 and Cys92) forming a native disulfide linkage in the wild-type $V_H$s (Amzel and Poljak, 1979; Williams & Barclay, 1988) and the mutated residues of the mutants, the location of disulfide linkages could be predicted. Since there were some trypsin cleavage sites present between the predicted disulfide bonds in the $V_H$s, it was possible to trypsinize the Cys mutants and utilize mass spectrometry to verify the presence of the engineered disulfide linkage.

Figure 3A:
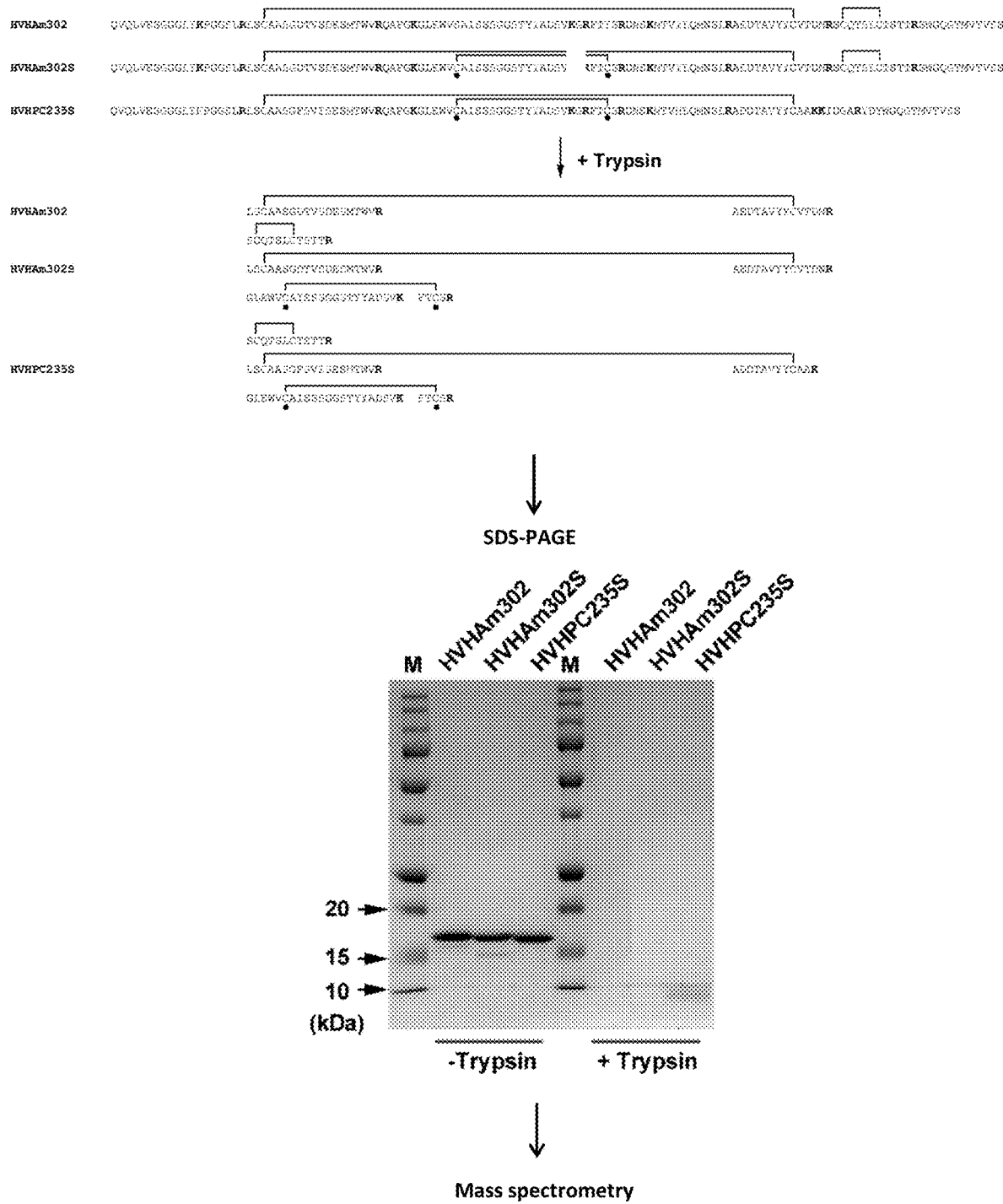
FIG. 3A is a schematic drawing of tryptic peptides (SEQ ID NOS: 25-36, see also Table 2) of $V_H$s for mass spectrometry analysis. Disulfide linkages connecting a pair of Cys are shown by lines. Closed dots mark the cysteines (C) introduced at positions 49 and 69. Only major peptides carrying canonical native (present in wild-type and mutants) or non-canonical engineered (present only in mutants) disulfide linkages are shown. Trypsin digestion sites (C-terminus of Lys and Arg) are bolded. The reducing SDS-PAGE profile shows that $V_H$s have been successfully digested by trypsin into small peptides (compare "+Trypsin" to "−Trypsin"). "M" on the SDS-PAGE gel indicates the lane loaded with protein standards. Sequences at top: HVHAm302 is SEQ ID NO: 1; HVHAm302S is SEQ ID NO: 2; HVHPC235S is SEQ ID NO: 8. Peptides of HVHAm302 are SCQTSLCTSTTR (SEQ ID NO: 25); LSCAASGDTVSDESMTWVR (SEQ ID NO: 26); and AEDTAVYYCVTDNR (SEQ ID NO: 27). Peptides of HVHAm302S are SCQTSLCTSTTR (SEQ ID NO: 28); GLEWVCAISSSGGSTYYADSVK (SEQ ID NO: 29); FTCSR (SEQ ID NO: 30); LSCAASGDTVSDESMTWVR (SEQ ID NO: 31); and AEDTAVYYCVTDNR (SEQ ID NO: 32). Peptides of HVHPC235S are GLEWVCAISSSGGSTYYADSVK (SEQ ID NO: 33); FTCSR (SEQ ID NO: 34); LSCAASGFSVISESMTWVR (SEQ ID NO: 35); and ADDTAVYYCAAK (SEQ ID NO: 36).

Disulfide linkage determination for $V_H$s and $V_L$s was carried out as described elsewhere (Hussack et al., In press (b); Kim and Tanha, In press; Wu et al., 2009). Disulfide linkage determination for HVHAm302 and HVHAm302S were carried out exactly as described in Kim and Tanha (In press). Briefly, $V_H$ Cys mutants were concentrated in 0.1 M Tris-HCl, pH 8.5, using Ultrafree-0.5 centrifugal filter device with biomax-5 membrane (MWCO 5000; Millipore, Nepean, ON, Canada) and subjected to trypsin digestion (Roche Diagnostics Canada, Laval, QC, Canada) at concentration of 0.5 mg/mL in 0.1 M Tris-HCl, pH 8.5, and analyzed by SDS-PAGE for the success of trypsin digestion and subsequently subjected to a peptide mass spectrometry analysis (FIG. 3A and Table 2).

Figure 3B:
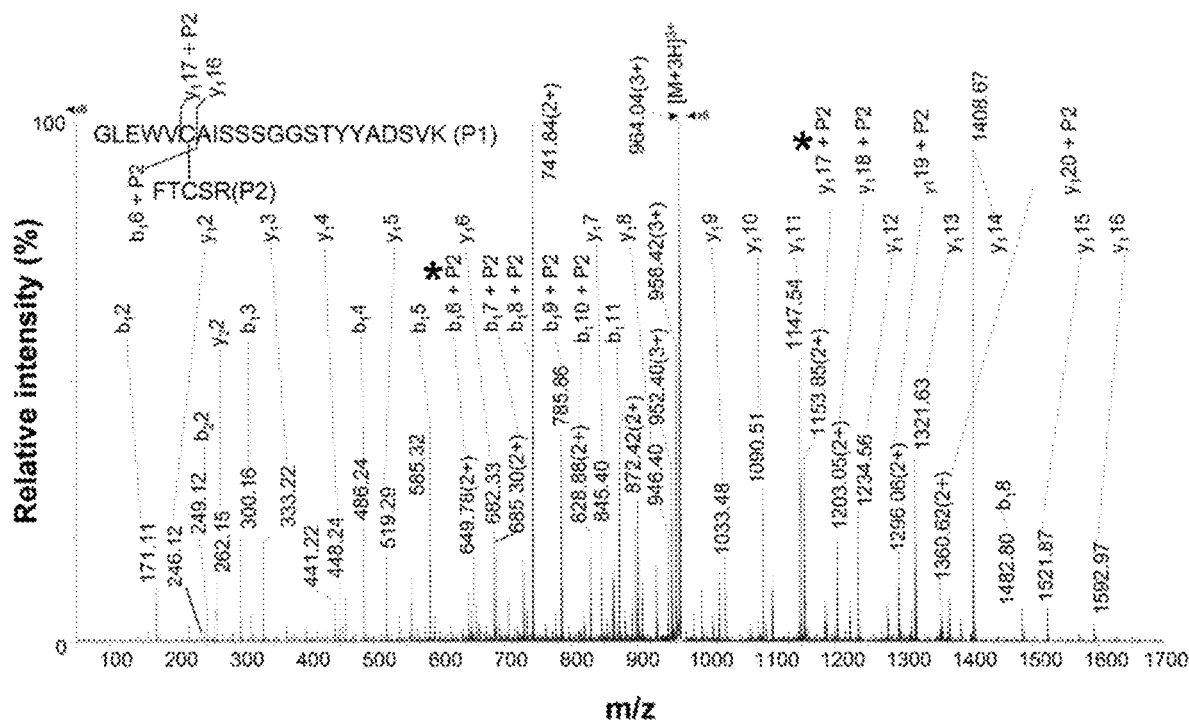
FIG. 3B is a collision induced dissociation (CID)-MS$^2$ spectrum of the m/z 964.04 (3+) ion of the engineered disulfide-linked peptide, GLEWVCAISSSGGSTYYADSVK (P1) (T44-T64)-FTCSR (P2) (T67-T71) (Cys49-Cys69) (SEQ ID NOs: 29 and 30) from the tryptic digest of HVHAm302S. The two peptides (b$_1$6+P2 and y$_1$17+P2) carrying the disulfide linkage were annotated onto the MS (mass spectrometry) peaks and marked with asterisks. Related data are presented in Table 2.

Results showed that the disulfide-linked peptides produced by tryptic digestion of $V_H$s could be identified by the mass spectrometry method employed (FIG. 3B and Table 2). All molecular weights of the recombinant proteins were determined to be within 40 ppm mass accuracy using infusion ESI-MS. The identification coverage of the each protein from the analysis of their tryptic digests using nanoRPLC-MS$^2$ with DDA (data dependent analysis) was more than 30%. The disulfide-linked peptide ions appeared prominent in the survey scan of the DDA experiment. The expected disulfide-linked peptide sequences from the $V_H$s were all confirmed by manual de novo sequencing.

TABLE 2

Disulfide linkage determination of $V_H$s by mass spectrometry. Major tryptic peptides containing disulfide linkages are shown, with connected cysteines depicted in bold and underlined; the remaining sequences in the VH are lost by trypsinization. Spaces within peptide doublets denote sequence discontinuity.

| $V_H$S | Tryptic peptides | $MW_{for}$ | $MW_{exp}$ | ΔMW | SEQ ID NO |
|---|---|---|---|---|---|
| HVHAm302 | SCQTSLCTSTTR | 1284.56 | 1284.57 | −0.01 | 25 |
| | LSCAASGDTVSDESMTWVR | 3630.55 | 3630.52 | 0.02 | 26 |
| | AEDTAVYYCVTDNR | | | | 27 |
| HVHAm302S | SCQTSLCTSTTR | 1284.56 | 1284.57 | −0.01 | 28 |
| | GLEWVCAISSSGGSTYYADSVK FTCSR | $2889.28^a$ | $2889.30^a$ | $-0.02^a$ | 29 |
| | | | | | 30 |
| | LSCAASGDTVSDESMTWVR | 3630.54 | 3630.52 | 0.02 | 31 |
| | AEDTAVYYCVTDNR | | | | 32 |
| HVH PC235S | GLEWVCAISSSGGSTYYADSVK FTCSR | $2889.30^a$ | $2889.23^a$ | $0.07^a$ | 33 |
| | | | | | 34 |
| | LSCAASGFSVISESMTWVR | 3331.52 | 3331.43 | 0.09 | 35 |
| | AEDTAVYYCAAK | | | | 36 |
| HVH P426S | QAPGQGVEWVCVTNNGGSTSADSVK | $3277.47^a$ | $3277.32^a$ | $0.04^a$ | 84 |
| | FTCSR | | | | 85 |

$^a$The very close match between $MW_{for}$ and $MW_{exp}$ indicates the presence of the Cys49—Cys69 disulfide linkage. $MW_{for}$: formula (expected) molecular weight; $MW_{exp}$: molecular weight determined experimentally by MS; ΔMW is calculated: ($MW_{for}$—$MW_{exp}$). $MW_{for}$, $MW_{exp}$, and ΔMW are given in Daltons (Da).

In case of HVHAm302S, a prominent ion at m/z 964.04 (3+) was sequenced as a disulfide-linked peptide GLEWV CAISSSGGSTYYADSVK (P1) (SEQ ID NO:29) and FT CSR (P2) (SEQ ID NO:30) (FIG. 3B and Table 2), where the peptide fragment ions containing disulfide linkage, $y_1$17+P2 and $b_1$6+P2, were clearly observed at m/z 1153.85 (2+) and at m/z 649.78 (2+), respectively (FIG. 3B and Table 2). This confirmed the presence of the engineered disulfide linkage between Cys49 and Cys69 in HVHAm302S. The presence of the engineered disulfide linkage between Cys49 and Cys69 in HVHPC235S was also determined (Table 2). However, the disulfide linkages of HVHAm427S and HVHAm431S could not be confirmed by mass spectrometry, as they were highly resistant to protease (trypsin or pepsin) digestion. However, the drastic $T_m$ increase (Table 4) as well as SDS-PAGE mobility shift (FIG. 2B) of HVHAm427S and HVHAm431S compared to their respective wild-type forms indicates the presence of the engineered disulfide linkage in both HVHAm427S and HVHAm431S.

As another representative, one of the 14 mutant $V_H$s (HVHP426S) was also chosen for the determination of the Cys 49/Cys 69 disulfide linkage formation. As in the case of other $V_H$s, the MS results showed that HVHP426S had formed a disulfide linkage between Cys 49 and Cys 69 (Table 2).

A similar mass spectrometry analysis on the mutant $V_L$s confirmed the presence of the engineered disulfide linkage between positions Cys48 and Cys64 in all $V_L$s (Table 3).

TABLE 3

Disulfide linkage determination of $V_L$s by mass spectrometry (MS). Major tryptic peptides containing disulfide linkages are shown, with connected cysteines depicted by like underlining (and italics) and bolded; In case of HVLP324S, HVLP342S, HVLP351S, and HVLP3103S, another pair of connected cysteines is italicized; the remaining sequences in the $V_L$ are lost by trypsinization. Spaces between peptide fragments denote sequence discontinuity.

| $V_L$S | Tryptic peptides | $MW_{for}$ | $MW_{exp}$ | $MW^a$ | SEQ ID NO |
|---|---|---|---|---|---|
| HVLP324S | VTITCR          LLCFASTLQSGVPSR FSCSGSGTDFTLTISNQPEDFATYYCQQSYSTPR | 6249.91 | 6249.96 | −0.05 | 42, 43, 44 |
| HVLP325S | ATLSCR GSGTLFTLTISSLEPEDSAVYFCQQR | 3495.66 | 3495.40 | 0.26 | 45, 46 |
| | LLCFDTSNR   FSCR | 1576.71 | 1576.68 | 0.03 | 47, 48 |
| HVLP335S | LLCYGTSNR   FSCSGSGTHFTLTIVR | 2750.29 | 2750.32 | −0.03 | 49, 50 |
| | ATLSCR LEPGDFAVYYCQQYGSSPR | 2826.27 | 2820.20 | 0.07 | 51, 52 |
| HVLP342S | VTITCR          LCYGASSLQGGVPSR FSCSGSGTEFTLTISGLQPEDFATYYCLQHHTYPR | 6136.85 | 6136.80 | 0.05 | 53, 54, 55 |
| HVLP351S | ATLSCR              LLCYDASNR FSCSGSGTDFTLTISSLEPEDFAVYYCQQR | 5049.26 | 5049.00 | 0.26 | 56, 57, 58 |
| HVLP364S | LLCYGASSRTR   FSCSGSGTDFTLTISR | 2644.22 | 2644.32 | −0.10 | 59, 60 |
| | ATFSCR LEPEDFAVYYCQQYDTSPR | 3004.30 | 3004.35 | −0.05 | 61, 62 |

TABLE 3-continued

Disulfide linkage determination of $V_LS$ by mass spectrometry (MS). Major tryptic peptides containing disulfide linkages are shown, with connected cysteines depicted by like underlining (and italics) and bolded; In case of HVLP324S, HVLP342S, HVLP351S, and HVLP3103S, another pair of connected cysteines is italicized; the remaining sequences in the $V_L$ are lost by trypsinization. Spaces between peptide fragments denote sequence discontinuity.

| $V_LS$ | Tryptic peptides | $MW_{for}$ | $MW_{exp}$ | $MW^a$ | SEQ ID NO |
|---|---|---|---|---|---|
| HVLP389S | LLCYGNDK  FSCSK | 1492.67 | 1492.59 | 0.08 | 63, 64 |
|  | VTISCSGSSYNIGENSVSWYQQLPGTAPK | 6221.84 | 6222.12 | −0.28 | 65 |
|  | SGTSATLGITGLQTGDEADYYCGTWDSNLR |  |  |  | 66 |
| HVLP3103S | ATLSCR                LLCYGASTR | 5528.56 | 5528.52 | 0.04 | 67, 68, 69 |
|  | FSCSGSGTDFTLTISSLQVEDVAVYYCQQYYTTPK |  |  |  |  |

$^a$The very close match between $MW_{for}$ and $MW_{exp}$ indicates the presence of the Cys48-Cys64 disulfide linkage. $MW_{for}$: formula (expected) molecular weight; $MW_{exp}$: molecular weight determined experimentally by MS; $\Delta MW$ is calculated: $(MW_{for}-MW_{exp})$. $MW_{for}$, $MW_{exp}$, and $\Delta MW$ are given in Daltons (Da).

Crystal structure analysis has confirmed the presence of the disulfide bridge between the non-canonical Cys-Cys residues in addition to the disulfide bridge between the canonical Cys-Cys residues in all inventive $V_H$ and $V_L$ constructs tested.

Example 3: Analytical Size Exclusion Chromatography

Size exclusion chromatography (or gel filtration chromatography) separates proteins by molecular size and hydrodynamic volume (Porath and Flodin, 1959). Therefore, this method is useful in assessing protein aggregation status in solution. Size exclusion chromatography employing Superdex™ 75 is used to assess the aggregation state of $V_H$ (or $V_L$) domains. Non-aggregating $V_H$s (or $V_L$s) should yield chromatograms with a single, symmetrical peak with elution volumes expected for a monomeric $V_H$s (or $V_L$s). In contrast, the chromatogram profiles of aggregating $V_H$s, in addition to the monomeric peaks, consist of additional peaks, e.g., large aggregates, dimeric aggregates, which elute earlier. Percent monomer can be calculated by area integration of the peaks and used as a quantitative measure of $V_H$ (or $V_L$) aggregation tendency (the higher the % monomer of a $V_H$ (or $V_L$), the lower its aggregation tendency and vice versa the higher the % aggregates of a $V_H$ (or $V_L$) the higher its aggregation tendency).

Figure 4A:
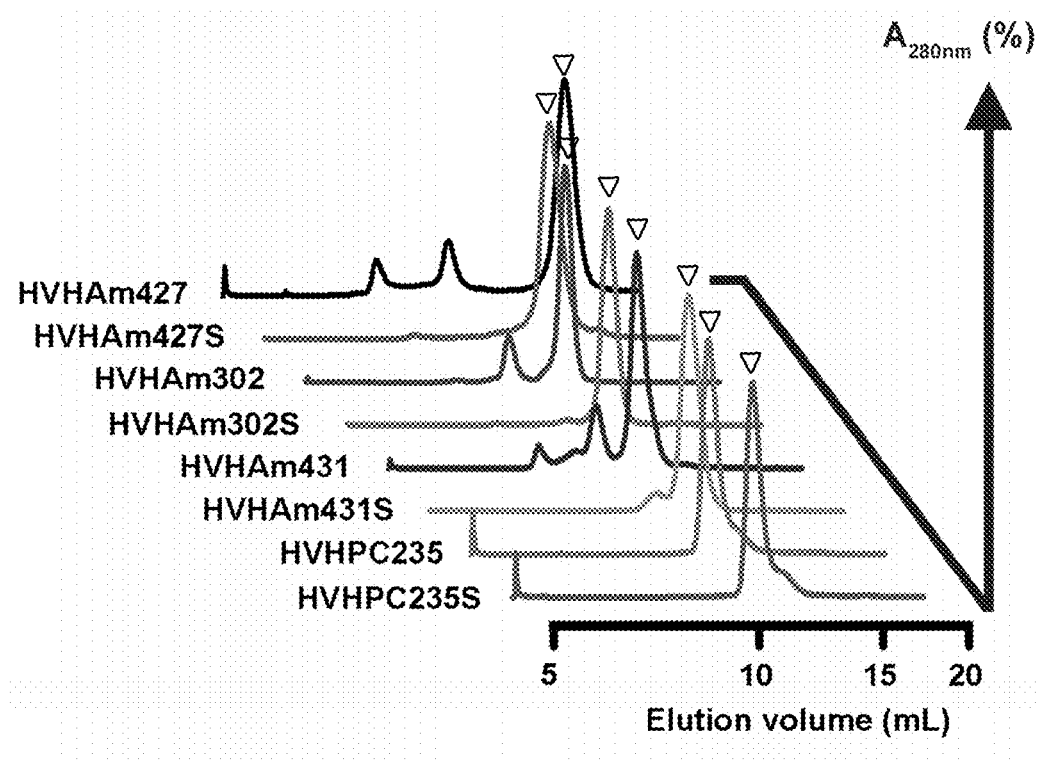
FIG. 4A shows size exclusion chromatograms of $V_H$ domains and their corresponding Cys mutant versions (HVHAm302/HVHAm302S, HVHAm427/HVHAm427S, HVHAm431/HVHAm431S, and HVHPC235/HVHPC235S).
Figure 4B:
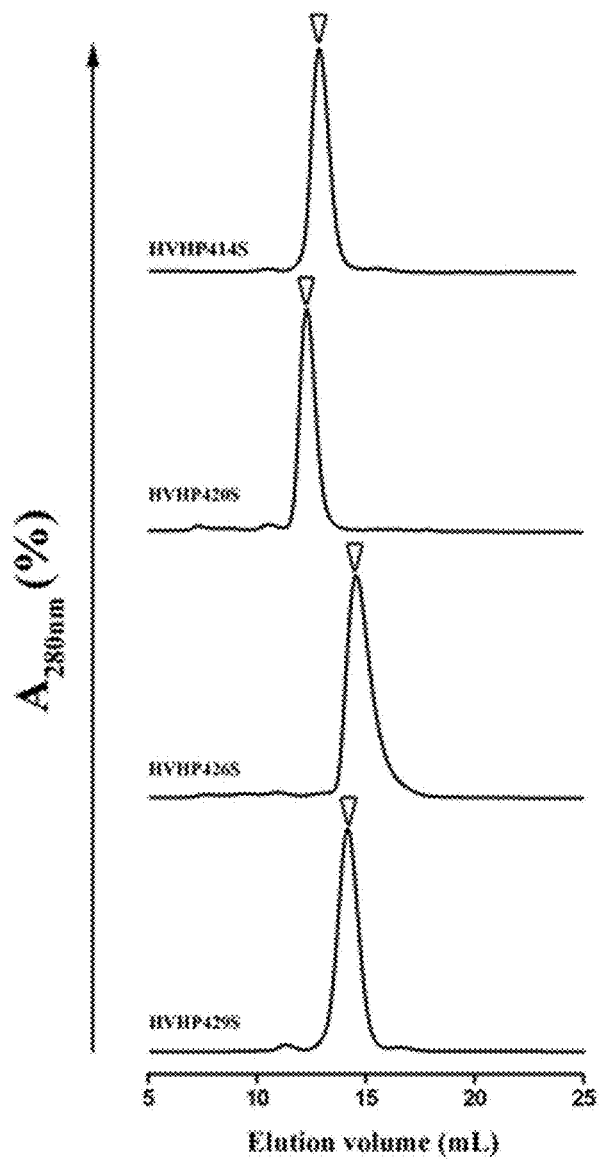
FIG. 4B shows size exclusion chromatograms of 4 additional Cys mutant $V_H$ domains (HVHP414S, HVHP420S, HVHP426S, and HVHP429S). The corresponding wild type versions were previously shown to be non-aggregating monomers (To et al 2005).
Figure 4C:
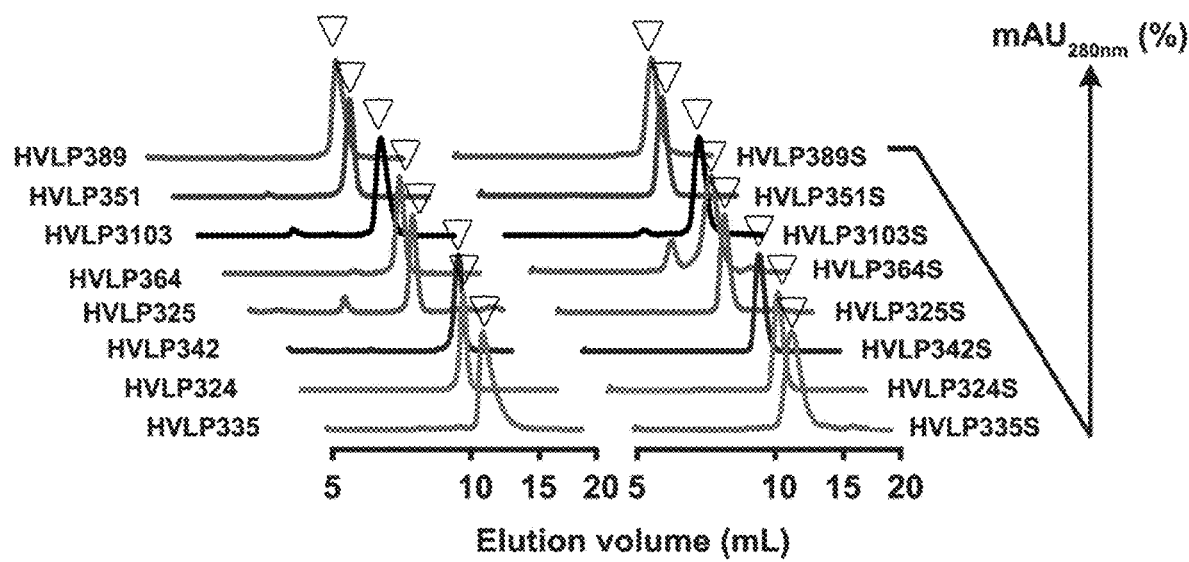
FIG. 4C shows size exclusion chromatograms of human $V_L$ domains and their Cys mutant versions. For each chromatogram in FIGS. 4A, B and C, background absorbance was subtracted and all peaks were normalized with respect to the monomeric peak (shown by arrowheads) which was set at 100%. Peaks to the left of monomeric peaks were considered as aggregate peaks.

Size exclusion chromatography of $V_H$s and $V_L$s, as well as their corresponding Cys mutants, was carried out as previously described (Sambrook et al., 1989; To, et al., 2005; Arbabi-Ghahroudi et al., 2009a; Arbabi-Ghahroudi et al., 2009b; Arbabi-Ghahroudi et al., 2010; Kim and Tanha, In press). Briefly, a Superdex™ 75 size exclusion column was washed with 50 mL of filtered and degassed ddH$_2$O and subsequently equilibrated with 50 mL of filtered and degassed PBS at a pump speed of 0.5 mL/min. Samples were filtered through 0.22 µm disposable filter unit and subsequently submitted to size exclusion chromatography on AKTA FPLC using the Superdex column with PBS buffer at a flow rate of 0.5 mL/min, as per manufacturer's instructions. Eluates corresponding to peaks were collected using an AKTA fraction collector with 0.5 mL of fraction volume per tube. Following size exclusion chromatography, $A_{280}$ versus elution volume was plotted using graphing software GraphPad Prism (version 4.02 for Windows; GraphPad Software, San Diego, Calif.) (FIGS. 4A-4C). Monomeric peak and aggregate peaks were integrated to obtain % monomer or % aggregate.

Absorbance values ($A_{280}$) on size exclusion chromatograms (SEC) were normalized and plotted against elution volumes. Absorbance normalization was performed according to the following formula:

$$\% A_{280} = (A_{280}N - A_{280}B)/(A_{280}M - A_{280}B) \times 100$$

Where % $A_{280}$ is the normalized absorbance, $A_{280}N$ is the absorbance at any elution volume, $A_{280}M$ is the maximum absorbance and $A_{280}B$ is the baseline absorbance.

Results (FIG. 4A) show that protein non-aggregation was greatly improved by the mutation in all three aggregating $V_H$s, HVHAm302, HVHAm427 and HVHAm431. While the wild-type $V_H$s showed early elution peaks typical for aggregating $V_H$s (about 22% for HVHAm302 and HVHAm427, and 25% for HVHAm431) in addition to monomeric peaks, these early elution peaks disappeared in the corresponding mutants, which essentially consisted of monomeric peaks; this indicates that the disulfide linkage engineering converted aggregating $V_H$s to non-aggregating $V_H$s. The non-aggregating $V_H$, HVHPC235, maintained its non-aggregating characteristic when Cys-mutated to HVHPC235S as shown by their size exclusion chromatography (FIG. 4A). FIG. 4B shows representative SEC profiles for the 14 $V_H$ mutants of the $V_H$s, HVHP44S, HVHB82S, HVHP421S, HVHP419S, HVHP430S, HVHP429S, HVHM41S, HVHM81S, HVHP428S, HVHP420S, HVHP414S, HVHP423S, HVHP413S, and HVHP426S. As can be seen in all 4 cases examined (HVHP414S, HVHP420S, HVHP426S, and HVHP429S), the mutants remained non-aggregating similar to their parent wild type $V_H$s. This demonstrates again that in the case of non-aggregating $V_H$s while the disulfide engineering does not compromise the non-aggregation character of $V_H$s, it greatly improves their stability as shown below.

Wild-type $V_L$s were essentially free of aggregates and gave symmetric single peaks. $V_L$ Cys mutants were also monomeric with the exception of HVLP364S, which showed slight aggregation (11% dimeric aggregate). Thus, in general, the engineered disulfide linkage did not compromise the non-aggregating character of $V_L$s (FIG. 4C).

Example 4: Thermostability Measurements by Circular Dichroism (CD) Spectroscopy To assess whether the additional, engineered disulfide linkage in the mutant $V_H$ and $V_L$ would improve protein stability, the thermal stability via measurement of melting temperature ($T_m$) by CD spectroscopy was evaluated.

For all $V_H$s and mutant $V_L$s, a Jasco J-815 spectropolarimeter equipped with a Peltier thermoelectric type temperature control system (Jasco, Easton, Md., USA) was used to carry out experiments. A CD cuvette with a path length of 1 mm was used. The spectra were recorded over a wavelength range of 180-260 nm with scanning speed of 50 nm/min, digital integration time (DIT) of 4 s, a band width of 1 nm, data pitch of 1 nm, and an integration time of 1 s. To measure melting temperature or $T_m$ (Greenfield, 2006a; 2006b), CD spectra were recorded over a temperature range of 30° C. to 96° C. All CD spectra were subtracted from the blank corresponding to buffer spectra. Measurements were performed with concentrations of 50 μg/mL $V_H$s in 100 mM sodium phosphate buffer, pH 7.4. Heat-induced protein denaturation was monitored at 210 nm for all Cys mutant $V_L$s and for HVHAm431, HVHAm431S, and HVHP419S; at 205 nm for HVHAm427, HVHAm427S, HVHAm302, HVHAm302S, HVHB82, HVHP421, HVHP426, HVHP428, HVHP429, HVHP420S, HVHP429S, HVHM81S, HVHP430S, HVHP421S, HVHP426S, HVHP428S, HVHM41, and HVHP414S; at 220 nm for HVHPC235; at 200 nm for HVHPC235S, HVHP430, HVHP413, HVHP423, HVHM81, HVHP419, HVHP420, and HVHB82S; at 202 nm for HVHP44, HVHP414, and HVHP423S; at 208 nm for HVHP44S; and at 209 nm for HVHM41S by changes in ellipticity. The fraction folded (ff) was obtained by a formula as described (Greenfield, 2006a; 2006b):

$$ff = ([\theta]_T - [\theta]_U)/([\theta]_F - [\theta]_U) \quad \text{formula I}$$

where $[\theta]_T$ is the molar ellipticity at any temperature, $[\theta]_F$ is the molar ellipticity of the fully folded protein at 30° C. and $[O]_U$ is the molar ellipticity of the unfolded protein at 90° C. Melting temperature ($T_m$) was obtained as a midpoint of the unfolding curve (fraction folded (ff) versus temperature) by a nonlinear regression curve fit (Boltzman sigmoidal equation) using the graphing software GraphPad Prism (version 4.02 for Windows) and were recorded in Table 4.

For wild-type $V_L$, a Jasco J-810 spectropolarimeter with a NESLAB RTE-111 bath accessory was used. A circular cell with a pathlength of 0.02 cm was used. The spectra were recorded with scanning speed of 100 nm/min, a band width of 1 nm and an integration time of 1 s. The CD spectra were recorded over a temperature range of 25° C. to 85° C. for HVLP342, HVLP351 and HVLP3103, 25° C. to 80° C. for HVLP324, HVLP325, HVLP364 and HVLP389, and 25° C. to 90° C. for HVLP335. Heat-induced changes in molar ellipticity were monitored at 203 nm for HVLP325 and HVLP389 and at 218 nm for HVLP324, HVLP335, HVLP342, HVLP351, HVLP364 and HVLP3103. Measurements were performed in sodium phosphate buffer with concentrations ranging from $4.1 \times 10^{-5}$ M to $5.7 \times 10^{-5}$ M. All CD spectra were subtracted from the blank corresponding buffer spectra and melting temperature ($T_m$) was obtained as previously described for $V_H$s and mutant $V_L$s.

TABLE 4

Affinity constants, $K_D$s, and melting temperatures, $T_m$s, of $V_H$s, $V_L$s, and corresponding Cys mutants. For $V_L$s, the $K_D$s are against protein L, for $V_H$s against protein A.

| $V_L$ | $K_D$(μM) | $T_m$ (° C.) |
|---|---|---|
| HVLP324 | 0.2, 0.07[a] | 59.1 |
| HVLP324S | 0.09[a] | 73.4 |
| HVLP325 | 1 | 64.6 |
| HVLP325S | 1 | 82.5 |

TABLE 4-continued

Affinity constants, $K_D$s, and melting temperatures, $T_m$s, of $V_H$s, $V_L$s, and corresponding Cys mutants. For $V_L$s, the $K_D$s are against protein L, for $V_H$s against protein A.

| $V_L$ | $K_D$(μM) | $T_m$ (° C.) |
|---|---|---|
| HVLP335 | 2 | 57.9 |
| HVLP335S | 2 | 79.0 |
| HVLP342 | 0.6, 0.04[a] | 52.6 |
| HVLP342S | 0.05[a] | 63.8 |
| HVLP351 | 2 | 54.1 |
| HVLP351S | 0.7 | 71.9 |
| HVLP364 | 3 | 52.4 |
| HVLP364S | not determined | 72.3 |
| HVLP3103 | 1 | 55.8 |
| HVLP3103S | 1 | 76.4 |
| HVLP389 | 1 | 49.3 |
| HVLP389S | 0.4, 1[c] | 66.3 |
| HVHAm302[b] | 3.0 | 52.8 |
| HVHAm302S | 10 | 65.4 |
| HVHAm427[b] | 1.6 | 70.9 |
| HVHAm427S | 4 | 84.2[e] |
| HVHAm431[b] | 4 | 69 |
| HVHAm431S | 8 | 84.6[e] |
| HVHPC235 | 0.3 | 55.8 |
| HVHP44 | 1.3[g] | 64.2 |
| HVHP44S | 4.2 | 74.5 |
| HVHB82 | 0.2[g] | 57.9 |
| HVHB82S | 1.2 | 72.9 |
| HVHP421 | 1.0[g] | 57.3 |
| HVHP421S | 2.8 | 69.7 |
| HVHP419 | 1.6[g] | 56.9 |
| HVHP419S | 4.8 (3.2)[d] | 67.4 |
| HVHP430 | 2.3[g] | 71.2/72.5[f] |
| HVHP430S | 7.7 | 82.7 |
| HVHP429 | 1.3[g] | 58.5 |
| HVHP429S | 5.5 (3.4)[d] | 71.8 |
| HVHM41 | 0.5[g] | 60.8 |
| HVHM41S | 1.5 (1.8)[d] | 72.2 |
| HVHM81 | 1.3[g] | 65.8/67.9[f] |
| HVHM81S | 2.1 | 76.8 |
| HVHP428 | 1.8[g] | 62.3 |
| HVHP428S | 1.6 | 73.1 |
| HVHP420 | 1.2[g] | 57.8 |
| HVHP420S | 2.2 | 67.3 |
| HVHP414 | 1.6[g] | 55.3 |
| HVHP414S | 1.8 | 64.7 |
| HVHP423 | 3.0[g] | 55.0 |
| HVHP423S | not determined | 70.7 |
| HVHP413 | 0.3[g] | 54.2 |
| HVHP413S | 1.5 | not determined |
| HVHP426 | 0.8[g] | 62.3/63.1[f] |
| HVHP426S | 3.4 | 79.9 |
| HVH235S | 3 | 72.3 |

[a]The smaller $K_D$ values correspond to the binding of HVLP324, HVLP324S HVLP342, and HVLP342S to the high affinity sites on protein L.
[b]See Table 1 in Arbabi-Ghahroudi et al. (2009b).
[c]2 very close $K_D$s were obtained.
[d]The values in the parentheses were obtained with higher concentration of monomer.
[e]Represents minimum estimated $T_m$ due to not-so-defined lower plateau (see melting curve profiles in FIG. 5A).
[f]Done in duplicates.
[g]$K_D$s taken from To et al., 2005.

Figure 5:
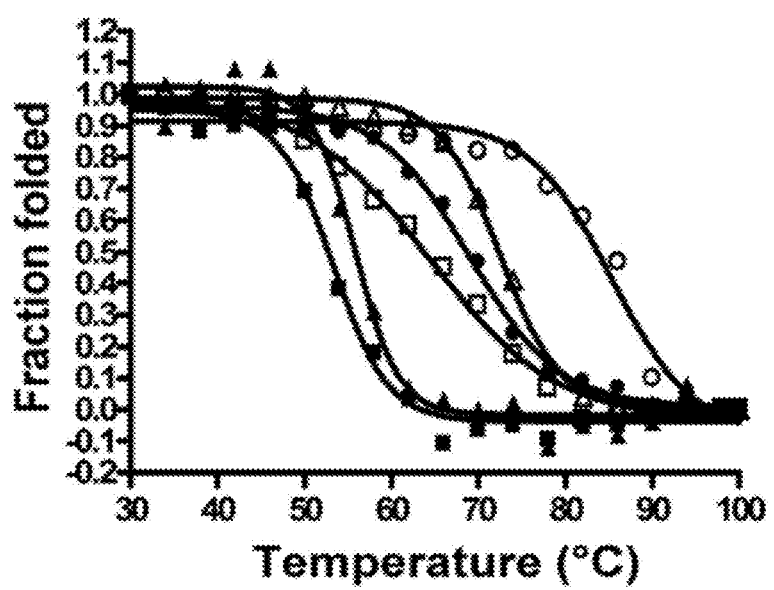
FIG. 5 shows thermal unfolding of $V_H$s. Wild-type and Cys mutant $V_H$s were marked by closed and open symbols, respectively (HVHAm302 and HVHAm302S (square); HVHAm431 and HVHAm431S (circle); HVHPC235 and HVHPC235S (triangle)). The calculated midpoint unfolding temperatures, $T_m$, of $V_H$s are recorded in Table 4.
Figure 6A:
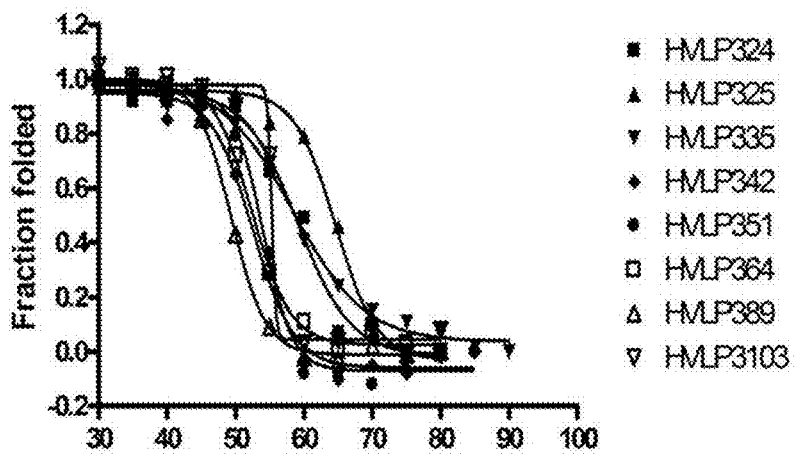
FIGS. 6A-6C show thermal unfolding of wild-type (FIG. 6A) or Cys mutant (FIG. 6B) $V_L$s. Calculated $T_m$s are recorded in Table 4.
Figure 6B:
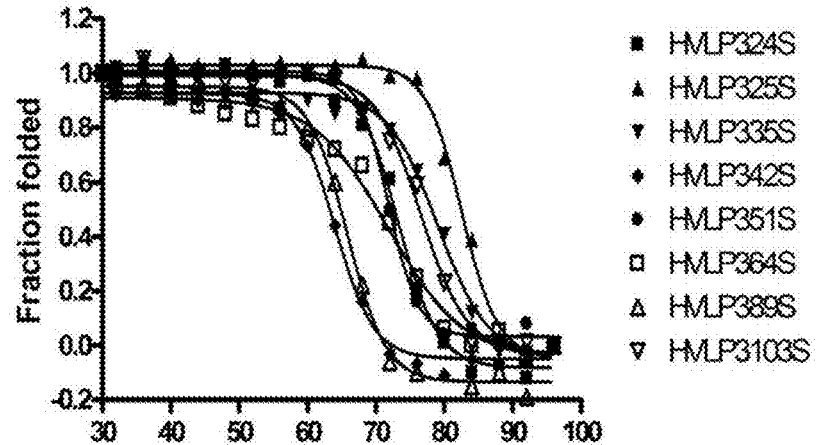

The melting temperatures ($T_m$s) of $V_H$s (HVHAm302 and HVHAm302S, HVHAm427 and HVHAm427S, HVHAm431 and HVHAm431S, HVHPC235 and HVHPC235S, HVHP44 and HVHP44S, HVHB82 and HVHB82S, HVHP421 and HVHP421S, HVHP419 and HVHP419S, HVHP430 and HVHP430S, HVHP429 and HVHP429S, HVHM41 and HVHM41S, HVHM81 and HVHM81S, HVHP428 and HVHP428S, HVHP420 and HVHP420S, HVHP414 and HVHP414S, HVHP423 and HVHP423S, HVHP413 and HVHP413S, and HVHP426 and HVHP426S) and $V_L$s were determined based on ellipticity data assuming a two-state system, which is in agreement with the observed denaturation curves corresponding to a sharp transition into denaturation (FIGS. 5 and 6 and Table 4). The $T_m$ values were taken at midpoint of the sigmoidal denaturation curves of fraction folded (ff) versus temperature. Unlike HVHAm302 and HVHC235, both HVHAm427 and HVHAm431 had considerably higher $T_m$s, likely due to the presence of possible inter-CDR1-CDR3 disulfide linkages (FIG. 1A and Table 4). In the case of HVHAm302 and HVHAm302S, HVHAm427 and HVHAm427S, HVHAm431 and HVHAm431S, HVHPC235 and HVHPC235S $V_H$s, we found that mutant $V_H$s had significantly higher $T_m$s compared to their corresponding wild type counterparts (Table 4) (paired t-test, two-tailed, p=0.0008), signifying the stabilizing effects of the engineered disulfide linkage. The wild type $V_H$s had $T_m$s of 52.8° C.-70.9° C. which were increased to 65.4° C.-84.6° C. for mutant $V_H$s. This corresponds to $T_m$ increases ($\Delta T_m$) of 12.6° C. —16.5° C. Similar patterns were observed in the case of HVHP44 and HVHP44S, HVHB82 and HVHB82S, HVHP421 and HVHP421S, HVHP419 and HVHP419S, HVHP430 and HVHP430S, HVHP429 and HVHP429S, HVHM41 and HVHM41S, HVHM81 and HVHM81S, HVHP428 and HVHP428S, HVHP420 and HVHP420S, HVHP414 and HVHP414S, HVHP423 and HVHP423S, HVHP413 and HVHP413S, and HVHP426 and HVHP426S $V_H$s, where the wild type $V_H$s had $T_m$s of 54.2° C.-72.5° C. while the mutant counterparts had $T_m$s of 64.7° C.-82.7° C. This corresponds to $T_m$ increases ($\Delta T_m$) of 8.9° C.-16.8° C. for mutant $V_H$s (Table 4). By comparing disulfide linkage patterns of mutant versus wild type $V_H$s (Table 2), it is clear that the $T_m$ increases are indeed due to the presence of the extra Cys49/Cys69 disulfide linkages. Without wishing to be bound by theory, the disulfide linkage in HVHAm427S could cause conformational alteration to bring conformational modules, such as beta-sheets, close together (acting through either short or long range contact) to induce extra chemical forces, such as hydrophobic interaction or salt bridges, to further stabilize the structure at that level.

Figure 6C:
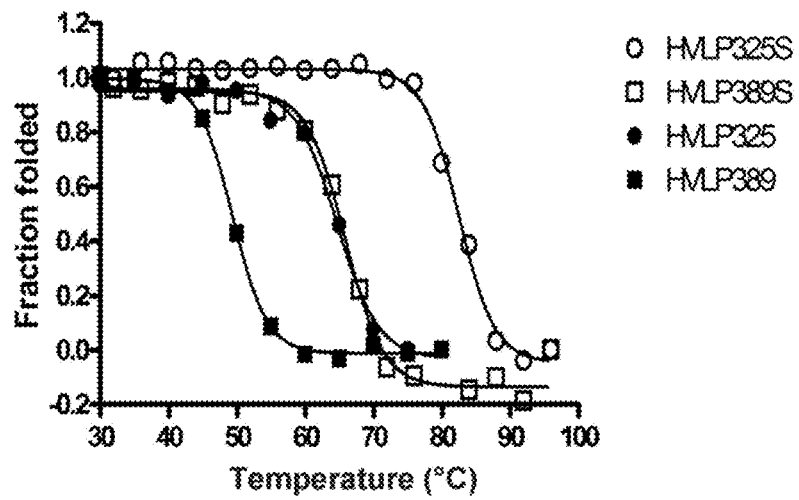

$T_m$s of $V_L$s were in the range of 49.3° C.-64.6° C., a range observed in other sdAbs (Jespers et al., 2004; Tanha et al., 2006) (FIG. 6 and Table 4). As in the case of mutant $V_H$s, for all mutant $V_L$s, the $T_m$s were drastically increased by an average of 17° C. (range: 11.2° C.-21.1° C.) compared to $T_m$s of the wild-type $V_L$s. The $T_m$s of mutant $V_L$s were in the range of 63.8° C.-82.5° C. compared to 49.3° C.-64.6° C. for wild-type $V_L$s. Thus, the $T_m$ of the least thermostable mutant, HVLP342S, was comparable to that of the most thermostable wild-type, HVLP325 (FIG. 6C); HVLP325S had the highest $T_m$ (82.5° C.), while HVLP342S had the lowest one (63.8° C.). The effect of disulfide engineering on the stability of $V_L$s appears to be universal, as it stabilizes both lambda and kappa type $V_L$s and irrespective of their germline sequence origin.

Example 5: Surface Plasmon Resonance (SPR)

The protein A and protein L binding property of $V_H$s and $V_L$s, respectively, was used in SPR binding analyses to probe any subtle possible structural changes due to the engineered disulfide linkages in $V_H$ and $V_L$ mutants. Protein A is often used to monitor conformational integrity of $V_H$s (Starovasnik et al., 1999). Standard procedures were carried out for SPR analysis of $V_H$s and $V_L$s. $V_H$S and $V_L$s were subjected to Superdex™ 75 10/300 (GL) size exclusion chromatography (GE Healthcare) in HBS-EP buffer (10 mM HEPES, pH 7.4, 150 mM NaCl, 3 mM EDTA and 0.005% P20 surfactant) with flow rate of 0.5 mL/min prior to BIACORE analysis and purified monomer peaks collected even in the absence of any evidence of aggregated material.

The binding kinetics for the interaction of the $V_H$S to protein A (Pierce, Nepean, ON, Canada) and $V_L$s to protein L (Pierce) were determined by SPR using BIACORE 3000 biosensor system (GE Healthcare).

For the $V_H$S, HVHAm302, HVHAm302S, HVHAm427, HVHAm427S, HVHAm431 and HVHAm431S, protein A and ovalbumin (as a reference protein) (Sigma, Oakville, ON, Canada) of 540 RUs and 1350 RUs, respectively, were immobilized on research grade CM5 sensor chips (GE Healthcare). Immobilizations were carried out at 50 µg/mL in 10 mM acetate buffer, pH 4.5, using the amine coupling kit supplied by the manufacturer (GE Healthcare). All measurements were carried out at 25° C. in HBS-EP buffer at a flow rate of 50 µL/min. Surfaces were regenerated by washing with the running buffer.

For HVHPC235 and HVHPC235S, approximately 1,100 RUs and 1,000 RUs of recombinant protein A and ovalbumin (reference protein), respectively, were immobilized on research grade sensor chip CM5. Immobilizations were carried out at 50 µg/mL in 10 mM acetate buffer (pH 4.0 or pH 4.5 for protein A or ovalbumin, respectively) using the amine coupling kit supplied by the manufacturer. All measurements were carried out at 25° C. in HBS-EP buffer at a flow rate of 20 µL/min or 40 µL/min for HVHPC235 or HVHPC235S, respectively.

For mutant $V_H$S (HVHP44S, HVHB82S, HVHP421S, HVHP419S, HVHP430S, HVHP429S, HVHM81S, HVHP428S, HVHP420S, HVHM41S, HVHP423S, HVHP413S, HVHP426S, and HVHP414S), approximately 1,170 RUs and 1,240 RUs of recombinant protein A and ovalbumin (reference protein), respectively, were immobilized on research grade sensor chip CM5. Immobilizations were carried out at 50 µg/mL in 10 mM acetate buffer (pH 4.5 for both protein A and ovalbumin) using the amine coupling kit supplied by the manufacturer. All measurements were carried out at 25° C. in HBS-EP buffer at a flow rate of 20 µL/min or 40 µL/min for HVHB82S, HVHP421S, HVHP429S, HVHM41S, HVHM81S, HVHP423S, HVHP413S, HVHP426S, and HVHP414S or HVHP44S, HVHP419S, HVHP430S, HVHP428S, and HVHP420S, respectively. The protein A binding property of the wild-type counterparts were determined previously (To et al 2005).

For wild-type $V_L$s, 600 RUs of protein L or 800 RUs of a Fab reference protein were immobilized on research grade CM5 sensor chips (GE Healthcare). For $V_L$ mutants, approximately 400 RUs of recombinant protein L or ovalbumin (reference protein) were immobilized. Immobilizations were carried out at protein concentrations of 20 or 50 µg/mL in 10 mM acetate buffer, pH 4.5, using the amine coupling kit supplied by the manufacturer (GE Healthcare). All measurements were carried out at 25° C. in HBS-EP buffer at a flow rate of 40 or 50 µL/min. Surfaces were regenerated by washing with the running buffer. All data were evaluated using the BIAevaluation 4.1 software (GE Healthcare).

Figure 7A:
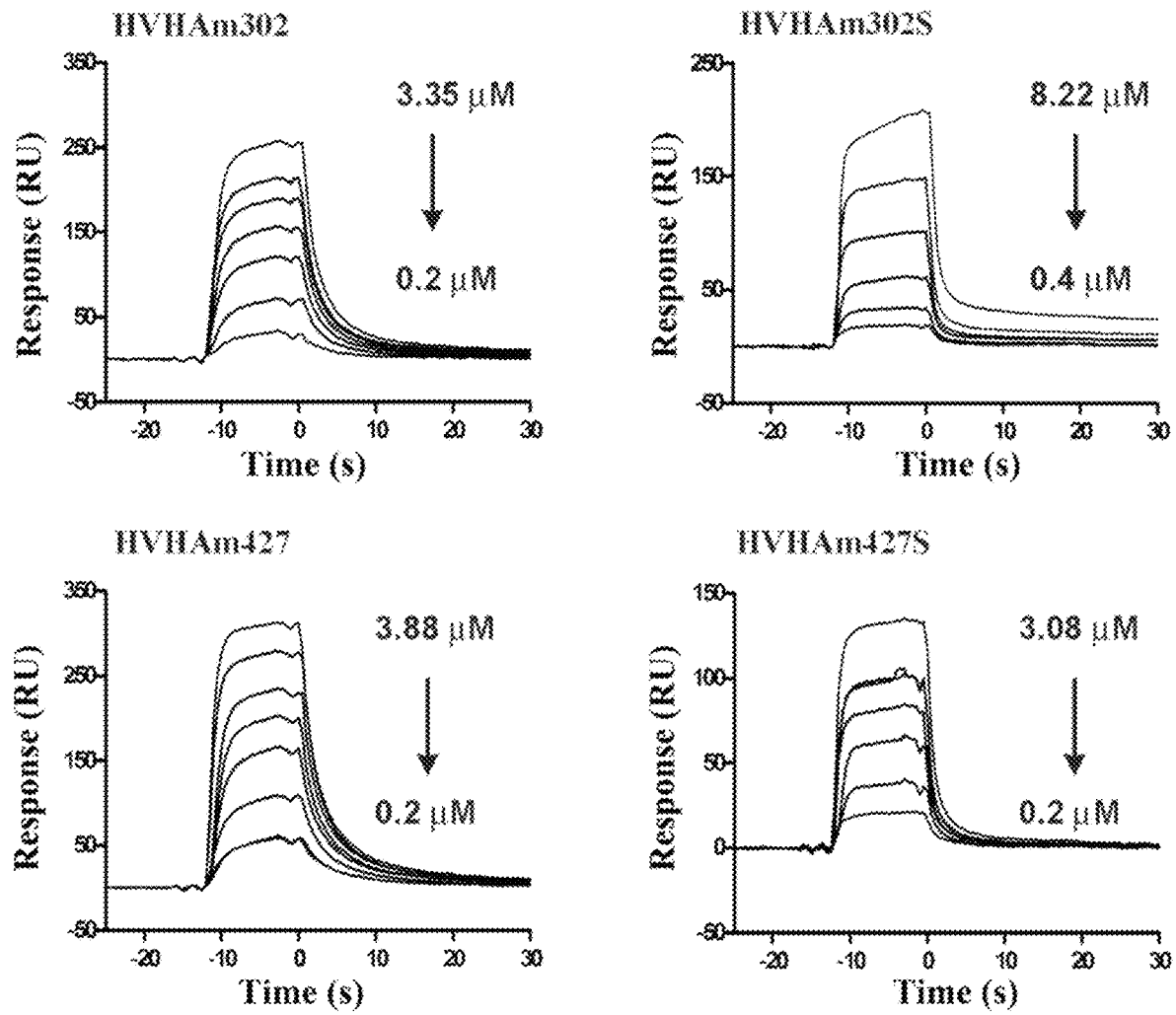
FIGS. 7A and 7B show SPR binding analyses of $V_H$s against immobilized protein A.
Figure 7A:
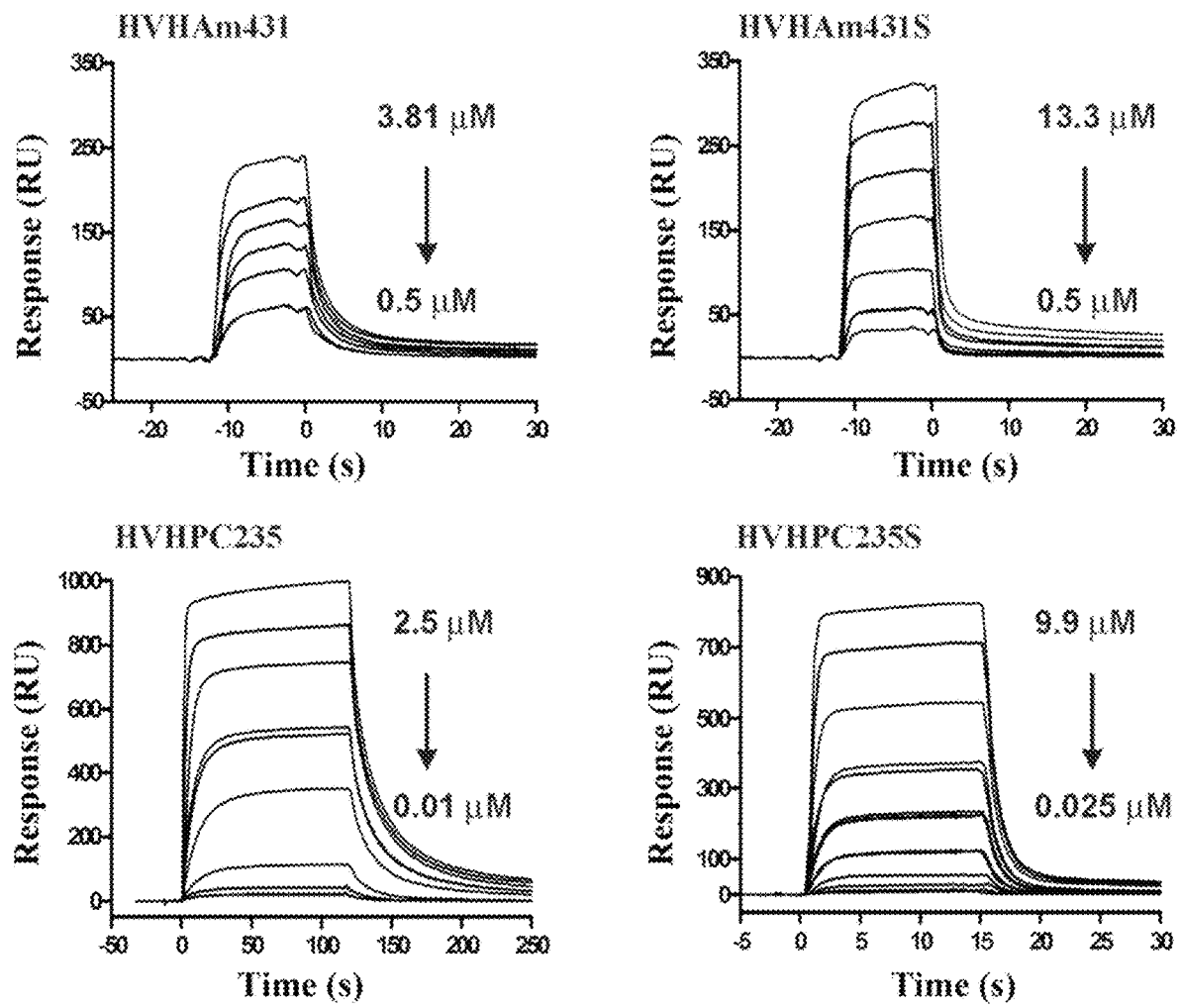
Figure 7B:
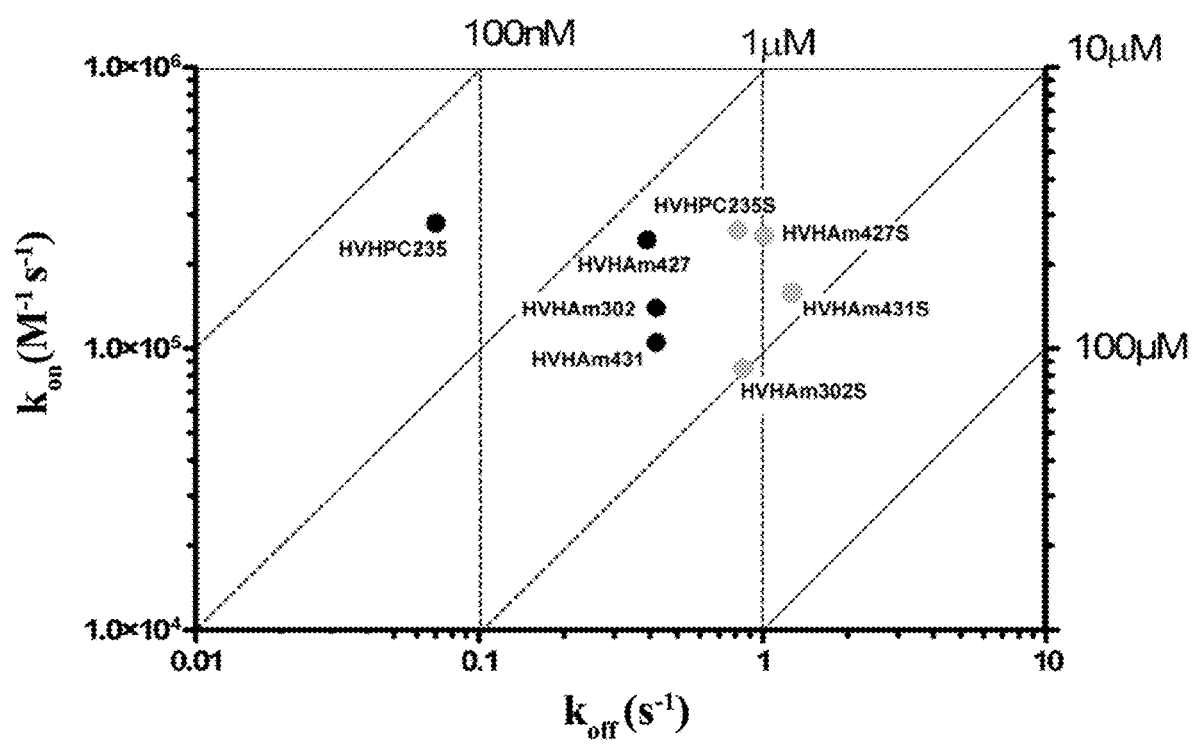

The SPR analysis showed that the vast majority of mutant $V_H$S (HVHAm302S, HVHAm427S, HVHAm431S, HVHPC235S, HVHB82S, HVHP421S, HVHP419S, HVHP430S, HVHP429S, HVHM81S, HVHP420S, HVHM41S, HVHP423S, HVHP413S, HVHP426S, and HVHP44S) bound to protein A with less affinity, reflected by higher $K_D$ values, compared to their wild-type counterparts (FIGS. 7A and 7B and Table 4) (only two mutant $V_H$S [HVHP428S and HVHP414S] showed more or less the same $K_D$ values as their wild-type counterparts). The reduction in protein A binding (increase in $K_D$ values) ranges from 1.6-fold for the HVHM81/HVHM81S pair to 10-fold for the HVHPC235/HVHPC235S pair (FIG. 7A and Table 4). This demonstrates that the engineered disulfide bond somewhat alters the structural conformations of the $V_H$s. Without wishing to be bound by theory, the protein A binding sites, which are known to reside within FR1 and FR3 of $V_H$s (Starovasnik et al., 1999; Riechmann and Davies, 1995), may have been compromised by the introduction of the two Cys on beta-strands of FR2 and FR3. Interestingly, the mutant $V_H$s showed consistently increased disassociation rate constants ($k_{off}$) compared to their wild-type counterparts, which resulted in raising the equilibration binding constant ($K_D$) (FIG. 7B).

Figure 8A:
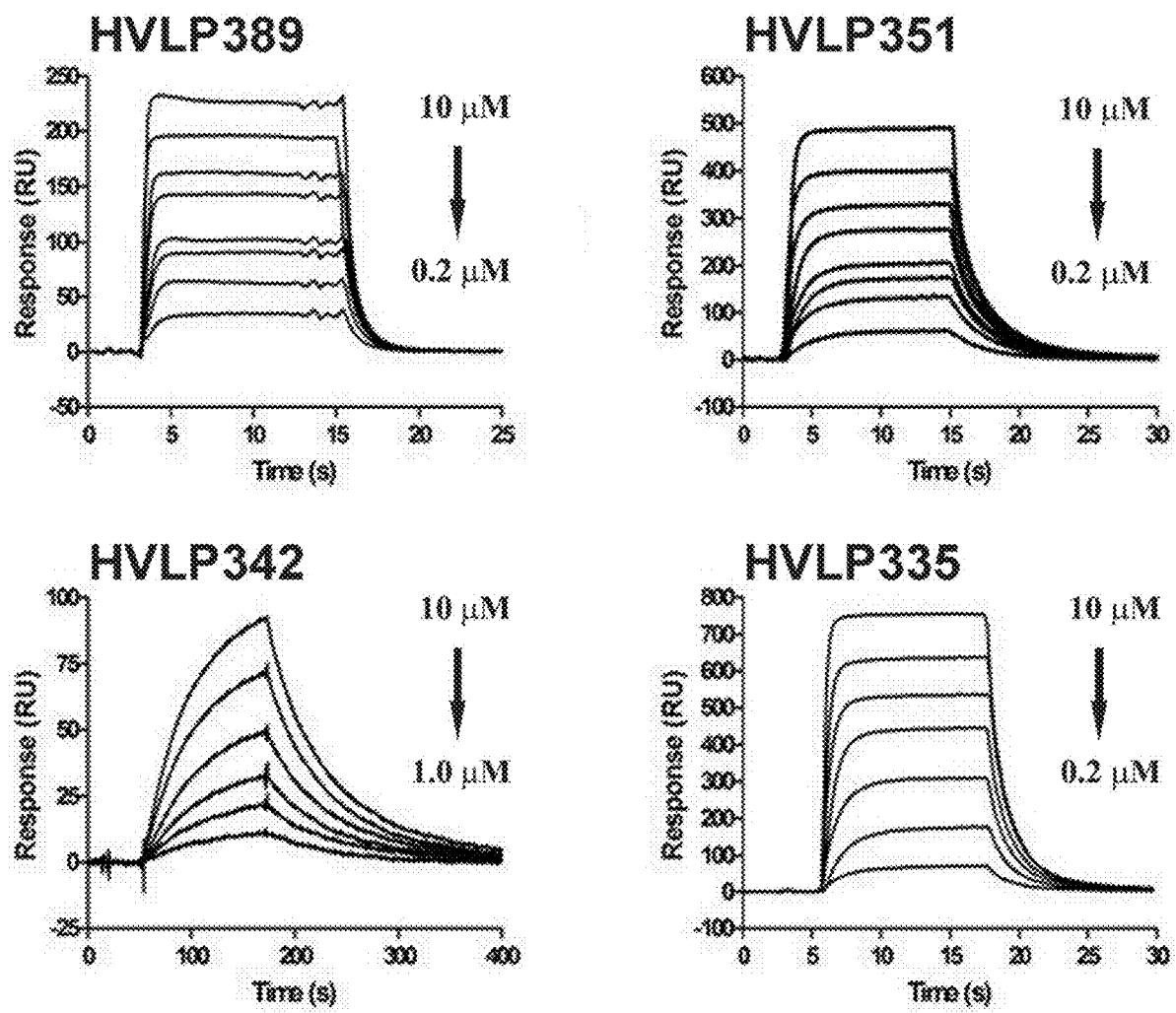
FIGS. 8A and 8B show Biacore sensorgrams of $V_L$s to immobilized protein L.
Figure 8A:
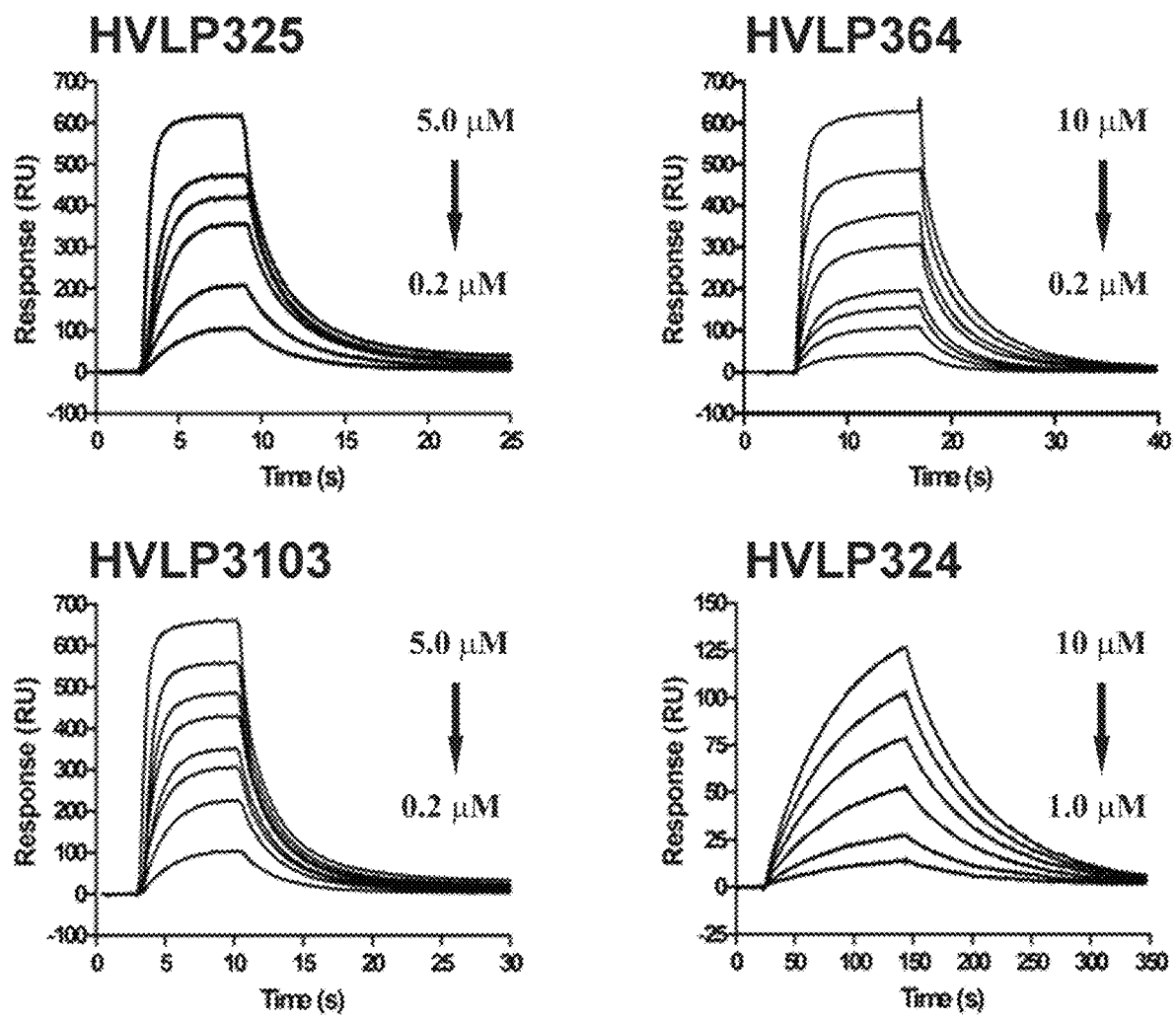
Figure 8B:
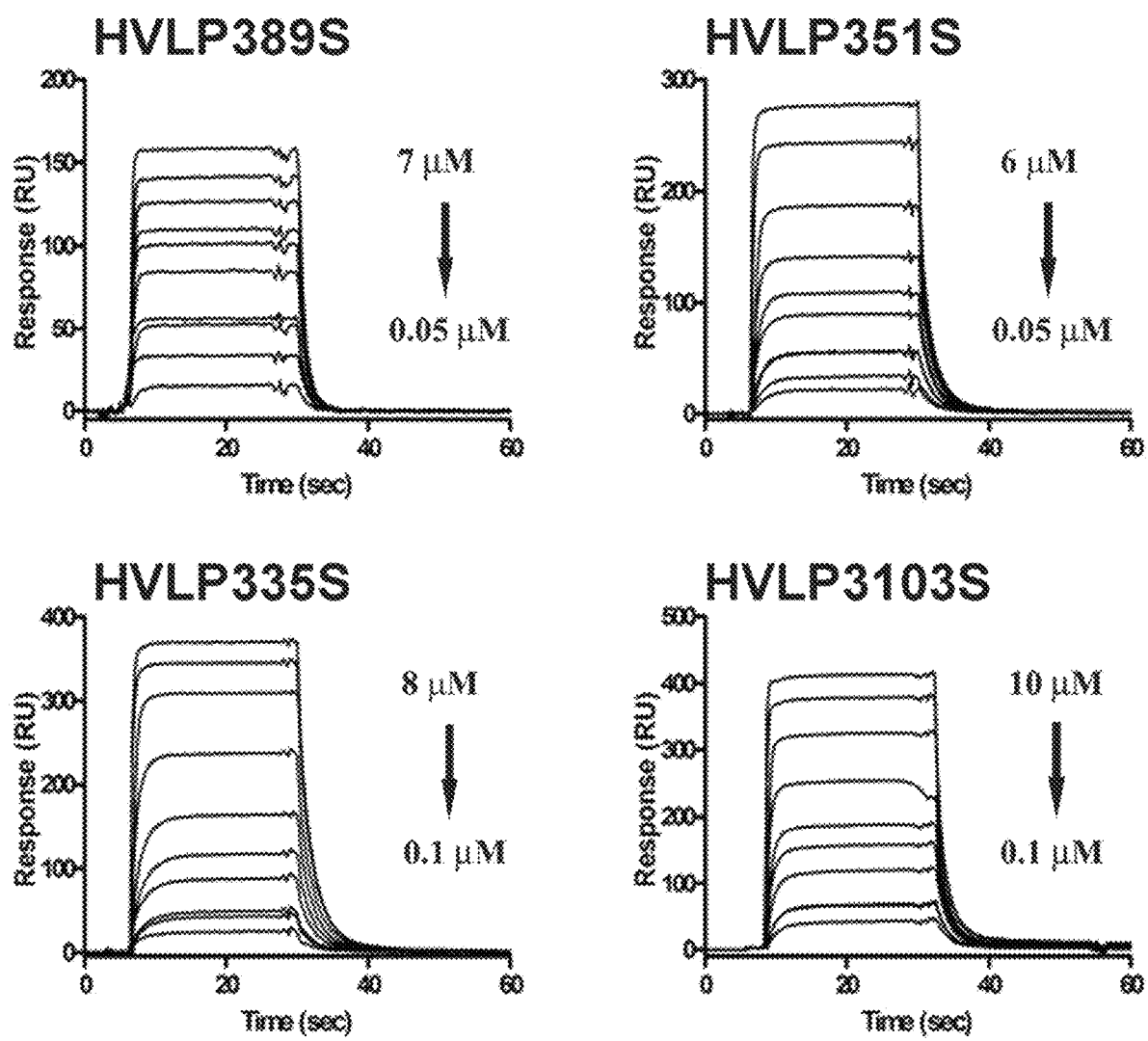
Figure 8B:
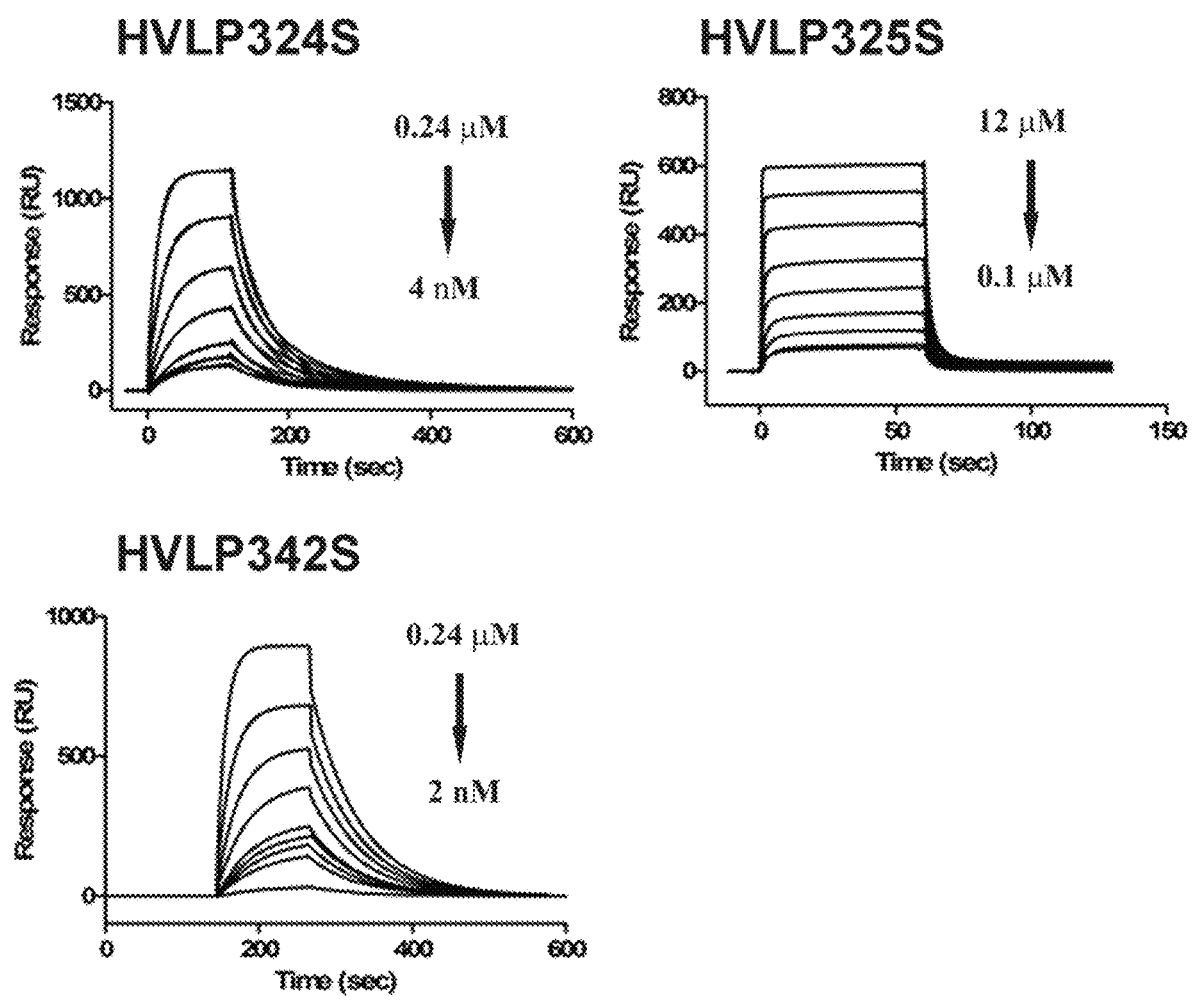

It was found that the $V_L$ Cys mutants bound to protein L with affinities similar to their wild-type counterparts (FIGS. 8A and 8B and Table 4), indicating that the disulfide bond did not affect the overall structure of the $V_L$s.

Example 6: Protease Stability

The effect of the engineered disulfide linkage on the protease stability of $V_L$s and $V_H$s was evaluated using major GI proteases trypsin, chymotrypsin and pepsin. After the digestion reactions with GI proteases, $V_L$s and $V_H$s were examined for the occurrence of enzymatic cleavage by SDS-PAGE and mass spectrometry. Digestions were performed essentially as described (Hussack et al., 2011).

For $V_L$s, digestion experiments were performed in a total volume of 304 with 6 µg of $V_L$ at 37° C. for 1 h with an enzyme to sdAb ratio of 1:200, 1:40, 1:20, and 1:10 (trypsin/chymotrypsin), or 1:200, 1:20, 1:10, and 1:4 (pepsin). Tryptic and chymotryptic digestion experiments were carried out using sequencing grade enzymes (Hoffmann-La Roche Ltd., Mississauga, ON, Canada), according to the manufacturer's instructions. Pepsin (Sigma) digestion reactions were performed at ~pH 2.0 where the pH was adjusted by adding appropriate volume of 400 mM HCl. In control experiments, enzymes were replaced with equal volume of reaction buffer. Reactions were stopped by adding an equal volume of SDS-PAGE sample buffer (containing 0.2 M dithiothreitol) and boiling the mixture at 95° C. for 5 min. Samples were subsequently subjected to analysis by SDS-PAGE and the percent of intact sdAbs after protease digestions were determined by spot density analysis as described in Hussack et al., In press(a) and compared with controls to calculate the percentage of $V_L$s with intact structure after protease digestion.

For $V_H$s, digestion experiments with trypsin/chymotrypsin/pepsin were performed in a total volume of 30 µL with 6 µg of $V_H$ and its mutant $V_H$ counterpart in parallel at 37° C. for 1 h with an enzyme to sdAb ratio of 1:20 and duplicated by two independent trials. The digestions and analyses were carried out as described for the $V_L$s.

Figure 9A:
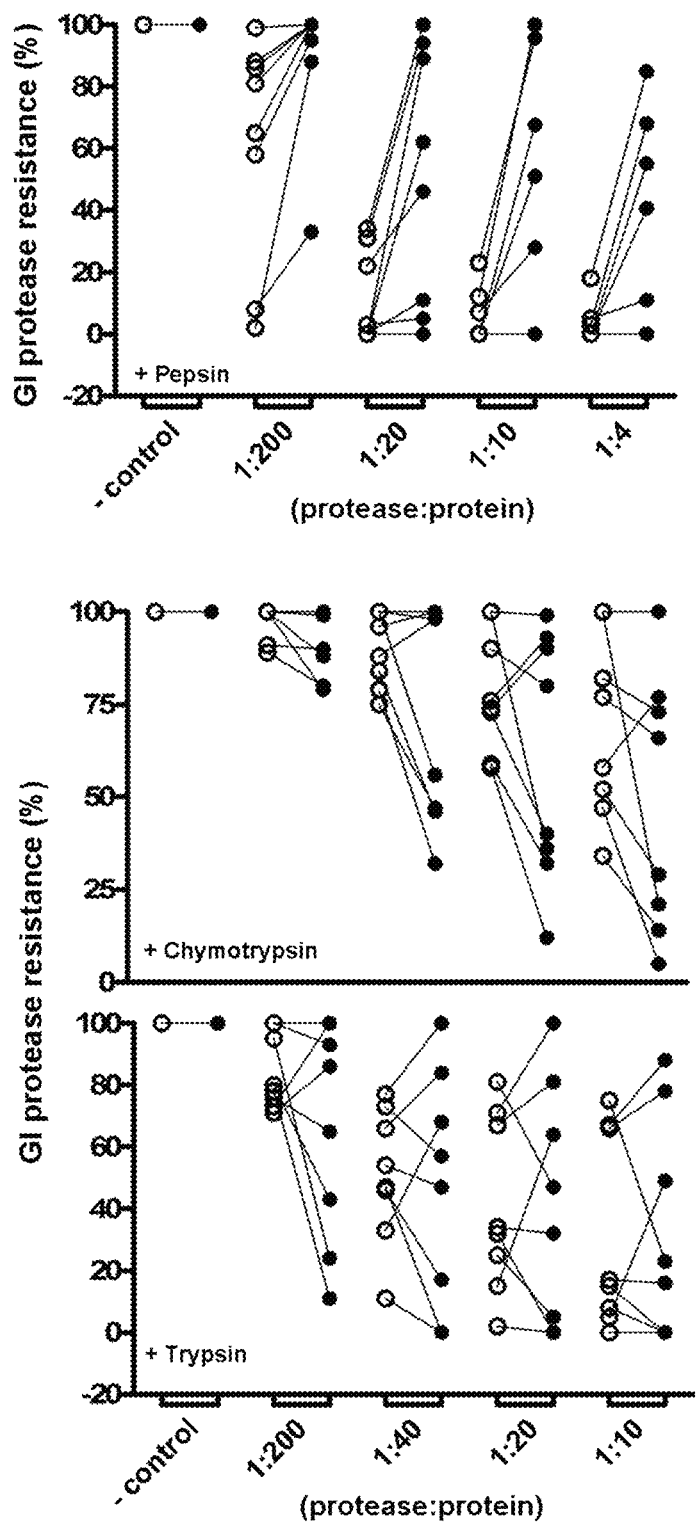
FIGS. 9A and 9B show GI protease (pepsin, chymotrypsin and trypsin) resistance of $V_L$s.

The results are shown in FIG. 9A. No significant difference between wild-type and the mutant $V_L$s was observed in terms of resistance to trypsin or chymotrypsin (Wilcoxon matched pairs t test, two-tailed P values=0.2969 [trypsin] and 0.0625 [chymotrypsin]), but the difference in resistance to pepsin was significant (Wilcoxon matched pairs t test, two-tailed P value=0.0078). The mutant $V_L$s tested showed improved resistance against pepsin, one of which, HVLP3103S, showed a dramatic increase from 0% resistance (wild-type) to almost 90% resistance (mutant). Mean of pepsin resistance was 51% for mutants $V_L$s versus 11% for wild-type $V_L$s at the pepsin to $V_L$ ratio of 1:20. At the same ratio, median of pepsin resistance was 54% for mutant $V_L$s versus 1.5% for wild-type $V_L$s. Thus, the disulfide linkage engineering of sdAbs, increased their pepsin resistance significantly without affecting their trypsin and chymotrypsin resistance properties.

Figure 9B:
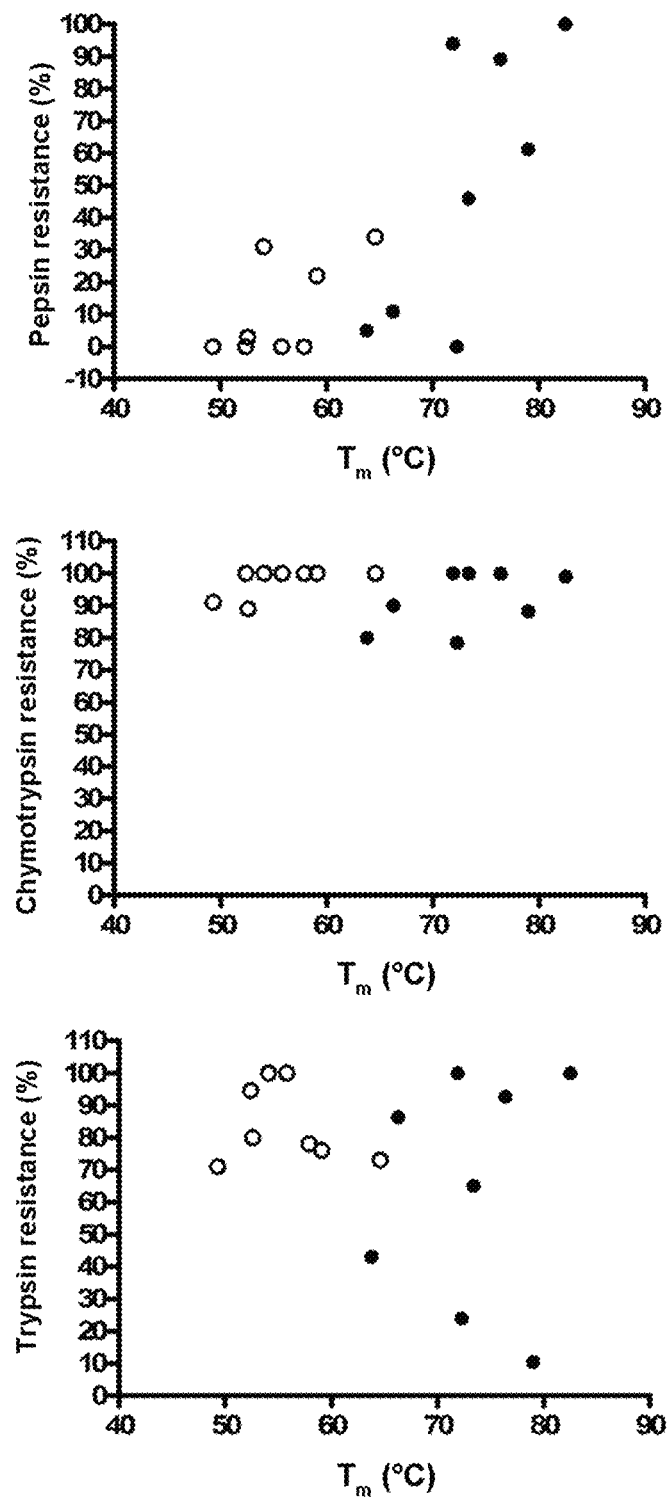

The correlation between the thermal stability and the protease resistance was further explored by plotting protease resistance (%) vs. $T_m$ (FIG. 9B). In general, $V_L$s with higher $T_m$s showed greater resistance to pepsin (two-tailed, P value=0.0012, $R^2$ (Spearman)=0.7344). Such correlation was not observed in the case of trypsin and chymotrypsin (two-tailed, P value=0.5245, $R^2$ (Spearman)=−0.1719 [trypsin]; two-tailed, P value=0.5407, $R^2$ (Spearman)=−0.1653 [chymotrypsin]).

In the case of the $V_H$S that are shown in Table 5, the mutant $V_H$S showed higher resistance (% median) to all the three GI proteases (77% and 82% [trypsin], 69% and 75% [chymotrypsin], and 96% and 98% [pepsin], for the wild-type and the mutant $V_H$S, respectively), although the differences were not that significant (Wilcoxon matched pairs t test, two-tailed P values=0.0899 [trypsin], 0.7896 [chymotrypsin]), and 0.7832 [pepsin]). While most of the mutant $V_H$S showed unchanged or slightly improved resistance against pepsin, two mutant $V_H$S (HVHM81S and HVHP423S) showed decreased resistance from 100% (for both HVHM81 and HVHP423) to 53% (for HVHM81S) and to 68% (for HVHP423S), although the pepsin resistance of HVHM81S seemed to be underestimated due to inability of the spot density analysis tool to recognize the protein bands properly. Intriguingly, large improvements in terms of trypsin resistance were shown from two mutant $V_H$S (HVHP44S and HVHP413S) where their trypsin resistance improved from 5% and 29% (HVHP44 and HVHP413, respectively) to 57% and 100% (HVHP44S and HVHP413S, respectively). Taken together, the mutants are as resistant to proteases as the wild type counterparts.

TABLE 5

GI protease resistance of $V_H$s

| $V_H$ | Trypsin Resistance (%) | Chymotrypsin Resistance (%) | Pepsin Resistance (%) |
|---|---|---|---|
| HVHP44 | 5 ± 2 | 69 ± 1 | 95 ± 9 |
| HVHP44S | 57 ± 2 | 63 ± 7 | 100 ± 10 |
| HVHB82 | 92 ± 5 | 100 ± 19 | 100 ± 16 |
| HVHB82S | 87 ± 7 | 64 ± 17 | 95 ± 28 |
| HVHP421 | 74 ± 7 | 59 ± 7 | 97 ± 25 |
| HVHP421S | 100 ± 10 | 78 ± 31 | 100 ± 22 |
| HVHP419 | 72 ± 7 | 52 ± 2 | 87 ± 11 |
| HVHP419S | 75 ± 3 | 52 ± 1 | 85 ± 6 |
| HVHP430 | 95 ± 8 | 100 ± 19 | 100 ± 3 |
| HVHP430S | 100 ± 19 | 74 ± 24 | 100 ± 3 |
| HVHP429 | 89 ± 6 | 70 ± 7 | 95 ± 28 |
| HVHP429S | 82 ± 12 | 86 ± 2 | 100 ± 5 |
| HVHM41 | 11 ± 3 | 96 ± 32 | 100 ± 16 |
| HVHM41S | 22 ± 18 | 68 ± 13 | 93 ± 16 |
| HVHM81 | 86 ± 4 | 95 ± 8 | 100 ± 4 |
| HVHM81S | 75 ± 1 | 95 ± 6 | 53 ± 3[a] |
| HVHP428 | 92 ± 1 | 65 ± 2 | 87 ± 1 |
| HVHP428S | 98 ± 4 | 82 ± 3 | 90 ± 13 |
| HVHP420 | 80 ± 12 | 52 ± 0 | 77 ± 2 |
| HVHP420S | 100 ± 14 | 52 ± 10 | 100 ± 2 |
| HVHP414 | 72 ± 6 | 35 ± 3 | 9 ± 7 |
| HVHP414S | 74 ± 1 | 49 ± 9 | 57 ± 15 |
| HVHP423 | 61 ± 6 | 88 ± 21 | 100 ± 15 |
| HVHP423S | 82 ± 15 | 97 ± 29 | 68 ± 30 |
| HVHP413 | 29 | 63 | 100 |
| HVHP413S | 100 | 76 | 100 |
| HVHP426 | 84 ± 3 | 69 ± 2 | 85 ± 6 |
| HVHP426S | 76 ± 3 | 97 ± 15 | 100 ± 1 |

[a]The pepsin resistance is an under-estimation.

Example 7: Sequence Identities Between $V_H$s and Between $V_L$s

Sequence identities between the $V_H$s, as well as $V_L$s were determined. Only FR sequences were included in the analysis, i.e., CDR sequences were excluded.

The sequences of $V_H$ pairs or $V_L$ pairs were aligned using ClustalW (Thompson et al, 1994), and the percentage identity between the $V_H$ pairs or $V_L$ pairs was calculated using the BioEdit Sequence Alignment Editor.

The biophysical consequences of Cys pair substitutions at positions 49 and 69 for $V_H$s and 48 and 64 for $V_L$s are shown to be universal irrespective of their sequence, germline origin, and CDR length and composition. The $V_H$s have diverse germline origin and CDR lengths and amino acid composition. In particular, CDR3 length and composition is more diverse. Nonetheless, independent of these structural variations, the introduction of Cys pairs at positions 49 and 69, leads to the formation of Cys49/Cys69 disulfide linkage and significant improvements in non-aggregation, thermal stability and protease stability of $V_H$s without compromising their expression yields. The 32 $V_L$s described in WO 2006/099747 are diverse: they belong to both kappa and lambda families and have diverse V segment and J segment germline origin and CDR amino acid compositions and lengths. The length of CDR3, in particular ranges from 6 to 11 amino acids. 8 non-aggregating $V_L$s representing different classes (FIG. 1B) were chosen from the aforementioned 32 to assess the biophysical consequences of Cys48/Cys64 substitution. As in the case of $V_H$s, a side by side analysis of the 8 $V_L$s and their Cys mutant versions, showed that independent of structural variations, the introduction of Cys pairs at positions 48 and 64, leads to the formation of Cys48/Cys64 disulfide linkage and significant improvements in thermal stability and protease stability of $V_L$s without compromising their non-aggregation status or expression yields.

Figure 10:
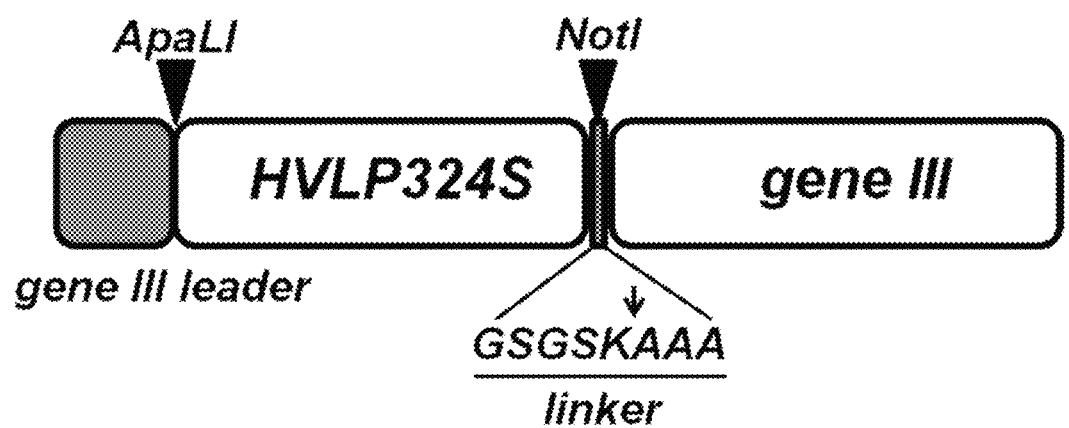
FIG. 10 shows the schematic drawing of fd-tetV$_L$24S vector. A HVLP324S gene carrying a linker sequence at its 3' end was prepared by PCR, digested with ApaLI and NotI restriction enzymes and subsequently cloned into fd-tet-GIIID (Tanha et al., 2001) phage DNA that was linearized by ApaLI and NotI restriction enzymes. This places HVLP324S with the linker between phage gene III leader and gene III open reading frame sequences. The DNA linker sequence encodes a GSGSKAAA (SEQ ID NO: 86) polypeptide wherein the lysine residue provides a trypsin cleavage site (marked by arrow). This allows eluting bound phages from target antigens by adding trypsin following the binding step in panning of antibody phage display libraries.

Example 8: Construction of a Disulfide-stabilized $V_L$ Phage Display Library The HVLP324S $V_L$ phage display library was constructed in two steps by the method described by Hussack et al. (In press (c)). First, a library with a randomized CDR3 was constructed based on the HVLP324S $V_L$ scaffold (FIG. 10). Then, the CDR3-randomized library was used as scaffold to construct the final library with all 3 CDRs randomized.

(i) Construction of the CDR3-Randomized $V_L$ Phage Display Library

Phage ssDNA containing uridine instead of thymidine (dU-ssDNA template) was prepared as described (Hussack et al. In press (c)), except that the phage used for ssDNA preparation was fd-tetV$_L$24S. fd-tetV$_L$24S is fd-tetGIIID phage (Tanha et al., 2001) with the HVLP324S $V_L$ gene in its genome and fused with the phage p3 gene (FIG. 10). Incorporation of uridine into phage ssDNA was confirmed by titering the phage against TG1 and CJ236 E. coli cells as described (Hussack et al. In press (c)). A total of 75 µg fd-tetV$_L$24S ssDNA in ddH$_2$O was prepared. In vitro synthesis of heteroduplex DNA with simultaneous randomization of CDR3 using primers V$_L$24-CDR3, V$_L$24-CDR3a, and V$_L$24-CDR3b was performed as described (Hussack et al. In press (c)). Primers were phosphorylated (Hussack et al. In press (c)) and used in annealing reactions. Three separate annealing reactions were performed at 93° C. for 5 min, 50° C. for 15 min, 20° C. for 20 min in a total volume of 15 µL with 8.2 µL of 121.5 ng/µL fd-tetV$_L$24S dU-ssDNA, 0.33 µL of phosphorylated primers V$_L$24-CDR3, V$_L$24-CDR3a, or V$_L$24-CDR3b, 1 µL of the mix (2 µL 10×TM buffer [500 mM Tris-HCl, 100 mM MgCl$_2$, pH 7.5], 2 µL 10 mM ATP, 1 µL 100 mM DTT, 15 µL ddH$_2$O), and 1.5 µL 10×TM buffer. Covalently closed circular DNA (CCC-DNA) was synthesized as described (A total of 100 µg CCC-DNA in ddH$_2$O was prepared and concentrated by a SpeedVac™ to 82.5 µg in 255 µL (323 ng/µL). Twenty-three transformations (11 µL CCC-DNA plus 350 µL of electrocompetent E. coli TG1) were carried out as described. Following incubation in SOC medium, transformation materials were titrated and grown in 1 L of 2×YT/tetracycline (12.5 µg/mL) overnight at 37° C. and 180 rpm. In the morning, the cells were harvested and frozen library stocks were made as described. The cell density of the frozen library stocks were estimated by $A_{600\ nm}$ measurements. The amplified library phage was purified from the supernatant, titred, (See Hussack et al (c)) and used as the starting material to construct the final library (see Section (ii)). From the titration experiments on the transformation materials (see above) the library size (number of transformants) was determined to be 2.3×10$^8$.

(ii) Construction of the CDR1/CDR2/CDR3-Randomized $V_L$ Phage Display Library

In the second step of the library construction, CDR1 and CDR2 were randomized. dU-ssDNA template was prepared starting with 4×10$^{12}$ cfu CDR3-randomized library phage from above (see Hussack et al (c)). 200 µg of ssDNA was obtained from 2 mL of phage (2×10$^9$/µL). Incorporation of uridine into phage ssDNA was confirmed as above. The dU-ssDNA template was used in the second round of mutagenesis which used mutagenic oligonucleotides V$_L$24-CDR1 and V$_L$24S-CDR2. Annealing and CCC-DNA synthesis steps were essentially identical to those described above. A total of 300 µg CCC-DNA in 1 mL ddH$_2$O was prepared. Seventy-seven transformations (13 µL CCC-DNA plus 200 µL of electrocompetent E. coli TG1) were carried out as described. Following incubation in SOC medium, transformation materials were titrated and grown in 3 L of 2×YT/tetracycline (5 µg/mL) overnight at 180 RPM and 37° C. Frozen library stocks were made and its cell density was estimated as described above. The library phage was purified from the supernatant in a final volume of 20 mL PBS, titred against TG1, and stored frozen at −80° C. in 500 µL aliquots for future first round panning as the input phage. The library size was determined to be 1×10$^8$ transformants. 78 $V_L$ clones from the library (non-amplified library) titer plates were subjected to sequencing as described in Hussack et al (c).

HVLP324S $V_L$ was used as the scaffold for construction of a disulfide-stabilized synthetic $V_L$ library. HVLP324S is the mutant version of the previously described HVLP324 but with an additional disulfide linkage between Cys48 and Cys64. The HVLP324S $V_L$ phage display library was constructed by introducing diversity at 16 (CDR3=9 amino acids), 17 (CDR3=10 amino acids), and 18 (CDR3=11 amino acids) locations in all 3 CDRs essentially as described for a previously described HVLP324 $V_L$ phage display library (FIG. 11, Hussack et al (c)). The library size was modest with 1×10$^8$ transformants. Sequence analysis of 78 $V_L$ clones from the non-amplified library showed diversity had been introduced in all CDR positions with a biased randomization in favour of the parental $V_L$ (HVLP324S) amino acid residues. Sequencing of 78 clones showed that 2 were identical to wild-type HVLP324S, 8 had wild type sequences for CDR1, 2 had wild type sequences for CDR2, 18 had wild type sequences for CDR3, 9 had wild type sequences for both CDR1 and CDR2, 1 had wild type sequence for both CDR2 and CDR3, and 2 had wild type sequences for both CDR1 and CDR3. The presence of these clones in the library contributes to the aforementioned sequence bias.

A CDR3 length distribution analysis of the 76 library clones showed that the majority (71%) of the library clones had a CDR3 length of 9 amino acids. Clones with CDR3 lengths of 10 and 11 amino acids were at 18% and 11%, respectively.

Additional details of the library design, construction and characterization are provided in the legend and figure for FIG. 11. Specific oligonucleotides used are as provided in Table 6, where IUPAC nomenclature is used to designate degenerate nucleotide residues at positions indication by N, K and R.

TABLE 6

List of oligonucleotides used for molecular cloning.

| Name | Sequence (5'->3') | Purpose | SEQ ID |
|---|---|---|---|
| $V_L24$-CDR1 | AGA GTC ACC ATC ACT TGC NNK GCA AGT CAG RGC ATT NNK NNK NNK TTA NNK TGG TAT CAG CAG AAA CCA | Mutagenesis | 87 |
| $V_L24S$-CDR2 | CCT AAA CTC CTG TGC TTT NNK GCA TCC NNK CKN NNK AGT GGG GTC CCA TCA AGG | Mutagenesis | 88 |
| $V_L24$-CDR3 | TTT GCA ACT TAC TAC TGT NNK CAG NNK NNK NNK NNK CCT NNK ACG TTC GGC CAC GGG ACC | Mutagenesis | 89 |
| $V_L24$-CDR3a | TTT GCA ACT TAC TAC TGT NNK CAG NNK NNK NNK NNK CCT NNK NNK ACG TTC GGC CAC GGG ACC | Mutagenesis | 90 |
| $V_L24$-CDR3b | TTT GCA ACT TAC TAC TGT NNK CAG NNK NNK NNK NNK CCT NNK NNK NNK ACG TTC GGC CAC GGG ACC | Mutagenesis | 91 |
| -96GIII | CCC TCA TAG TTA GCG TAA CGA TCT | Colony-PCR Sequencing | 92 |
| fdTGIII | GTG AAA AAA TTA TTA TTC GCA ATT CCT | Colony-PCR Sequencing | 93 |
| $HV_L24$-BamHI | TTG TTC GGA TCC TAG GAC GGT CAC CT | Subcloning | 94 |
| $HV_L24$-BbsI | TAT GAA GAC ACC AGG CCG ACA TCC AG | Subcloning | 95 |
| KT124 | TGT GCT ACC ACC ACT ACT ACT AAT AGC GCA GAC CCA CTC CAG CCC CTT CCC TGG | Mutagenesis | 96 |
| KT125 | CAC GGT GTT CTT GGA ATT GTC TCT GGA GCA GGT GAA TCG GCC CTT CAC GGA GTC | Mutagenesis | 97 |
| M13RPb | CAG GAA ACA GCT ATG AC | Colony-PCR Sequencing | 98 |

N: A, T, G, or C.
K: T or G.
R: A or G.

Example 9: Validation of the Disulfide-Stabilized $V_L$ Phage Display Library

To validate HVLP324S $V_L$ phage display library, the library was subjected to selection for binders to two different test antigens, namely human lysozyme and human serum albumin (HSA). Positive candidate binders (phage-displayed $V_L$s) identified by initial binding assays (phage ELISA) were subcloned in vectors for expression in *E. coli*. $V_L$ binders were expressed, purified and analyzed for affinity and stability.

Example 9a: Panning

Selection for anti-human lysozyme $V_L$s was performed by standard panning techniques (see for example, Lee et al., 2007; Arbabi-Ghahroudi et al., 2009a). Briefly, a Nunc microtiter well (VWR International, Ltd., Mississauga, ON, Canada) was coated with 100 µL of 1 mg/mL human lysozyme (Sigma-Aldrich, Mississauga, ON, Canada) in sterile PBS (3.2 mM $Na_2HPO_4$, 0.5 mM $KH_2PO_4$, 1.3 mM KCl, 135 mM NaCl, pH 7.4) overnight at 4° C. The well was washed 3× with sterile PBS, blotted on a paper towel, and blocked with 150 µL of 2% (w/v) milk in sterile PBS (2% MPBS) at 37° C. for 2 h. The blocking agent was removed from the well and 100 µL of library phage (amplified phage prepared in Example 8, Section (ii) in 1% MPBS ($5\times10^{11}$ cfu; preincubated at 37° C. for 1.5 h) were added to the well and incubated for 1.5 h at 37° C. After 10× washes with PBST (0.05% (v/v) Tween-20 in sterile PBS), phage were eluted by incubating the well with 100 µL of freshly prepared 124 mM triethylamine for 10 min at room temperature, pipetting up and down at 8 min. The eluted phage solution was neutralized in a 1.5 mL microtube by mixing with 50 µL of 1 M Tris-HCl, pH 7.5 and kept on ice until the infection phase. 2×5 mL of exponentially growing *E. coli* TG1 cells ($OD_{600}$=~0.5) was prepared (Arbabi-Ghahroudi et al., 2009a) in 50 mL sterile Falcon tubes from which 2 mL was infected at 37° C. for 30 min with 145 µL of eluted phage (5 µL was kept aside for determining the titer of the eluted phage as described below). The infected cells were centrifuged at 4,000 rpm and 4° C. for 20 min using Sorval Legend RT rotor and centrifuge (Thermo Fisher Scientific, Nepean, ON, Canada), the supernatant was removed, and the pellet was resuspended in 1 mL of 2×YT and equally spread onto 3 large Petri dishes with 2×YT agar/5 µg/mL tetracycline (2×YT/Tet). The Petri dishes were incubated at 37° C. overnight. Next day, the amplified phage were recovered from the large Petri dishes. Briefly, 10-15 mL of sterile PBS (volume added according to the colony density) was added to each plate, the cells were scraped off using a glass spreader, and collected in sterile 50 mL sterile Falcon tubes. The cells were scraped off once more as before and pooled with the previous ones. The suspension was fractionated into cell pellet and supernatant by centrifugation for 20 min at 4,000 rpm and 4° C. using Sorval Legend RT rotor and centrifuge (Thermo Fisher Scientific). The amplified phage were purified from the supernatant essentially as described (Lee et al., 2007). Briefly, to the phage supernatant that was prefiltrated with sterile 0.22 µm filter was added a 1/5 volume of 20% PEG-8000/2.5 M NaCl in 50 mL sterile Falcon tubes, and the mixture was incubated on ice for 1 h. The solution was centrifuged for 20 min at 4,000 rpm and 4° C. using Sorval Legend RT rotor and centrifuge (Thermo Fisher Scientific). The phage pellet was redissolved in 3 mL of sterile PBS, transferred to a 15-mL sterile Falcon tube, mixed with 1/5 volume of 20% PEG-8000/2.5 M NaCl (0.6 mL), and incubated on ice for 20 min. The phage solution was centrifuged at 4,000 rpm and 4° C. for 20 min using Sorval Legend RT rotor and centrifuge (Thermo Fisher Scientific), and the phage pellet was dissolved in 0.5-1 mL sterile PBS, dissolution volume depending on the size of the pellet. The phage solution was aliquoted in 0.1 mL volumes in a sterile 1.5-mL sterile microtube. The titer of the amplified phage was determined as described below.

For the second round of panning, in parallel with the conventional panning described above, thermopanning was also performed where the amplified phage in sterile PBS from the first round was heated at 65° C. for 2 h in a 1.5 mL sterile microtube, subsequently centrifuged, and the phage supernatant was added to the human lysozyme-coated well for binding (in the second round of panning). All the remaining steps were the same for both methods of panning. Parallel pannings were continued for two more rounds. Washes were 12×, 15×, and 15× for the second, third and fourth rounds of panning, respectively.

Panning (conventional panning) against human serum albumin was performed as described for human lysozyme except that no thermopanning in parallel was performed. Following panning, standard phage ELISA (Harrison et al., 1996; Tanha et al., 2001; Hussack et al., In press (c)) was performed on clones from titer plates (obtained from eluted phage) to identify phage displaying $V_L$s positive for binding to human lysozyme or serum albumin.

Example 9b: Phage Titer Determination

Standard techniques were used to determine phage titers. To determine the titer of the eluted phage, dilutions of the eluted phage were made in PBS at $10^{-1}$-$10^{-4}$ (2µL of phage was added to 18 µL of PBS to make the $10^{-1}$ dilution and so on). 10 µL of each dilution was mixed with 100 µL of exponentially growing E. coli TG1 cells ($OD_{600}$=~0.5), and the mixtures were incubated at 37° C. for 30 min for phage infection of E. coli TG1 cells to occur. The infected TG1 cells were plated on 2×YT/Tet agar Petri dishes and incubated at 37° C. overnight. The number of colonies was used to determine the titer (cfu/mL) of the eluted phage. Colony-PCR on colonies was performed to verify the presence of inserts (positive hits gave a size of around 500 bp) and to provide templates for DNA sequencing using fdTGIII and –96GIII primers (Table 6). Sequences were analyzed and manipulated by DNASTAR Lasergene 8.

Briefly, to determine the titer of the amplified phage (input phage), phage dilutions were made at $10^{-3}$, $10^{-6}$, $10^{-8}$, and $10^{-10}$. 10 µL of each diluted phage was mixed with 100 µL of exponentially growing TG1 cells, and the mixtures were incubated at 37° C. for 30 min for phage infection of cells to occur. Subsequently, using sterile disposable spreaders, the phage infected cells were spread on Petri dishes with 2×YT r/Tet agar media and left in clean bench for 5 min. Plates were incubated overnight at 37° C. In the morning, the colony titers on the plates were used to determine the titer of the amplified phage.

To show the utility of the library, the library was panned against human lysozyme and human serum albumin for four rounds. In the instance of the panning against human lysozyme, a conventional panning was performed in the first round followed by conventional panning and thermopanning in parallel from the $2^{nd}$ round on. In the thermopanning approach, the input phage was incubated at 65° C. for 2 h, centrifuged to remove any possible aggregates, and the supernatant was added to the lysozyme-coated well for binding. In the conventional panning approach, the input (amplified) phage was directly added to the lysozyme-coated well without the heat treatment. The thermopanning was applied to see if it preferentially enriches for stable (thermostable and/or non-aggregating) $V_L$ binders compared to the conventional panning which was expected to be indiscriminate with regards to stable and unstable $V_L$ binders.

Table 7 shows the results of panning against human lysozyme with respect to the output phage titer (or eluted phage titer). In general, the output phage titers are 3-4 orders of magnitude lower for the thermopanning approach compared to the conventional one. This may be due to lower input phage titers used and further loss of phage (possibly aggregating phage-displayed $V_L$s) to aggregation during the heat treatment (data not shown).

TABLE 7

Phage titers for pannings performed under room temperature (conventional panning) versus 65° C.-2 h (thermopanning) selection conditions. Data are for panning against human lysozyme. cfu: colony-forming units.

| Panning round | Room temperature | | 65° C.-2 h | |
| --- | --- | --- | --- | --- |
| | Input (cfu) | output (cfu) | Input (cfu) | output (cfu) |
| 1 | $5 \times 10^{11}$ | $7 \times 10^4$ | N/A | N/A |
| 2 | $4 \times 10^{10}$ | $2 \times 10^5$ | $4 \times 10^{10}$ | $2 \times 10^2$ |
| 3 | $7 \times 10^{11}$ | $2 \times 10^5$ | $2 \times 10^{10}$ | $6 \times 10^4$ |
| 4 | $5 \times 10^{11}$ | $6 \times 10^7$ | $5 \times 10^{10}$ | $7 \times 10^4$ |

Figure 12:
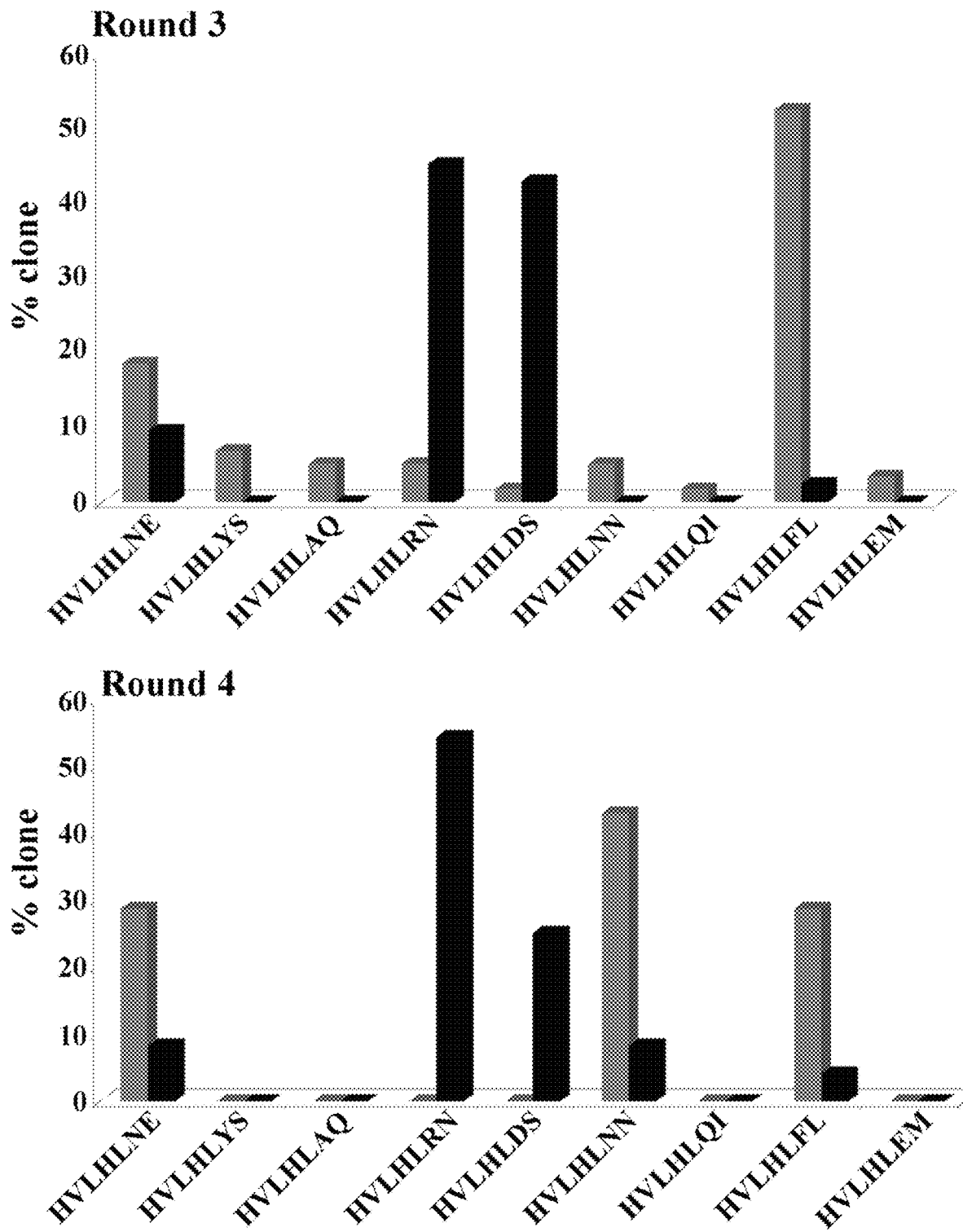
FIG. 12 shows phage selection of $V_L$s that bind to human lysozyme. Frequency (%) of anti-human lysozyme $V_L$s selected from phage pannings (round 3 and 4) under two different selection conditions (Room temperature and 65° C.-2 h) was shown by grey or black rectangular columns, respectively.
Figure 16A:
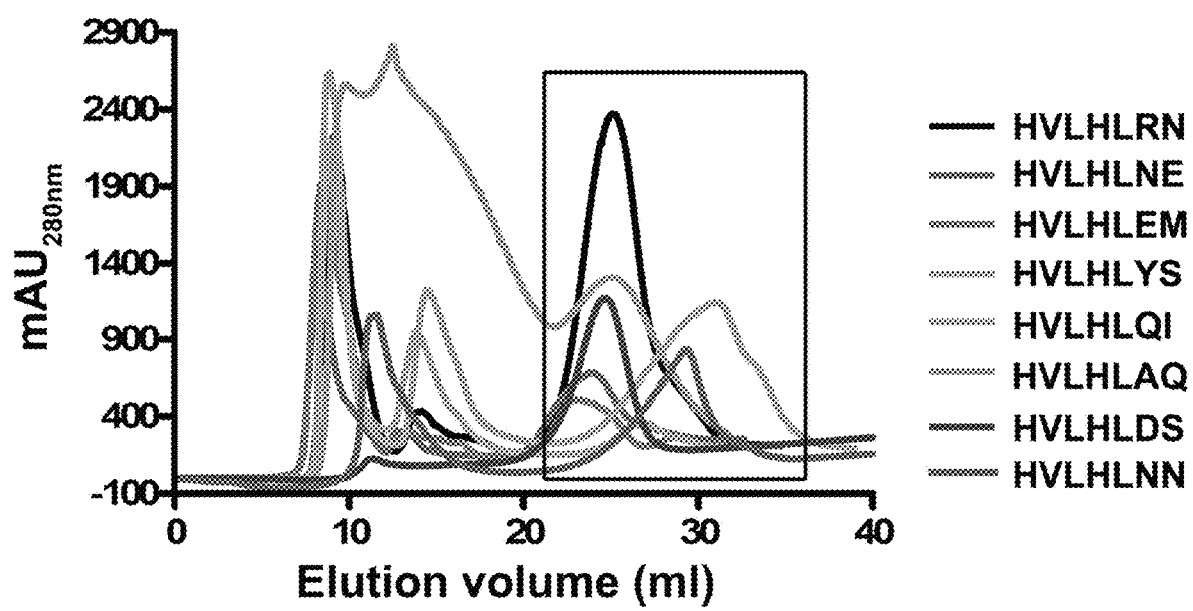
FIGS. 16A and 16B show the IMAC purification of anti-human lysozyme $V_L$s and SDS-PAGE analysis.
Figure 16B:
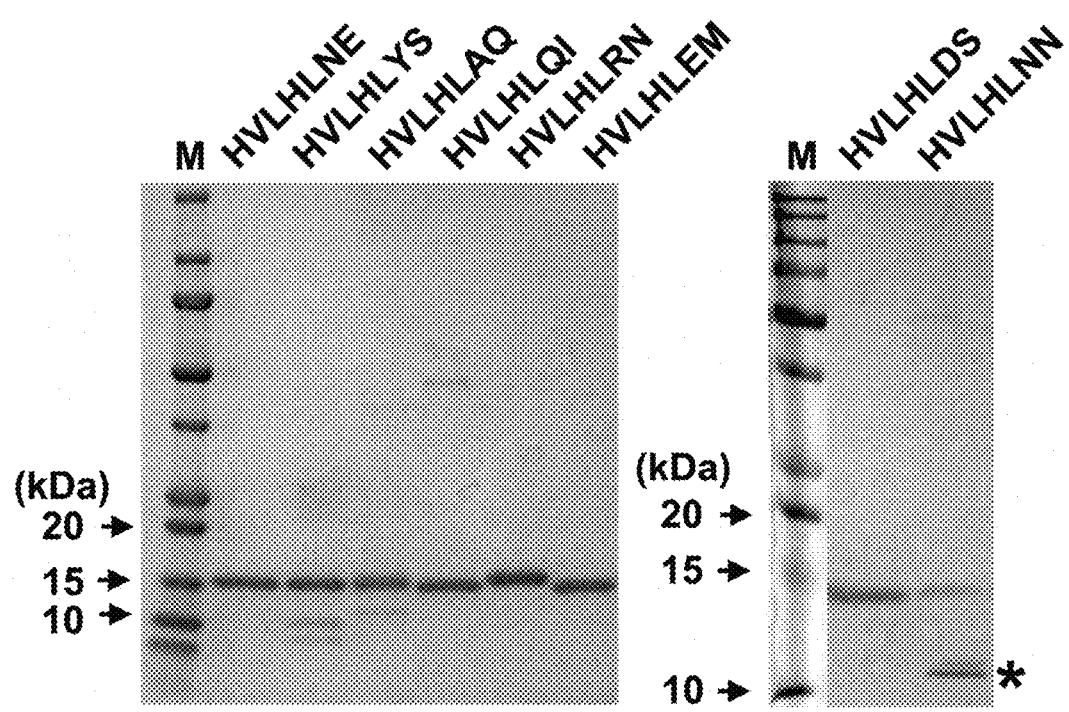

Phage ELISA and sequence analyses from round 3 and 4 identified 9 anti-human lysozyme $V_L$s with variable affinities to immobilized human lysozyme (FIG. 13 and Table 8). After 4 rounds of panning, of the total of 177 $V_A$S (101 $V_L$s and 76 $V_L$s for rounds 3 and round 4, respectively) analyzed, 5 clones of the total of 9 identified in round 3 survived: HVLHLRN; HVLHLDS; HVLHLNE; HVLHLNN; HVL-HLFL (FIG. 12). These were represented at 54.2% and 25% for HVLHLRN and HVLHLDS, respectively, followed by 8.3%, 8.3%, and 4.2% for HVLHLNE, HVLHLNN, and HVLHLFL, respectively, in the thermopanning approach (65° C., 2 h). In contrast, with the conventional panning approach (room temperature [RT]), HVLHLRN and HVLHLDS were not represented, and HVLHLNE, HVLHLNN, and HVLHLFL were occurred at relative frequencies of 28.6%, 42.9%, and 28.6%, respectively (FIG. 12). HVLHLRN and HVLHLDS were also the predominant clones in round 3 of thermopanning and marginally present in the round 3 of conventional panning. HVLHLYS, HVLHLAQ, HVLHLQI, and HVLHLEM were not selected by either the conventional panning or thermopanning in round 4 panning.

purified by standard techniques as described for other domains. Since $V_L$s had His6 tags at their C-termini, they were purified by immobilized-metal affinity chromatography. FIG. 16A shows the IMAC chromatogram profiles of the purified $V_L$s that shows the $A_{280}$ range of 400 mAU (HVLHLEM) to 2400 mAU (HVLHLRN) for the highest elution peaks. The SDS-PAGE profiles of the $V_L$s shows the $V_L$s are highly pure (FIG. 16B). The expression yield of HVLHSA1 was also high as judged from its IMAC chromatogram profile (data not shown). Thus the $V_L$s can be expressed in high yields in *E. coli* with high purity.

TABLE 8

Properties of anti-human lysozyme and anti-human serum albumin VLS isolated from rounds 3 and 4 of panning.

| $V_L$ | $K_D$ (μM) | $T_m$ (°C.) | Monomer/Agg. | Selection |
|---|---|---|---|---|
| HVLHLRN (SEQ ID NO: 101) | 0.05 | 74 | Monomer | 65° C.-2 h |
| HVLHLDS (SEQ ID NO: 100) | 6.1 | 68.3 | Monomer | 65° C.-2 h |
| HVLHLEM (SEQ ID NO: 104) | >73 | 72.2 | Monomer | RT |
| HVLHLAQ (SEQ ID NO: 103) | 0.2 | 66.5 | Agg. (7%) | RT |
| HVLHLQI (SEQ ID NO: 105) | 2.6 | 62 | Agg. (17%) | RT |
| HVLHLNE (SEQ ID NO: 102) | 0.06 | 62 | Agg. (13%) | RT/65° C.- 2 h |
| HVLHLYS (SEQ ID NO: 106) | 6.4 | 66.8 | Agg. (7%) | RT |
| HVLHLNN (SEQ ID NO: 99) | 0.2 | 62.6 | Agg. (12%) | RT/65° C.- 2 h |
| HVLHLFL (SEQ ID NO: 108) | ND | ND | ND | RT/65° C.-2 h |
| HVLHSA1 (SEQ ID NO: 107) | 0.8 | 71 | Monomer | RT |

ND, not determined;
RT, room temperature
Agg., aggregate.
%'s are % aggregates.

Following 4 rounds of panning against human serum albumin, screening of 50 clones by phage ELISA and sequencing revealed one predominant $V_L$, namely, HVLHSA1 (FIG. 13; Table 8) which was positive by phage ELISA for binding to human serum albumin.

All the 10 anti-lysozyme and anti-albumin phage-$V_L$ binders were subsequently processed for further characterization as described below.

Example 9c: Biophysical Characterization of Anti-Human Lysozyme and Anti-Human Serum Albumin $V_L$s Starting with phage-displayed $V_L$ clones, $V_L$s were cloned, expressed, and purified by standard techniques as described above for other antibody domains. The $V_L$s were subsequently analyzed by size exclusion chromatography for aggregation status, by CD for thermostability, and by surface plasmon resonance for their binding affinity and specificity.

Figure 3C:
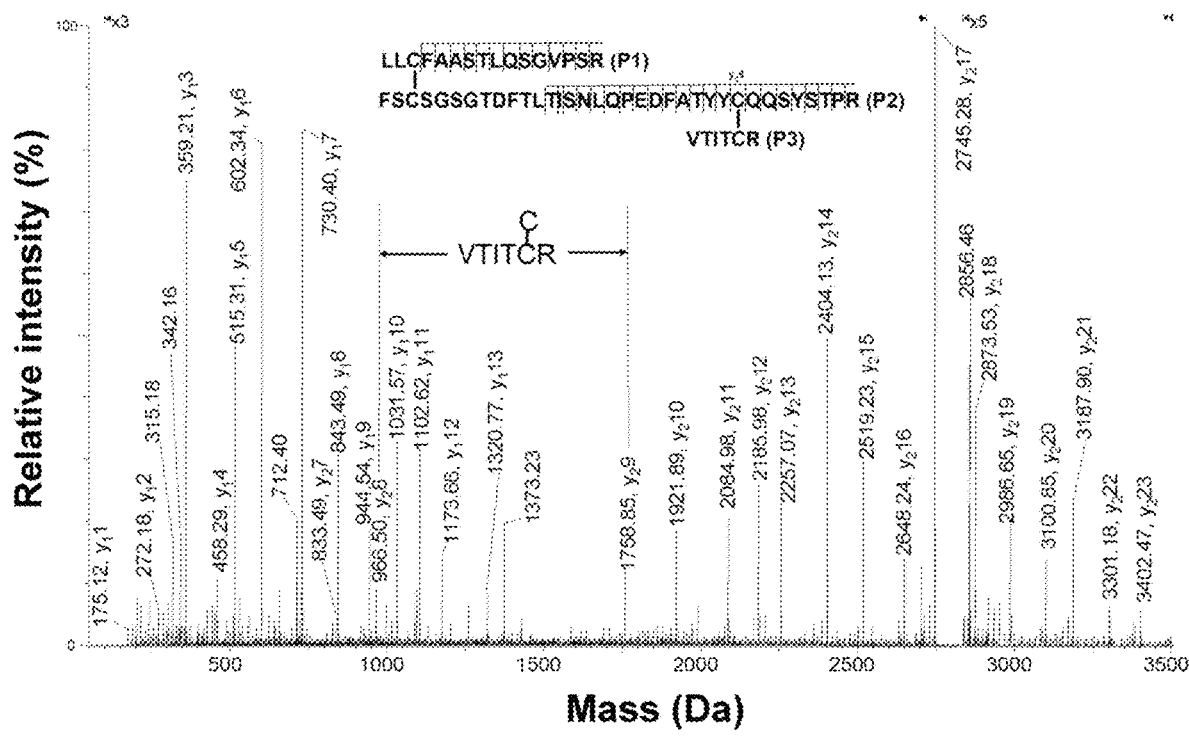
FIG. 3C is a CID-MS$^2$ spectrum of the disulfide linked peptide ion at m/z 1042.66 (6+) from HVLP324S tryptic peptide corresponding to the disulfide-linked peptide LLCFAASTLQSGVPSR (P1) (SEQ ID NO: 43), FSCSGS-GTDFTLTISNLQPEDFATYYCQQSYSTPR (P2) (SEQ ID NO: 44), and VTITCR (P3) (SEQ ID NO: 42) which was observed from the survey of LC-MS chromatogram. Very informative y fragment ions were observed from P2 with P3 as a modification via a disulfide bond. An almost complete y ion series of P1 was observed as well. The disulfide linkage was further confirmed by a ETD-MS$^2$ spectrum of the peptide ion [M+5H]$^{5+}$ at m/z 1250.99 (5+) from the same disulfide-linked peptide of HVLP324S through which the intact P1, P2, and P3 ions at m/z 691.47 (1+), 1648.86 (1+), and 1956.85 (2+), respectively, were all observed at relatively high abundances upon dissociation of the disulfide linkages of the three peptide fragments by the ETD (data not shown).
Figure 14A:
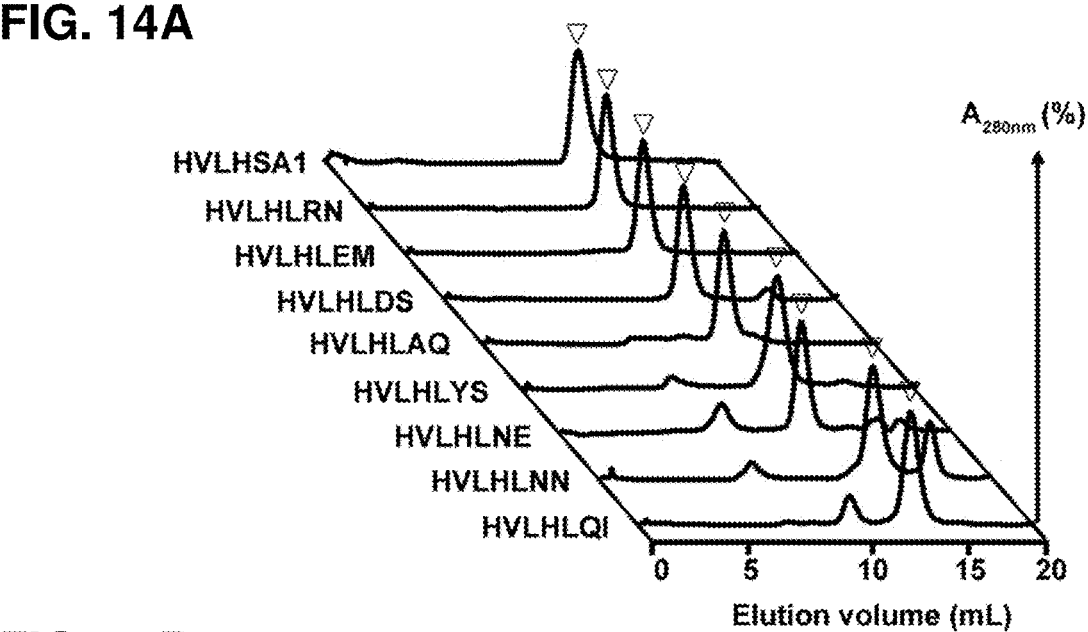
FIGS. 14A-14C show non-aggregation state and thermostability of anti-human lysozyme $V_L$s.

Nine anti-human lysozyme $V_L$s and HVLHSA1 $V_L$ (FIG. 13; Table 8) were cloned and expressed in *E. coli* and Subsequently, $V_L$s were analyzed for their aggregation behaviour by Superdex™ 75 size exclusion chromatography. % aggregate (or % monomer) for each $V_L$ was also determined as described (Arbabi-Ghahroudi et al. 2010). As shown in FIG. 14A, 3 anti-human lysozyme $V_L$s (HVLHLRN, HVLHLEM, and HVLHLDS) were purely monomeric (non-aggregating), while the rest of the $V_L$ binders were aggregating with % aggregates ranging from 7% to 17% (Table 8). HVLHSA1 $V_L$ was also analyzed by size exclusion chromatography as described for other domains. The chromatogram gave a symmetrical monomeric peak demonstrating the $V_L$ was 100% non-aggregating monomer (FIG. 14A; Table 8). These results show that the $V_L$ (or $V_H$) libraries with the non-canonical Cys48/Cys64 (or Cys49/Cys69) disulfide linkage feature yields non-aggregating binders.

Figure 14B:
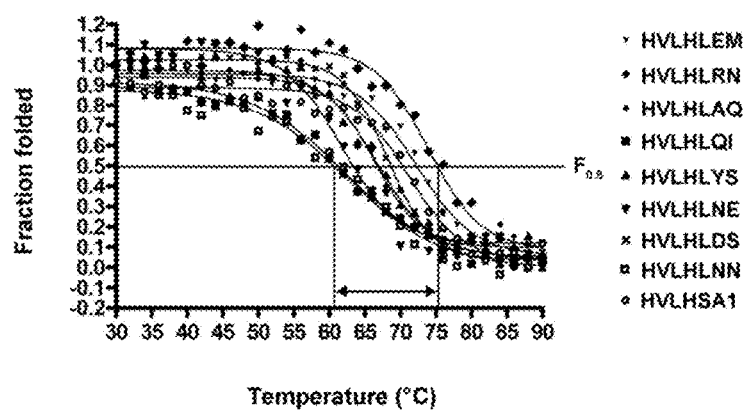
Figure 14C:
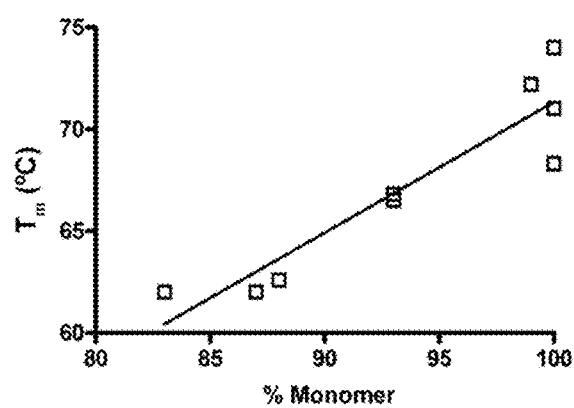

To obtain a measure of the thermostability of the $V_L$ binders, melting temperatures ($T_m$s) of the $V_L$s were determined by CD as described previously for other domains. FIG. 14B shows the melting profiles of the anti-human lysozyme $V_L$s which are in the range of 62° C. to 74° C. The calculated $T_m$s are recorded in Table 8. The $T_m$ of anti-albumin HVLHSA1 was also determined and shown to be high: 71° C. (FIG. 14B; Table 8). These $T_m$s are significantly higher than $V_L$s without the non-canonical disulfide linkage, demonstrating that the $V_L$ (or $V_H$) libraries with the non-canonical Cys48/Cys64 (or Cys49/Cys69) disulfide linkage feature yields more stable binders. In the instance of human lysozyme panning, HVLHLRN and HVLHLDS which are non-aggregating (Table 8) and have the highest $T_m$s were also the clones which were enriched very significantly over aggregating, less thermostable ones by thermopanning and not by conventional panning. This demonstrates that although both panning approaches yield non-aggregating, thermostable binders, thermopanning is more efficient in enriching them. (The fact that HVLHLEM which was both non-aggregating and thermostable and yet was not selected in round 4 by thermopanning could be due to its very low affinity during the binding stage of the panning [FIG. 12; Table 8]). FIG. 14C shows that there is strong positive correlation between $T_m$ and % monomer of the anti-lysozyme and anti-albumin $V_L$s ($R^2$=0.8568; P value (two-tailed)=0.0013, Spearman r=0.9061), meaning that the higher the $T_m$ of a $V_L$, the more likely the $V_L$ is non-aggregating. This also means that since $V_L$/$V_H$ libraries with the non-canonical disulfide linkage feature yield more thermostable $V_L$/$V_H$ binders than libraries without this feature, they also yield more non-aggregating $V_L$/$V_H$ binders. As therapeutics non-aggregating and thermostable $V_L$/$V_H$ binders are more efficacious.

Figure 15:
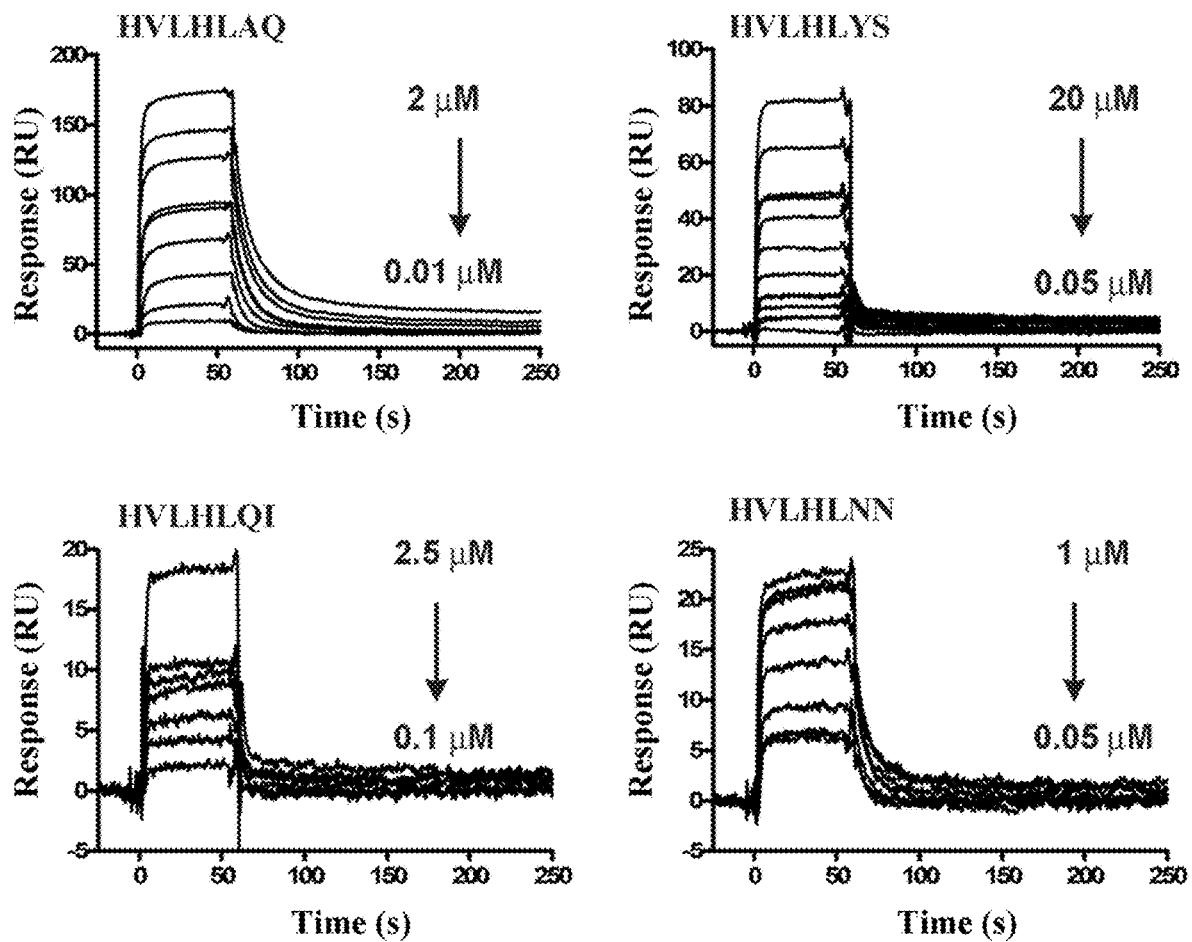
FIG. 15 shows SPR analysis of anti-human lysozyme $V_L$s. Biacore sensorgrams showing the binding of human lysozyme to immobilized anti-human lysozyme $V_L$s at diverse range of concentrations indicated on each sensorgram: 10, 25, 25, 100, 200, 200, 500, 750 and 2000 nM for HVLHLAQ; 100, 250, 500, 1000, 1000, 2500, 5000, 7500, 10000 and 10000 nM for HVLHLDS; 750, 1000, 2500, 5000, 7500, 10000, 15000 and 20000 nM for HVLHLEM; 10, 25, 50, 100, 250, 250, 500, 750 and 1000 nM for HVLHLNE; 50, 50, 100, 250, 500, 750, 1000 and 1000 nM for HVLHLNN; 100, 250, 500, 750, 1000, 1000 and 2500 nM for HVLHLQI; 10, 25, 50, 100, 200, 200, 500, 750 and 1000 nM for HVLHLRN; 50, 100, 250, 500, 1000, 1000, 2500, 5000, 7500, 10000, 10000, 15000 and 20000 nM for HVLHLYS.
Figure 15:
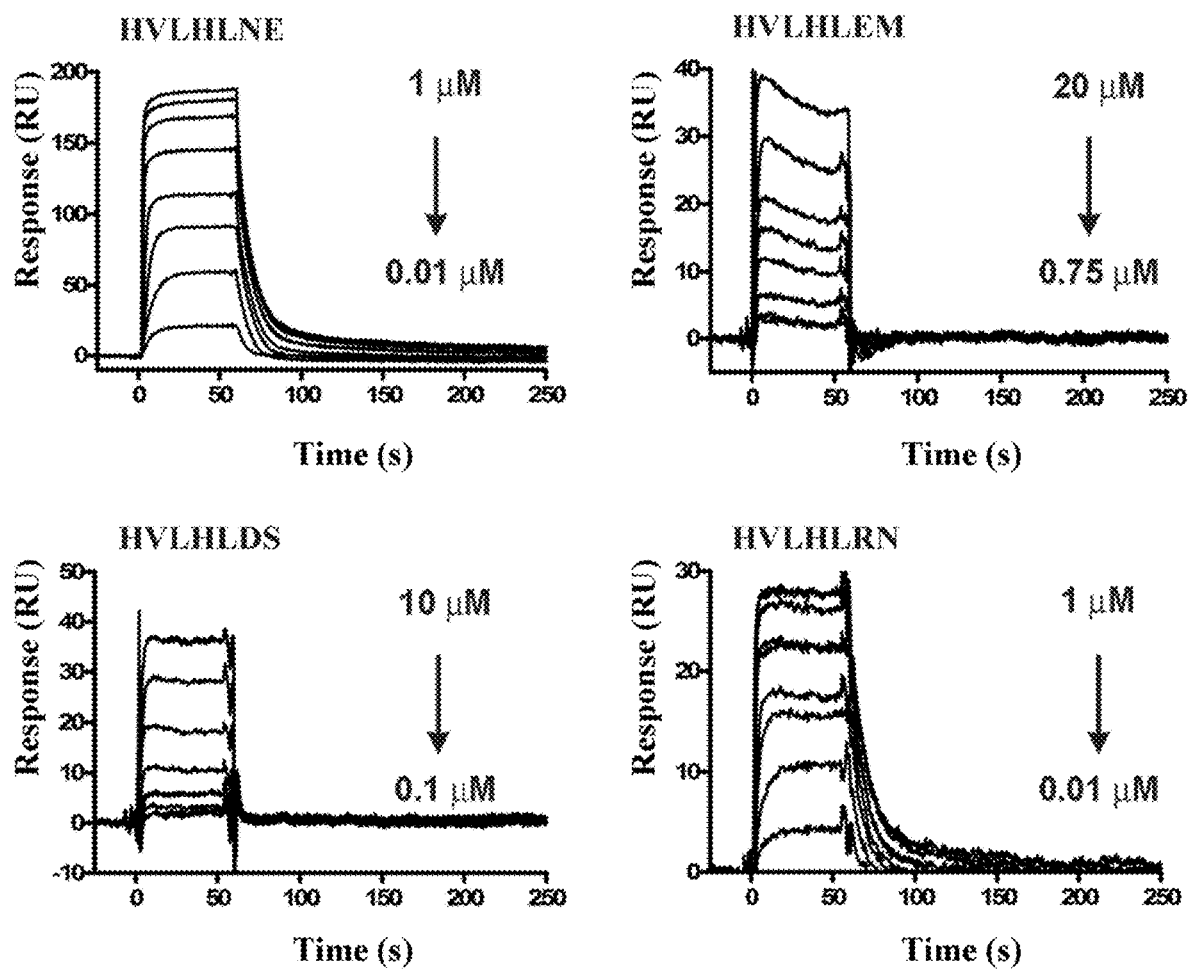

The affinities ($K_D$s) of the anti-human lysozyme $V_L$s to their antigen, human lysozyme, was also determined. The binding of human lysozyme to immobilized anti-human lysozyme $V_L$ binders was determined by surface plasmon resonance (SPR) using BIACORE 3000 (GE Healthcare). 298 resonance units (RUs), 312 RUs, 295 RUs, 339 RUs, 315 RUs, 412 RUs, 370 RUs, 345 RUs, and 349 RUs of each $V_L$ binders (HVLHLAQ, HVLHLNE, HVLHLEM, HVLHLYG, HVLHLRN, HVLHLNN, HVLHLQI, HVLHLYS, and HVLHLDS, respectively) was immobilized on a research grade CM5 sensor chip. Immobilizations were carried out at concentrations of 10 μg/mL in 10 mM acetate at pH 4.5 using the amine coupling kit supplied by the manufacturer. Human lysozyme was passed through a Superdex 75 column (GE Healthcare) in HBS-EP buffer (10 mM HEPES, pH 7.4, 150 mM NaCl, 3 mM EDTA and 0.005% P20 surfactant) with flow rate of 0.5 mL/min to eliminate any possible aggregates prior to Biacore analysis. For the binding studies, analyses were carried out at 25° C. in 10 mM HEPES, pH 7.4 containing 150 mM NaCl, 3 mM EDTA and 0.005% surfactant P20. The flow rates used were 20 μL/min. For regeneration the surfaces were washed for 15 min with the running buffer. Data were analyzed with BIAevaluation 4.1 software. Binding profiles and calculated $K_D$s are shown in FIG. 15 and Table 8. From the SPR profiles (FIG. 15), it can be seen that the anti-human lysozyme $V_L$s indeed bind to their target antigen, lysozyme, confirming the binding results obtained by phage ELISA. The calculated binding affinities ($K_D$s) are diverse, with a good number of them having high affinities ($K_D$=0.05 μM-0.2 (μM).

Figure 17:
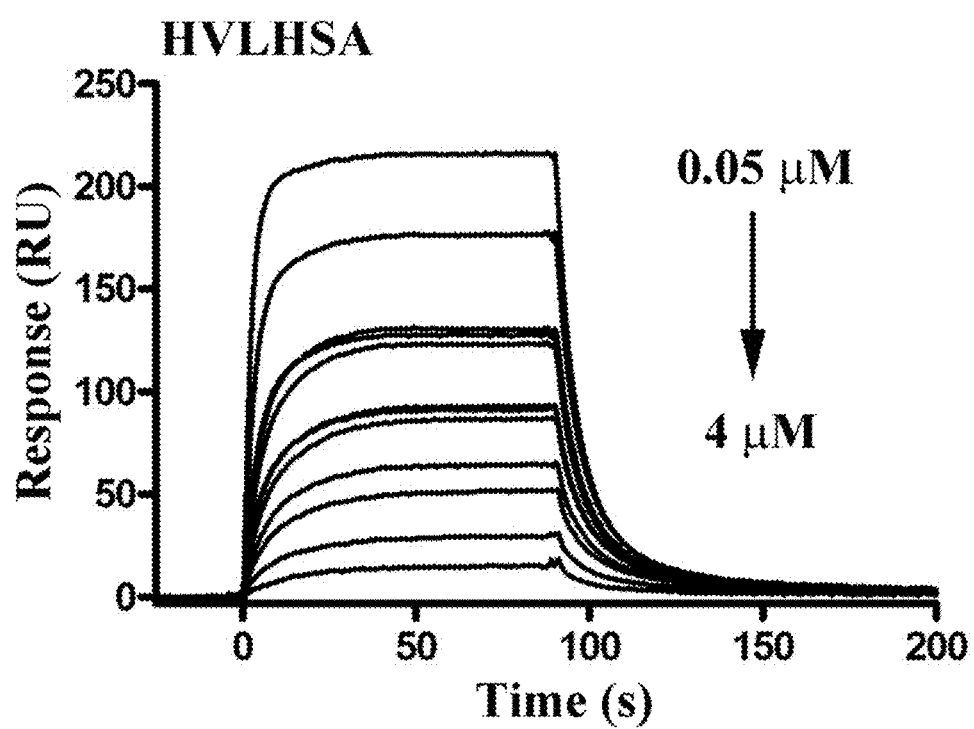
FIG. 17 shows a SPR analysis of anti-human serum albumin $V_L$. Biacore sensorgram showing the binding of anti-human serum albumin $V_L$ to immobilized human serum albumin at diverse range of concentrations indicated on the sensorgram: 0.05, 0.1, 0.2, 0.3, 0.4, 0.5, 0.5, 0.75, 1, 1, 2, and 4 µM.

The $K_D$ of the $V_L$ against human serum albumin was determined by surface plasmon resonance as described for other domains above. Briefly, the binding of the $V_L$ to immobilized human serum albumin was determined by SPR using the BIACORE 3000 (GE Healthcare). Approximately 1,600 RUs of human serum albumin, 1,900 RUs of bovine serum albumin and 2,200 RUs of ovalbumin were immobilized on a research grade CM5 sensor chip. An ethanolamine blocked surface was prepared, as a reference, in exactly the same manner as the protein surfaces. Immobilizations were carried out at concentrations of 20 μg/mL in 10 mM acetate buffer pH 4.5 using the amine coupling kit supplied by the manufacturer. The $V_L$ was passed through a Superdex 75 column (GE Healthcare) to eliminate any possible aggregates prior to Biacore analysis. For the binding studies, analyses were carried out at 25° C. in 10 mM HEPES, pH 7.4 containing 150 mM NaCl, 3 mM EDTA and 0.005% surfactant P20. The flow rates used were 40 μL/min and sample volumes were 60 μL. For regeneration the surface was washed for 10 min with the running buffer. Data were analyzed with BIAevaluation 4.1 software. FIG. 17 clearly shows that the $V_L$ binds to its target antigen, human serum albumin. The calculated $K_D$ was determined to be 0.8 μM (Table 8). The binding was specific as the $V_L$ did not bind to ovalbumin or to bovine serum albumin.

Thus the results show that $V_H$ and $V_L$ domains with non-canonical disulfide bonds are feasible as scaffolds for constructing $V_H$/$V_L$ synthetic libraries that are sources of antigen binders with high affinity, stability (non-aggregation and thermostability), and expression yields.

Example 10: Construction of a Disulfide-Stabilized $V_H$ Phage Display Library

Experiments were designed to create a $V_H$ phage display library with randomized CDRs built on a $V_H$ scaffold stabilized by extra disulfide linkage at positions 49 and 69. To construct the library, a $V_H$ phage display library (HVHP430LGH3) was used as a template to introduce additional disulfide linkage by replacing two selected amino acid residues (49Ser and 69Ile) with cysteines using the method described above for the $V_L$ library and previously (Sidhu et al., 2000; Hussak et al (c)). The HVHP430LGH3phage display library is a phagemid vector-based library with the CDR-randomized human $V_H$ genes cloned into the phagemid pMED-1 and fused with protein 3 gene. ("Non-aggregating human $V_H$ domains" PCT publication WO2009/079093).

The procedure to construct the disulfide-stabilized $V_H$ phage display library was performed essentially as described above and in Hussack et al (c) and Sidhu et al., 2000). Briefly, the construction was done by two separate rounds of site-directed mutagenesis on the two amino acid residues selected to be replaced with cysteines. Firstly, dU-ssDNA (uridine-containing single strand phage DNA) was prepared using E. coli CJ236 infected with phage ($4 \times 10^{12}$ cfu (colony-forming unit)) from HVHP430LGH3 library. After confirming the incorporation of uridine into the dU-ssDNA by determining titers against E. coli TG1 and CJ236 as described above and in Hussack et al (c), a series of in vitro DNA synthesis reaction including phosphorylation of the primer IT', for annealing to mutagenize 49Ser to 49Cys, ligation, and polymerization was subsequently performed using 20 μg of the dU-ssDNA. The in vitro DNA synthesis reaction resulted in 23 μg of heteroduplex DNA in total. Subsequent 10 separate transformations using 50 μL of E. coli TG1 competent cells with 564 ng of the heteroduplex DNA for each transformation gave the diversity of $1.1 \times 10^{10}$ cfu in total. Clonal selections by PCR with primers (M13RPa or b and −96GIII) revealed that about 50% (8 out of 16) of the clones had the 49Ser to 49Cys mutation. For the next round of mutagenesis, phage was prepared from the 49Ser to 49Cys mutated phagemid library ((HVHP430LGH3C1)) by rescuing them with M13K07 helper phage, resulting in the phage titer of $2.1 \times 10^{13}$ cfu/mL.

dU-ssDNA was subsequently prepared from *E. coli* CJ236 using the phage ($4 \times 10^{12}$ cfu) from (HVHP430LGH3C1) which was followed by in vitro DNA synthesis reaction with 8 µg of the dU-ssDNA and the primer KT125 annealing to mutagenize another amino acid residue (69Ile to 69Cys), resulting in 12 µg of heteroduplex DNA in total. Subsequent 22 separate transformations using 50 µL of *E. coli* TG1 competent cells with 230 ng of the heteroduplex DNA for each transformation gave the library size of $5.3 \times 10^9$ cfu in total. To determine the percentage of the library that represents $V_H$ genes carrying double mutations (49Ser to 49Cys and 69Ile to 69Cys), 65 colonies were screened by PCR with primers (M13RP a or b and −96GIII), sequenced and analyzed, revealing that 28% (18 out of 65) of the clones had double mutations (49Ser to 49Cys and 69Ile to 69Cys), 35% (23 out of 65) had single mutations (49Ser to 49Cys), 15% (10 out of 65) had the single mutation 69Ile to 69Cys, and 22% (14 out of 65) had no mutations. Thus, the size of the library with both Cys mutations (HVHP430LGH3C2) was corrected to $1.5 \times 10^9$ cfu ($=5.3 \times 10^9 \times 28\%$) according to the result of the clonal selection. The HVHP430LGH3C2 phage display library was amplified in 300 mL of 2×YT, the library cells were resuspended in 15 mL of 10% glycerol, and subsequently kept as 1 mL aliquots at −80° C.

The diversity of the library is high ($5.3 \times 10^9$ transformants) with the additional stabilizing 49Ser to 49Cys and 69Ile to 69Cys mutations in all its $V_H$ members. The library should yield binders with high stability to target antigens, due to the presence of Cys49/Cys69 disulfide linkage in its $V_H$ members, using the standard selection and panning techniques known in the art.

Non-Limiting Embodiments of the Invention

Embodiment 1 comprises a composition comprising a immunoglobulin scaffold comprising one or more than one non-canonical disulfide bond in the framework region (FR). Embodiment 1 further comprises a composition comprising a mutant immunoglobulin scaffold comprising one or more than one non-canonical disulfide bond in the framework region (FR), wherein the composition has one or more improvements selected from increased stability, increased melting temperature, increased solubility and decreased aggregation. The improvements of a mutant composition of Embodiment 1 may be selected from improved thermal refolding efficiency, increased resistance to protease digestion, increased shelf life at or above room temperature, at 4° C., or below 0° C. The improvements of a mutant composition of Embodiment 1 may be further characterized as increased or prolonged functionality when administered to a human subject when compared to a corresponding composition that does not comprise the non-canonical disulfide bond.

Embodiment 2 comprises the composition of embodiment 1, wherein the immunoglobulin scaffold is selected from a $V_H$ or a $V_L$ scaffold, wherein the $V_H$ scaffold comprises at least one non-canonical disulfide bond in the FR, wherein the non-canonical disulfide bond is formed between Cys residues introduced at positions 49 and 69, based on Kabat numbering; and the $V_L$ scaffold comprises at least one non-canonical disulfide bond in the FR, wherein the non-canonical disulfide bond is formed between Cys residues introduced at positions 48 and 64, based on Kabat numbering.

Embodiment 3 comprises the composition of embodiment 1 wherein the scaffold is part of a larger antibody protein or fragment selected from the group consisting of a single domain antibody (sdAb), scFv, Fab, F(ab)$_2$, or mature immunoglobulin. Embodiment 4 comprises the composition of embodiment 3 wherein the mature immunoglobulin is selected from the group consisting of an IgG1, IgG2, IgG3, IgG4, IgE, and/or IgM.

Embodiment 5 comprises the composition of embodiment 1 wherein the immunoglobulin scaffold is a $V_H$. Embodiment 5 further comprises the composition of embodiment 1 wherein the immunoglobulin scaffold is selected from the $V_H1$ family, $V_H2$ family or $V_H3$ family. Embodiment 6 comprises the composition of embodiment 5 wherein the $V_H$ is of the $V_H3$ family. In a further embodiment, the $V_H$ immunoglobulin scaffold is selected from one or more sequences of the group consisting of SEQ ID NOS: 2, 4, 6, 8, and 70-83, or a sequence substantially identical thereto. In one embodiment, the substantially identical sequence differs by at least 1, at least 2, at least 3, at least 4 or at least 5 residues compared to the disclosed sequence.

Embodiment 7 comprises the composition of embodiment 1 wherein the immunoglobulin scaffold is a $V_L$. Embodiment 8 comprises the composition of embodiment 7 wherein the $V_L$ is of the kappa or lambda family. In a further embodiment, the $V_L$ immunoglobulin scaffold is selected from one or more sequences of the group consisting of SEQ ID NOS: 10, 12, 14, 16, 18, 20, 22 and 24, or a sequence substantially identical thereto. In one embodiment, the substantially identical sequence differs by at least 1, at least 2, at least 3, at least 4 or at least 5 residues compared to the disclosed sequence.

Embodiment 9 comprises the composition of any one of embodiments 1 to 8, wherein the one or more than one non-canonical disulfide bond is formed between cysteines introduced by mutations into FR2 and FR3. Embodiment 10 comprises the composition of embodiment 5 or 6, wherein the Cys residues are introduced at positions 49 and 69, based on Kabat numbering. Embodiment 11 comprises the composition of embodiment 7 or 8, wherein the Cys residues are introduced at positions 48 and 64, based on Kabat numbering.

Embodiment 12 comprises the composition of any one of embodiments 1 to 11 wherein the scaffolds are multimerized. In one embodiment, the resulting multimer from embodiment 12 comprises at least a dimer, a trimer, tetramer, pentamer, hexamer, heptamer or an octamer.

Embodiment 13 comprises the composition of any one of embodiments 1 to 12 wherein the scaffold is fused to a second sequence, wherein the second sequence is selected from an Fc fragment, a targeting sequence, a signal sequence and a purification tag, or any combination thereof. In one embodiment, at least one unit of the second sequence is fused to at least one monomer comprising the scaffold of the invention In one embodiment, the at least one unit of a second sequence is fused to a composition of embodiment 12.

Embodiment 14 comprises the composition scaffold of any one of embodiments 1 to 13, wherein the immunoglobulin scaffold comprises the framework regions of sequences selected from the group consisting of SEQ ID NOS: 2, 4, 6, 8, 10, 12, 14, 16, 18, 20, 22 and 24 and 70-83, or sequences substantially identical thereto, or fragments thereof, with the proviso that the substantially identical sequences retain both the canonical and non-canonical disulfide bonds and wherein the residues comprising CDR1, CDR2 and CDR3 may be any suitable sequence. In a specific embodiment, the composition comprises SEQ ID NO:2 or a functional fragment thereof. In a specific embodiment, the composition comprises SEQ ID NO:4 or a functional fragment thereof. In a specific embodiment, the composition comprises SEQ ID NO:6 or a functional fragment thereof. In a specific embodiment, the composition comprises SEQ ID NO:8 or a functional fragment thereof. In a specific embodiment, the composition comprises SEQ ID NO:10 or a functional fragment thereof. In a specific embodiment, the composition comprises SEQ ID NO:12 or a functional fragment thereof. In a specific embodiment, the composition comprises SEQ ID NO:14 or a functional fragment thereof. In a specific embodiment, the composition comprises SEQ ID NO:16 or a functional fragment thereof. In a specific embodiment, the composition comprises SEQ ID NO:18 or a functional fragment thereof. In a specific embodiment, the composition comprises SEQ ID NO:20 or a functional fragment thereof. In a specific embodiment, the composition comprises SEQ ID NO:22 or a functional fragment thereof. In a specific embodiment, the composition comprises SEQ ID NO:24 or a functional fragment thereof. In a specific embodiment, the composition comprises SEQ ID NO:70 or a functional fragment thereof. In a specific embodiment, the composition comprises SEQ ID NO:71 or a functional fragment thereof.

In a specific embodiment, the composition comprises SEQ ID NO:72 or a functional fragment thereof. In a specific embodiment, the composition comprises SEQ ID NO:73 or a functional fragment thereof. In a specific embodiment, the composition comprises SEQ ID NO:74 or a functional fragment thereof. In a specific embodiment, the composition comprises SEQ ID NO:75 or a functional fragment thereof. In a specific embodiment, the composition comprises SEQ ID NO:76 or a functional fragment thereof. In a specific embodiment, the composition comprises SEQ ID NO:77 or a functional fragment thereof. In a specific embodiment, the composition comprises SEQ ID NO:78 or a functional fragment thereof. In a specific embodiment, the composition comprises SEQ ID NO:79 or a functional fragment thereof. In a specific embodiment, the composition comprises SEQ ID NO:80 or a functional fragment thereof. In a specific embodiment, the composition comprises SEQ ID NO:81 or a functional fragment thereof. In a specific embodiment, the composition comprises SEQ ID NO:82 or a functional fragment thereof. In a specific embodiment, the composition comprises SEQ ID NO:83 or a functional fragment thereof. In a specific embodiment, the composition comprises SEQ ID NO:84 or a functional fragment thereof.

Embodiment 15 comprises a nucleic acid encoding a composition of any one of embodiments 1 to 14. Embodiment 16 comprises an expression vector comprising the nucleic acid of embodiment 15. Embodiment 17 comprises a host cell or organism comprising the expression vector of embodiment 16. In one embodiment, the nucleic acid sequence encoding the immunoglobulin scaffold of the invention encodes a sequence substantially identical to the disclosed compositions of the invention. In one embodiment, the substantially identical sequence differs by at least 1, at least 2, at least 3, at least 4 or at least 5 residues compared to the disclosed sequence. In one embodiment the nucleic acid is codon optimized for expression in a host cell or organism. In one embodiment the nucleic acid is codon optimized for expression in a bacterium. In one embodiment the nucleic acid is codon optimized for expression in $E.\ coli$. In one embodiment the nucleic acid is codon optimized for expression in yeast. In one embodiment the nucleic acid is codon optimized for expression in a nonhuman animal cell. In one embodiment the nucleic acid is codon optimized for expression in a mammalian cell. In one embodiment the nucleic acid is codon optimized for expression in a human cell.

Embodiment 18 comprises a recombinant library comprising at least one immunoglobulin scaffold of embodiment 2, wherein the immunoglobulin scaffold further comprises a multiplicity of suitable CDR sequences, wherein the multiplicity of CDR sequences provide a diversity of at least $10^5$, at least $10^6$, at least $10^7$, at least $10^8$, at least $10^9$ or more than $10^9$ clones per library.

Embodiment 19 comprises a method of improving stability of a composition comprising an immunoglobulin scaffold, the method comprising introducing one or more than one non-canonical disulfide bond in the framework region. The method of embodiment 19 further comprises the method of using recombinant technology to replace a first codon and a second codon in an immunoglobulin sequence with a codon for cysteine at each position, wherein the immunoglobulin sequence is a $V_H$ scaffold, and wherein the first codon corresponds to position 49 using Kabat numbering and the second codon corresponds to position 69 using Kabat numbering. The method of embodiment 19 further comprises the method of using recombinant technology to replace a first codon and a second codon in an immunoglobulin sequence with a codon for cysteine at each position, wherein the immunoglobulin sequence is a $V_L$ scaffold, and wherein the first codon corresponds to position 48 using Kabat numbering and the second codon corresponds to position 64 using Kabat numbering. The invention further comprises use of the method of embodiment 19 for creation of an expression library. In one embodiment, the library is the library of embodiment 18.

Embodiment 20 comprises the method of making a mutant composition comprising an immunoglobulin scaffold having one or more improvements selected from increased stability, increased melting temperature, increased solubility and decreased aggregation, wherein the method is the method of embodiment 19. The improvements of a mutant composition of Embodiment 20 may be selected from improved thermal refolding efficiency, increased resistance to protease digestion, increased shelf life at or above room temperature, at 4° C., or below 0° C. The improvements of a mutant composition of Embodiment 20 may be further characterized as increased or prolonged functionality when administered to a human subject when compared to a corresponding composition that does not comprise the non-canonical disulfide bond.

Embodiment 21 comprises any one or more compositions of any one or more of embodiments 1 through 14, wherein the composition is a therapeutic agent. The invention further comprises the composition of embodiment 21 in a pharmaceutically acceptable carrier or excipient therefor.

Embodiment 22 comprises the use of a composition of embodiment 21, wherein the composition is administered to a subject in need thereof. Embodiment 23 comprises the use of any one or more compositions of embodiment 21 in a medicament to be administered to a subject in need of treatment.

Embodiment 24 comprises any one or more compositions of any one or more of embodiments 1 through 14, wherein the composition comprising the immunoglobulin scaffold is derived from a non-human animal. In one embodiment, the non-human animal includes all vertebrates, especially vertebrates selected from avians, amphibians, reptiles, mammals, camelids, chicken, rat, mouse, rabbit, goat, sheep, cow, cat, dog, horse, or nonhuman primates. In one embodiment the immunoglobulin scaffold is human. In one embodiment the immunoglobulin scaffold is camelid. In one embodiment, the camelid species is selected from the group consisting of llama, alpaca and camel. In one embodiment, the camelid scaffold is derived from any one or more of a $V_H$ region, a $V_L$ or a $V_H H$ region.

| Clone Name | Sequence | SEQ ID NO |
|---|---|---|
| HVHAm302 | QVQLVESGGGLIKPGGSLRLSCAASGDTVSDESMTWVRQAPGKGLEW VSAISSSGGSTYYADSVKGRFTISRDNSKNTVYLQMNSLRAEDTAVY YCVTDNRSCQTSLCTSTTRSWGQGTMVTVSS | 1 |
| HVHAm302S | QVQLVESGGGLIKPGGSLRLSCAASGDTVSDESMTWVRQAPGKGLEW VCAISSSGGSTYYADSVKGRFTCSRDNSKNTVLYQMNSLRAEDTA VYYCVTDNRSCQTSLCTSTTRSWGQGTMVTVSS | 2 |
| HVHAm427 | QVQLVESGGGLIKPGGSLRLSCAASGVTLSPECMAWVRQAPGKGLEW VSAISSSGGSTYYADSVKGRFTISRDNSKNTVYLQMNSLRAEDTAVY YCVSCEGENAFWGQGTMVTVSS | 3 |
| HVHAm427S | QVQLVESGGGLIKPGGSLRLSCAASGVTLSPECMAWVRQAPGKLGEW VCAISSSGGSTYYADSVKGRFTCSRDNSKNTVYLQMNSLRAEDTA VYYCVSCEGENAFWGQGTMVTVSS | 4; |
| HVHAm431: | QVQLVESGGGLIKPGGSLRLSCAASGYTVSSECMGWVRQAPGKGLEW VSAISSSGGSTYYADSVKGRFTISRDNSKNTVYLQMNSLRAEDTAVY YCVRDSKNCHDKDCTRPYCSWGQGTMVTVSS | 5 |
| HVHAm431S | QVQLVESGGGLIKPGGSLRLSCAASGYTVSSECMGWVRQAPGKGLEW VCAISSSGGSTYYADSVKGRFTCSRDNSKNTVYLQMNSLRAEDTA VYYCVRDSKNCHDKDCTRPYCSWGQGTMVTVSS | 6 |
| HVHPC235 | QVQLVESGGGLIKPGGSLRLSCAASGFSVISESMTWVRQAPGKGLEW VSAISSSGGSTYYADSVKGRFTISRDNSKNTVHLQMNSLRADDTAVY YCAAKKIDGARYDYWGQGTMVTVSS | 7 |
| HVHPC235S | QVQLVESGGGLIKPGGSLRLSCAASGFSVISESMTWVRQAPGKGLEW VCAISSSGGSTYYADSVKGRFTCSRDNSKNTVHLQMNSLRAEDTA VYYCAAKKIDGARYDYWGQGTMVTVSS | 8 |
| HVLP324 | DIQMTQSPSSLSASVGDRVTITCRASQSISTYLNWYQQKPGKAPKLL IFAASTLQSGVPSRFSGSGSGTDFTLTISNLQPEDFATYYCQQSYST PRTFGHGTKVTVL | 9 |
| HVLP324S | DIQMTQSPSSLSASVGDRVTITCRASQSISTYLNWYQQKPGKAPKLL CFAASTLQSGVPSRFSCSGSGTDFTLTISNLQPEDFATYYCQQSY STPRTFGHGTKVTVL | 10 |
| HVLP325 | EIVLTQSPTTLSLSPGERATLSCRASQSVGRYLAWYQQRPGQAPRLL VFDTSNRAPGVPARFSGRGSGTLFTLTISSLEPEDSAVYFCQQRSSG LTFGGGTKVTVL | 11 |
| HVLP325S | EIVLTQSPTTLSLSPGERATLSCRASQSVGRYLAWYQQRPGQAPRLL CFDTSNRAPGVPARFSCRGSGTLFTLTISSLEPEDSAVYFCQQRS SGLTFGGGTKVTVL | 12 |
| HVLP335 | EIVMTQSPATLSLSPGERATLSCRASQSVSSSLAWYQQKPGQAPRL LIYGTSNRATGIPDRFSGSGSGTHFTLTINRLEPGDFAVYYCQQYGS SPRTFGQGTKVEIK | 13 |
| HVLP335S | EIVMTQSPATLSLSPGERATLSCRASQSVSSSLAWYQQKPGQAPRL ICYGTSNRATGIPDRFSCSGSGTHFTLTINRLEPGDFAVYYCQQY GSSPRTFGQGTKVEIK | 14 |
| HVLP342 | DIQMTQSPSSLSASVGDRVTITCRASQDIRTDLDWFQQRPGRAPHRL IYGASSLQGGVPSRFSGSGSGTEFTLTISGLQPEDFATYYCLQHHTY PRTFGLGTKVTVL | 15 |
| HVLP342S | DIQMTQSPSSLSASVGDRVTITCRASQDIRTDLDWFQQRPGRAPHRL CYGASSLQGGVPSRFSCSGSGTEFTLTISGLQPEDFATYYCLQHH TYPRTFGLGTKVTVL | 16 |
| HVLP351 | EIVMTQSPVTLSLSPGERATLSCRASQSVGTSLAWYQQKPGQAPRLL IYDASNRATGISARFSGSGSGTDFTLTISSLEPEDFAVYYCQQRYNW PRTFGGGTKVTVL | 17 |
| HVLP351S | EIVMTQSPVTLSLSPGERATLSCRASQSVGTSLAWYQQKPGQAPRLL CYDASNRATGISARFSCSGSGTDFTLTISSLEPEDFAVYYCQQRY NWPRTFGGGTKVTVL | 18 |
| HVLP364 | ETTLTQSPATLSVSPGERATFSCRASQSVSNNLAWYQQKPGQAPRLL IYGASSRTTGIPDRFSASGSGTDFTLTISRLEPEDFAVYYCQQYDTS PRTFGQGTKVEIK | 19 |

| Clone Name | Sequence | SEQ ID NO |
|---|---|---|
| HVLP364S | ETTLTQSPATLSVSPGERATFSCRASQSVSNNLAWYQQKPGQAPRLL CYGASSRTTGIPDRFSCSGSGTDFTLTISRLEPEDFAVYYCQQYD TSPRTFGQGTKVEIK | 20 |
| HVLP389 | QSVVTQPPSVSAAPGQRVTISCSGSSYNIGENSVSWYQQLPGTAPKL LIYGNDKRPSGIPDRFSGSKSGTSATLGITGLQTGDEADYYCGTWDS NLRASVFGGGTKVTVL | 21 |
| HVLP389S | QSVVTQPPSVSAAPGQRVTISCSGSSYNIGENSVSWYQQLPGTAPKL ICYGNDKRPSGIPDRFSCSKSGTSATLGITGLQTGDEADYYCGTW DSNLRASVFGGGTKVTVL | 22 |
| HVLP3103 | ETTLTQSPGTLSLSPGERATLSCRASQSVRNNLAWYQQRPGQAPRLL IYGASTRATGIPARFSGSGSGTDFTLTISSLQVEDVAVYYCQQYTT PKTFGQGTKVEIK | 23 |
| HVLP3103S | ETTLTQSPGTLSLSPGERATLSCRASQSVRNNLAWYQQRPGQAPRLL CYGASTRATGIPARFSCSGSGTDFTLTISSLQVEDVAVYYCQQYY TTPKTFGQGTKVEIK | 24 |
| None | SCQTSLCTSTTR | 25 |
|  | LSCAASGDTVSDESMTWVR | 26 |
|  | AEDTAVYYCVTDNR | 27 |
|  | SCQTSLCTSTTR | 28 |
|  | GLEWVCAISSSGGSTYYADSVK | 29 |
|  | FTCSR | 30 |
|  | LSCAASGDTVSDESMTWVR | 31 |
|  | AEDTAVYYCVTDNR | 32 |
|  | GLEWVCAISSSGGSTYYADSVK | 33 |
|  | FTCSR | 34 |
|  | LSCAASGFSVISESMTWVR | 35 |
|  | AEDTAVYYCAAK | 36 |
| M13RPa | 5'-TCACACAGGAAACAGCTATGAC-3' | 37 |
| KT131 | 5'-ACCACTACTACTAATAGCGCAGACCCACTCCAGCCCCTTC-3' | 38 |
| M13FP | 5'-CGCCAGGGTTTTCCCAGTC ACGAC-3' | 39 |
| K1129 | 5'-GCAGACTCCGTGAAGGGCCGATTCACCTGCTCCAGAGACAAT TCCAAGAAC-3' | 40 |
| KT130 | 5'-TGCGCTATTAGTAGTAGTGGTGGTAGCACATACTACGCAGAC TCCGTGA AGGGCCG-3' | 41 |
|  | VTITCR | 42 |
|  | LLCFASTLQSGVPSR | 43 |
|  | FSCSGSGTDFTLTISNQPEDFATYYCQQSYSTPR | 44 |
|  | ATLSCR | 45 |
|  | GSGTLFTLTISSLEPEDSAVYFCQQR | 46 |
|  | LLCFDTSNR | 47 |
|  | FSCR | 48 |
|  | LLCYGTSNR | 49 |
|  | FSCSGSGTHFTLTIVR | 50 |
|  | ATLSCR | 51 |

SEQUENCES

| Clone Name | Sequence | SEQ ID NO |
|---|---|---|
| | LEPGDFAVYYCQQYGSSPR | 52 |
| | VTITCR | 53 |
| | LCYGASSLQGGVPSR | 54 |
| | FSCSGSGTEFTLTISGLQPEDFATYYCLQHHTYPR | 55 |
| | ATLSCR | 56 |
| | LLCYDASNR | 57 |
| | FSCSGSGTDFTLTISSLEPEDFAVYYCQQR | 58 |
| | LLCYGASSRTR | 59 |
| | FSCSGSGTDFTLTISR | 60 |
| | ATFSCR | 61 |
| | LEPEDFAVYYCQQYDTSPR | 62 |
| | LLCYGNDK | 63 |
| | FSCSK | 64 |
| | VTISCGSSYNIGENSVSWYQQLPGTAPK | 65 |
| | SGTSATLGITGLQTGDEADYYCGTWDSNLR | 66 |
| | ATLSCR | 67 |
| | LLCYGASTR | 68 |
| | FSCSGSGTDFTLTISSLQVEDVAVYYCQQYYTTPK | 69 |
| HVHP44S | EVQLVESGGGLVQPGGSLRLSCAASGFTFSSYAMSWVRQAPGKGLEWVCAISGSGGSTYYADSVKGRFTCSRDNSKNTLYLQMNSLRAEDTAVYYCAKDEPRSVSGLRGVVDSWGRGTLVTVSS | 70 |
| HVHB82S | QVQLQESGGGLVQPGGSLRLSCAASGFTFSSYAMSWVRQAPGKGLEWVCAISGSGGSTYYADSVKGRFTCSRDNSKNTLYLQMNSLRAEDTAVYYCGTDMEVWGKGTTVTVSS | 71 |
| HVHP421S | QLQLQESGGGVVQPGRSLRLSCAASGFTFSSYAMSWVRQAPGKGLEWVCAISGSGGSTYYADSVKGRFTCSRDNSKNTLYLQMNSLRAEDTAVYYCAKDGKGGSSGYDHPDYWGQGTLVTVSS | 72 |
| HVHP419S | QLQLQESGGGLVQPGGSLRLSCAASGFTFSSYAMSWVRQAPGKGLEWVCAISGSGGSTYYADSVKGRFTCSRDNSKNSLYLQMNSLGAEDTAVYYCARSWSGSSYGGDLDSWGQGTLVTVSS | 73 |
| HVHP430S | QVQLVESGGGLIKPGGSLRLSCAASGFTFSNYAMSWVRQAPGKGLEWVCAISSSGGSTYYADSVKGRFTCSRDNSKNTVYLQMNSLRAEDTAVYYCVREEYRCSGTSCPGAFDIWGQGTMVTVSS | 74 |
| HVHP429S | EVQLVESGGTLVQPGGSLRLSCAASGFTFINYAMSWVRQAPDKGLDWVCTISNNGGATYYADSVKGRFTCSRDNSNNTLYLQMNSLRPDDTAVYYCAKGPINTGRYGDWGQGTLVTVSS | 75 |
| HVHM41S | QVQLVQSGGGLVQPGRSLRLSCAASGFAFSSYAMSWVRQAPGKGLEWVCAISGGGDHTYYADSVKGRFTCSRDNSKNTLYLQMNSLRAEDTAVYYCAKEGMVRGVSSAPFDYWGQGTLVTVSS | 76 |
| HVHM81S | EVQLVQSGGGLVQPGRSLRLSCAASGFTFDDYAMHWVRQAPGKGLEWVCGISGSGASTYYADSVKGRFTCSRDNSKNTLYLQMNSLRAGDTALYYCARQSITGPTGAFDVWGQGTMVTVSS | 77 |
| HVHP428S | QLQLQESGGGLVQPGGSLRLSCAASGFTFSSYAMSWFRQAPGKGLEWVCFIRSKAYGGTTEYAASVKGRFTCSRDDSKSIAYLQMNSLRAEDTAMYYCARRAKDGYNSPEDYWGQGTLVTVSS | 78 |

SEQUENCES

| Clone Name | Sequence | SEQ ID NO |
|---|---|---|
| HVHP420S | QVQLVESGGGLVKPGGSLRLSCAASGFTFSNAWMTWVRQAPGKGLEW<br>VCRIKTKTDGGTTDYAAPVKGRFTCSRDDSKNTLYLQMNSLKTED<br>TAVYYCTTDRDHSSGSWGQGTLVTSS | 79 |
| HVHP414S | DVQLVQSGGGLVKPGGSLRLSCTASGFPFSNAWMSWVRQAPGKGLEW<br>VCRITSKTDGGTTDYVAPVKGRFTCSRDDSKNTLYLQMNSLKTED<br>TAVYYCTTDQANAFDIWGQGTMVTSS | 80 |
| HVHP423S | QMQLVQSGGGVVQPGGSLRLSCAASGFTVSSSRMSWFRQAPGMGLEW<br>VCVIYSGGSTYYADSVRGRFCSRDNSKNTLYLQMNSLRAEDTAL<br>YYCAREREGAVTREDWGQGTLVTSS | 81 |
| HVHP413S | QVQLVQSGGGLVKPGGSLRLSCAASGFTFSDYYMSWVRQAPGKGLEW<br>VCFIYSGGSTYYADSVKGRFTCSRDNSKNTLYLQMNSLRAEDTAV<br>YYCARESRVGGGAFDIWGQGTMVTSS | 82 |
| HVHP426S | QVQLVQSGGGVVQPGRSLRLSCAASGFIVDGYAMHWVRQAPGQGLEW<br>VCVTNNGGSTSYADSVKGRFTCSRDNSKNTVYLQMNSLRAEDTAV<br>YYCARQSITGPTGAFDIWGQGTMVTSS | 83 |
| | QAPGQGVEWVCVTNNGGSTSADSVK | 84 |
| | FTCSR | 85 |
| | GSGSKAAA | 86 |
| V$_L$24-CDR1 | AGA GTC ACC ATC ACT TGC NNK GCA AGT CAG RGC ATT NNK NNK NNK TTA NNK TGG TAT CAG CAG AAA CCA | 87 |
| V$_L$24S-CDR2 | CCT AAA CTC CTG TGC TTT NNK GCA TCC NNK CKN NNK AGT GGG GTC CCA TCA AGG | 88 |
| V$_L$24-CDR3 | TTT GCA ACT TAC TAC TGT NNK CAG NNK NNK NNK NNK CCT NNK ACG TTC GGC CAC GGGACC | 89 |
| V$_L$24-CDR3a | TTT GCA ACT TAC TAC TGT NNK CAG NNK NNK NNK NNK CCT NNK NNK ACG TTC GGC CAC GGG ACC | 90 |
| V$_L$24-CDR3b | TTT GCA ACT TAC TAC TGT NNK CAG NNK NNK NNK NNK CCT NNK NNK NNK ACGTTC GGC CAC GGGACC | 91 |
| -96GIII | CCC TCA TAG TTA GCG TAA CGA TCT | 92 |
| fdTGIII | GTG AAA AAA TTA TTA TTC GCA ATT CCT | 93 |
| HV$_L$24-BamHI | TTG TTC GGA TCC TAG GAC GGT CAC CT | 94 |
| HVL24-Bbs1 | TAT GAA GAC ACC AGG CCG ACA TCC AG | 95 |
| KT124 | TGT GCT ACC ACC ACT ACT AAT AGC GCA GAC CCA CTC CAG CCC CTT CCC TGG | 96 |
| KT125 | CAC GGT GTT CTT GGA ATT GTC TCT GGA GCA GGT GAA TCG GCC CTT CAC GGA GTC | 97 |
| M13RPb | CAG GAA ACA GCT ATG AC | 98 |
| HVLHLNN | DIQMTQSPSSLSASVGDRVTITCSASQSINNRLYWYQQKPGKAPKLL<br>CFPASFLFSGVPSRFSCSGSGTDFTLTISNLQPEDFATYYCQQSY<br>STPRTFGHGTKVTVL | 99 |
| HVLHLDS | DIQMTQSPSSLSASVGDRVTITCTVSQGIDSRLYWYQQKPGKAPKLL<br>CFPASLLESGVPSRFSCSGSGTDFILTISNLQPEDFATYYCQQSY<br>STPRTFGHGTKVTVL | 100 |
| HVLHLRN | DIQMTQSPSSLSASVGDRVTITCKASQGIRNRLYWYQQKPGKAPKLL<br>CFPASILDSGVPSRFSCSGSGTDFTLTISNLQPEDFATYYCAQQP<br>GLPNSRTFGHGTKVTVL | 101 |
| HVLHLNE | DIQMTQSPSSLSASVGDRVTITCDASQSINERLYWYQQKPGKAPKLL<br>CFPASILTSGVPSRFSCSGSGTDFTLTISNLQPEDFATYYCRQPR<br>SGPSTFGHGTKVTVL | 102 |

| Clone Name | Sequence | SEQ ID NO |
|---|---|---|
| HVLHLAQ | DIQMTQSPSSLSASVGDRVTITCGASQSIAQRLYWYQQKPGKAPKLL CFPASLLHSGVPSRFSCSGSGTDFTLTISNLQPEDFATYYCAQRA SPPRPTFGHGTKVTVL | 103 |
| HVLHLEM | DIQMTQSPSSLSASVGDRVTITCQASQGIEMFLQWYQQKPGKAPKLL CFAASTLQSGVPSRFSCSGSGTDFTLTISNLQPEDFATYYCVQPG VAPPPGTFGHGTKVTVL | 104 |
| HVLHLQI | DIQMTQSPSSLSASVGDRVTITCRASQSIQIMLDWYQQKPGKAPKLL CFGASFLISGVPSRFSCSGSGTDFTLTISNLQPEDFATYYCRQTW TPPAPTFGHGTKVTVL | 105 |
| HVLHLYS | DIQMTQSPSSLSASVGDRVTITCQASQSIYSKLYWYQQKPGKAPKLL CFPASLLWSGVPSRFSCSGSGTDFTLTISNLQPEDFATYYCLQNA ADPHRTFGHGTKVRL | 106 |
| HVLHSA1 | DIQMTQSPSSLSASVGDRVTITCRASQSISTYLNWYQQKPGKAPKLL CFGASRLNSGVPSRFSCSGSGTDFTLTISNLQPEDFATYYCRQLF PLPDRRTFGHGTKVTVL | 107 |
| HVLHLFL | DIQMTQSPSSLSASVGDRVTITCLASQSIFLYLDWYQQKPGKAPKLL CFFASTLESGVPSRFSCSGSGTDFTLTISNLQPEDFATYYCQQSY STPRTFGHGTKVTVL | 108 |

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein and throughout the application are hereby incorporated by reference.

Amzel, L. M., and Poljak, R. J. (1979) Three-dimensional structure of immunoglobulins. Annu. Rev. Biochem. 48, 961-997.

Arbabi-Ghahroudi, M., MacKenzie, R., and Tanha, J. (2009a) Selection of non-aggregating $V_H$ binders from synthetic $V_H$ phage-display libraries. Methods Mol. Biol. 525, 187-216.

Arbabi-Ghahroudi, M., To, R., Gaudette, N., Hirama, T., Ding, W., MacKenzie, R., and Tanha, J. (2009b) Aggregation-resistant $V_H$s selected by in vitro evolution tend to have disulfide-bonded loops and acidic isoelectric points. Protein Eng. Des. Sel. 22, 59-66.

Arbabi-Ghahroudi, M., MacKenzie, R., and Tanha, J. (2010) Site-directed mutagenesis for improving biophysical properties of $V_H$ domains. Methods Mol. Biol. 634, 309-330.

Bell, A., Wang, Z. J., Arbabi-Ghahroudi, M., Chang, T. A., Durocher, Y., Trojahn, U., Baardsnes, J., Jaramillo, M. L., Li, S., Baral, T. N., O'Connor-McCourt, M., Mackenzie, R., and Zhang, J. (2010) Differential tumor-targeting abilities of three single-domain antibody formats. Cancer Lett. 289, 81-90.

Betz, S. F. (1993) Disulfide bonds and the stability of globular proteins. Protein Sci. 2, 1551-1558.

Bloom, J. D., Labthavikul, S. T., Otey, C. R., and Arnold, F. H. (2006) Protein stability promotes evolvability. Proc. Natl. Acad. Sci. USA. 103, 5869-5874.

Chothia, C., and Lesk, A. M. (1987) Canonical structures for the hypervariable regions of immunoglobulins. J. Mol. Biol. 196, 901-917.

Davies, J., and Riechmann, L. (1994) 'Camelising' human antibody fragments: NMR studies on $V_H$ domains. FEBS Lett. 339, 285-290.

Davies, J., and Riechmann, L. (1995) Antibody $V_H$ domains as small recognition units. Biotechnology N. Y. 13, 475-479.

Davies, J., and Riechmann, L. (1996a) Single antibody domains as small recognition units: design and in vitro antigen selection of camelized, human $V_H$ domains with improved protein stability. Protein Eng. 9, 531-537.

Davies, J., and Riechmann, L. (1996b) Affinity improvement of single antibody $V_H$ domains: residues in all three hypervariable regions affect antigen binding. Immunotechnology 2, 169-179.

de Kruif, J., and Logtenberg, T. (1996) Leucine zipper dimerized bivalent and bispecific scFv antibodies from a semi-synthetic antibody phage display library. J. Biol. Chem. 271, 7630-7634.

Eisenberg, D., Schwarz, E., Komaromy M., and Wall R. (1984) Analysis of membrane and surface protein sequences with the hydrophobic moment plot. J. Mol. Biol. 179, 125-142.

Greenfield, N. J. (2006a) Using circular dichroism spectra to estimate protein secondary structure. Nat. Protoc. 1, 2876-2890.

Greenfield, N. J. (2006b) Analysis of the kinetics of folding of proteins and peptides using circular dichroism. Nat. Protoc. 1, 2891-2899.

Harrison, J. L., Williams, S. C., Winter, G., and Nissim, A. (1996) Screening of phage antibody libraries. Methods Enzymol. 267, 83-109.

Ho, S. N., Hunt, H. D., Horton, R. M., Pullen, J. K., and Pease, L. R. (1989) Site-directed mutagenesis by overlap extension using the polymerase chain reaction. Gene 77, 51-59.

Holliger, P., and Hudson, P. J. (2005) Engineered antibody fragments and the rise of single domains. Nat. Biotechnol. 23, 1126-1136.

Hoogenboom, H. R. (2005) Selecting and screening recombinant antibody libraries. Nat. Biotechnol. 23, 1105-1116.

Holt, L. J., Herring, C., Jespers, L. S., Woolven, B. P., and Tomlinson, I. M. (2003) Domain antibodies: proteins for therapy. Trends Biotechnol. 21, 484-490.

Horwich, A. (2002) Protein aggregation in disease: a role for folding intermediates forming specific multimeric interactions. J. Clin. Invest. 110, 1221-1232.

Hurle, M. R., Helms, L. R., Li, L., Chan, W. and Wetzel, R. (1994) A role of destabilizing amino acid replacements in light-chain amyloidosis. Proc. Natl. Acad. Sci. USA. 91, 5446-5450.

Hussack, G., Arbabi-Ghahroudi, M., MacKenzie, C. R., and Tanha, J. Isolation and Characterization of *Clostridium difficile* toxin-specific single-domain antibodies. Methods Mol. Biol. In press (a).

Hussack, G., MacKenzie, C. R., and Tanha, J. Functional characterization of single-domain antibodies with an engineered disulfide bond. Methods Mol. Biol. In press (b).

Hussack, G., Keklikian, A., Alsughayyir, J., Hanifi-Moghadam, P., Arbabi-Ghahroudi, M., van Faassen, H., Hou, S. T., Sad, S., MacKenzie, R., and Tanha, J. A VL single-domain antibody library yields a high-propensity of non-aggregating binders. Protein Eng. Des. Sel. In press (c).

Hussack, G., Hirama, T., Ding, W., MacKenzie, R. & Tanha, J. (2011). Engineered single-domain antibodies with high protease resistance and thermal stability. PLoS ONE, 6, e28218.

Iqbal, U., Trojahn, U., Albaghdadi, H., Zhang, J., O'Connor-McCourt, M., Stanimirovic, D., Tomanek, B., Sutherland, G., and Abulrob, A. (2010) Kinetic analysis of novel mono- and multivalent VHH-fragments and their application for molecular imaging of brain tumours. Br. J. Pharmacol. 160, 1016-1028.

Jespers, L., Schon, O., Famm, K., and Winter, G. (2004) Aggregation-resistant domain antibodies selected on phage by heat denaturation. Nat. Biotechnol. 22, 1161-1165.

Kabat, E. A., Wu, T. T., Perry, H. M, Gottesman, K. S., and Koeler, C. (ed.) (1991) *Sequences of Proteins of Immunological Interest*. US Department of Health and Human Services, US Public Health Service, Bethesda, Md.

Kazlauskas, R. J., and Bornscheuer, U. T. (2009) Finding better protein engineering strategies. Nat. Chem. Biol. 5, 526-529.

Kim, D. Y, and Tanha, J. (2010) Sodium dodecyl sulfate-polyacrylamide gel electrophoresis for screening nonaggregating human antibody heavy chain variable domains. Anal. Biochem. 403, 117-119.

Kim, D. Y. Ding, W., and Tanha, J. Solubility and stability engineering of human $V_H$ domains. Methods Mol. Biol. In press.

Kim, D. Y., Ding, W., Hirama, T., Ryan, R., MacKenzie, R., and Tanha, J. Disulfide linkage engineering for improving biophysical properties of $V_H$ domains. J. Mol. Biol. Submitted.

Kunkel, T. A., Roberts, J. D, and Zakour, R. A. (1987) Rapid and efficient site-specific mutagenesis without phenotypic selection. Methods Enzymol. 154, 367-382.

Lee, C. M., Iorno, N., Sierro, F., and Christ, D. (2007) Selection of human antibody fragments by phage display. Nat. Protoc. 2, 3001-3008.

Lithwick G, Margalit H (2003) Hierarchy of sequence-dependent features associated with prokaryotic translation. Genome Research 13: 2665-73.

Merritt, E. A., and Hol, W. G. (1995) $AB_5$ toxins. Curr. Opin. Struct. Biol. 5, 165-171.

Mitraki, A., and King, J. (1992) Amino acid substitutions influencing intracellular protein folding pathways. FEBS Lett. 307, 20-25.

Nielsen, U. B., Adams, G. P., Weiner, L. M., and Marks, J. D. (2000) Targeting of bivalent anti-ErbB2 diabody antibody fragments to tumor cells is independent of the intrinsic antibody affinity. Cancer Res. 60, 6434-6440.

Porath, J., and Flodin, P. (1959) Gel filtration: a method for desalting and group separation. Nature 183, 1657-1659.

Riechmann, L., and Davies, J. (1995) Backbone assignment, secondary structure and protein A binding of an isolated, human antibody VH domain. J. Biomol. NMR. 6, 141-152.

Ridgway, J. B., Presta, L. G., and Carter, P. (1996) 'Knobs-into-holes' engineering of antibody CH3 domains for heavy chain heterodimerization. Protein Eng. 9, 617-621.

Sambrook, J., Fritsch, E. F., and Maniatis, T. (ed.) (1989) Molecular Cloning: A laboratory Manual. Cold Spring Harbor Laboratory, Cold Spring Harbor, N.Y.

Sidhu, S. S., Lowman, H. B., Cunningham, B. C., and Wells, J. A. (2000) Phage display for selection of novel binding peptides. Methods Enzymol. 328, 333-63.

Starovasnik, M. A., O'Connell, M. P., Fairbrother, W. J., and Kelley, R. F. (1999) Antibody variable region binding by Staphylococcal protein A: thermodynamic analysis and location of the Fv binding site on E-domain. Protein Sci. 8, 1423-1431.

Tanha, J., Nguyen, T. D., Ng, A., Ryan, S., Ni, F., and Mackenzie, R. (2006) Improving solubility and refolding efficiency of human $V_H$s by a novel mutational approach. Protein Eng. Des. Sel. 19, 503-509.

Tanha, J., Xu, P., Chen, Z., Ni, F., Kaplan, H., Narang, S. A. and MacKenzie, C. R. (2001) Optimal design features of camelized human single-domain antibody libraries. J. Biol. Chem. 276, 24774-24780.

To, R., Hirama, T., Arbabi-Ghahroudi, M., MacKenzie, R., Wang, P., Xu, P., Ni, F. and Tanha, J. (2005) Isolation of monomeric human $V_H$s by a phage selection. J. Biol. Chem. 280, 41395-41403.

Ward, E. S., Gussow, D., Griffiths, A. D., Jones, P. T., and Winter, G. (1989) Binding activities of a repertoire of single immunoglobulin variable domains secreted from *Escherichia coli*. Nature 341, 544-546.

Wetzel, R., Perry, L. J., Baase, W. A., and Becktel, W. J. (1988) Disulfide bonds and thermal stability in T4 lysozyme. Proc. Natl. Acad. Sci. USA. 85, 401-405.

Williams, A. F., and Barclay, A. N. (1988) The immunoglobulin superfamily—domains for cell surface recognition. Annu. Rev. Immunol. 6, 381-405.

Worn, A., and Pluckthun, A. (2001) Stability engineering of antibody single-chain Fv fragments. J. Mol. Biol. 305, 989-1010.

Wu, S. L., Jiang, H., Lu, Q. Dai, S., Hancock, W. S., Karger, B. L. (2009) Mass spectrometric determination of disulphide linkages in recombinant therapeutic proteins using online LC-MS with electron-transfer dissociation. Anal. Chem. 81, 112-122.

Yau, K. Y. F., Dubuc, G., Li, S., Hirama, T., Mackenzie, C. R., Jermutus, L., Hall, J. C., and Tanha, J. (2005) Affinity maturation of a $V_H$H by mutational hotspot randomization. Immunol. Methods 297, 213-224.

Zhang, J., Li, Q., Nguyen, T.-D., Tremblay, T.-L., Stone, E., To, R., Kelly, J. and MacKenzie, C. R. (2004a) A pentavalent single-domain antibody approach to tumor antigen discovery and the development of novel proteomics reagents. J. Mol. Biol. 341, 161-169.

Zhang, J., Tanha, J., Hirama, T., Khieu, N. H., To, R., Tong-Sevinc, H., Stone, E., Brisson, J.-R. and MacKenzie, C. R. (2004b) Pentamerization of single-domain antibodies from phage libraries: A novel strategy for the rapid generation of high-avidity antibody reagents. J. Mol. Biol. 335, 49-56.

Zhang, J., Liu, X., Bell, A., To, R., Baral, T. N., Azizi, A., Li, J., Cass, B., and Durocher, Y. (2009) Transient expression and purification of chimeric heavy chain antibodies. Protein Expr. Purif. 65, 77-82.

WO 95/04069
WO/2004/076670
WO2003/046560
WO2006/099747

The invention claimed is:

1. A synthetic immunoglobulin scaffold comprising one or more than one non-canonical disulfide bond between framework region 2 (FR2) and framework region 3 (FR3), wherein the immunoglobulin scaffold is a human $V_L$ scaffold, and wherein the non-canonical disulfide bond is formed between cysteine residues introduced at position 48 in FR2 and position 64 in FR3, wherein the positions are based on Kabat numbering, wherein the human $V_L$ scaffold is at least 90% identical, including conservative amino acid mutations but disregarding the residues within complementarity determining regions (CDRs), to one or more of SEQ ID NOs: 2, 4, 6, 8, 10, 12, 14, 16, 18, 20, 22, and 24.

2. The synthetic immunoglobulin scaffold of claim 1, wherein the synthetic immunoglobulin scaffold is immobilized onto a surface.

3. A polypeptide comprising the synthetic immunoglobulin scaffold of claim 1, selected from the group consisting of a single domain antibody (sdAb), scFv, Fab, F(ab)$_2$, and mature immunoglobulin.

4. The polypeptide of claim 3, wherein the mature immunoglobulin is selected from the group consisting of an IgG1, IgG2, IgG3, IgG4, IgE, and/or IgM.

5. A composition comprising the synthetic immunoglobulin scaffold of claim 1.

6. The synthetic immunoglobulin scaffold of claim 1, wherein the $V_L$ is of the kappa or lambda family.

7. The polypeptide of claim 3, wherein the synthetic immunoglobulin scaffolds are multimerized, wherein the resulting multimer comprises at least a dimer, a trimer, tetramer, pentamer, hexamer, heptamer or an octamer.

8. The polypeptide of claim 3, wherein the synthetic immunoglobulin scaffold is fused to an Fc fragment, a targeting sequence, a signal sequence, a purification tag, or any combination thereof.

9. The polypeptide of claim 3, wherein the synthetic immunoglobulin scaffold is linked to a cargo molecule.

10. A recombinant library comprising at least one synthetic immunoglobulin scaffold as defined in claim 1, wherein the synthetic immunoglobulin scaffold further comprises a multiplicity of suitable CDR sequences, wherein the multiplicity of CDR sequences provide a diversity of at least $10^5$, at least $10^6$, at least $10^7$, at least $10^8$, at least $10^9$ or more than $10^9$ clones per library.

* * * * *